US008048880B2

(12) United States Patent
Trias et al.

(10) Patent No.: US 8,048,880 B2
(45) Date of Patent: Nov. 1, 2011

(54) TREATMENT OF CARDIOVASCULAR DISEASE AND DYSLIPIDEMIA USING SECRETORY PHOSPHOLIPASE $A_2$ ($sPLA_2$) INHIBITORS AND $sPLA_2$ INHIBITOR COMBINATION THERAPIES

(75) Inventors: Joaquim Trias, Millbrae, CA (US);
Colin Hislop, Menlo Park, CA (US);
Paul Truex, Pleasanton, CA (US);
Bernadine Fraser, Sunnyvale, CA (US);
Debra Odink, Oakland, CA (US); Scott Chadwick, Redwood City, CA (US);
Kenneth Gould, Zionsville, IN (US);
Marian Mosior, Indianapolis, IN (US);
Patrick Eacho, Indianapolis, IN (US)

(73) Assignee: Anthera Pharmaceuticals, Inc., Hayward, CA (US)

( * ) Notice: Subject to any disclaimer, the term of this patent is extended or adjusted under 35 U.S.C. 154(b) by 390 days.

(21) Appl. No.: 12/114,710

(22) Filed: May 2, 2008

(65) Prior Publication Data

US 2009/0131396 A1    May 21, 2009

Related U.S. Application Data

(60) Provisional application No. 61/190,044, filed on Oct. 18, 2007, provisional application No. 60/969,591, filed on Aug. 31, 2007, provisional application No. 60/915,910, filed on May 3, 2007.

(51) Int. Cl.
*A61K 31/535*    (2006.01)
*A61K 31/397*    (2006.01)
*A61K 31/44*    (2006.01)
*A61K 31/40*    (2006.01)

(52) U.S. Cl. ............... 514/235.2; 514/210.02; 514/356; 514/422; 514/423

(58) Field of Classification Search ............... 514/235.2, 514/210.02, 356, 422, 423
See application file for complete search history.

(56) References Cited

U.S. PATENT DOCUMENTS

| | | | | |
|---|---|---|---|---|
| 3,485,847 | A | * 12/1969 | Bossert et al. | ............... 546/321 |
| 5,273,995 | A | * 12/1993 | Roth | ............... 514/422 |
| 5,504,073 | A |  4/1996 | Homan | |
| 5,578,634 | A | 11/1996 | Bach et al. | |
| 5,641,800 | A |  6/1997 | Bach et al. | |
| 5,654,326 | A | * 8/1997 | Bach et al. | ............... 514/419 |
| 5,684,034 | A | 11/1997 | Bach et al. | |
| 5,767,115 | A | * 6/1998 | Rosenblum et al. | ..... 514/210.02 |
| 6,177,440 | B1 |  1/2001 | Bach et al. | |
| 6,252,084 | B1 |  6/2001 | Bach et al. | |
| 6,274,578 | B1 |  8/2001 | Denney et al. | |
| 6,472,389 | B1 | 10/2002 | Ohtani et al. | |
| 6,713,645 | B1 |  3/2004 | Bach et al. | |
| 6,756,376 | B1 |  6/2004 | Fuji et al. | |
| 7,026,318 | B2 |  4/2006 | Ogawa et al. | |
| 7,098,237 | B1 |  8/2006 | Todo | |
| 2004/0248898 | A1 | 12/2004 | Saiga et al. | |
| 2006/0094693 | A1 |  5/2006 | Aziz et al. | |
| 2006/0223865 | A1 | 10/2006 | Buch et al. | |
| 2007/0135385 | A1 |  6/2007 | Chang et al. | |

FOREIGN PATENT DOCUMENTS

| | | |
|---|---|---|
| EP | 1378246 A1 | 1/2004 |
| WO | WO 96/03376 | 2/1996 |
| WO | WO 99/56752 | 11/1999 |
| WO | 00/28332 A1 | 5/2000 |
| WO | 01/36420 A1 | 5/2001 |
| WO | WO 01/55108 A2 | 8/2001 |
| WO | 02/08189 A1 | 1/2002 |
| WO | 2004/103960 A2 | 12/2004 |
| WO | 2005/028653 A1 | 3/2005 |
| WO | 2005/058310 A2 | 6/2005 |
| WO | WO 2007/056281 A2 | 5/2007 |

OTHER PUBLICATIONS

Clark et al., "Potential therapeutic uses of phospholipase A2 inhibitors", Expert Opinion on Therapeutic Patents, vol. 14, No. 7, pp. 937-950 (2004).*
Aviram, M. et al., "Phospholipase A2-Modified LDL Is Taken Up at Enhanced Rate by Macrophages," Biochem Biophys Res Commun 185:465-472 (1992).
Boekholdt, S. M., et al., "Serum Levels of Type II Secretory Phospholipase A2 and the Risk of Future Coronary Artery Disease in Apparently Healthy Men and Women: The EPIC-Norfolk Prospective Population Study," Arterioscler. Thromb. Vasc. Biol. 25:839-846 (2005).
Bostrom, M. A., et al., "Group V Secretory Phospholipase A2 Promotes Atherosclerosis: Evidence From Genetically Altered Mice," Arterioscler. Thromb. Vasc. Bio. 27:600-606 (2007).
Boyanovsky, B., et al., "Group V Secretory Phospholipase A2-modified Low Density Lipoprotein Promotes Foam Cell Formation by a SR-A- and CD36- independent Process That Involves Cellular Proteoglycans," J Biol Chem 280:32746-32752 (2005).

(Continued)

*Primary Examiner* — Kevin E Weddington
(74) *Attorney, Agent, or Firm* — Perkins Coie LLP; Patrick D. Morris

(57) ABSTRACT

Administration of $sPLA_2$ inhibitors has been found to decrease cholesterol levels, atherosclerotic plaque formation and aortic aneurysm in mice, and to decrease cholesterol and triglyceride levels in humans. Interestingly, administration of $sPLA_2$ inhibitors was found to decrease cholesterol levels even when the inhibitors were administered only once per day. Therefore, provided herein are methods of treating dyslipidemia, CVD, and conditions associated with CVD such as atherosclerosis and metabolic syndrome, by administering one or more $sPLA_2$ inhibitors. Significantly, administration of $sPLA_2$ inhibitors and various compounds used in the treatment of CVD, such as for example statins, resulted in greater decreases in LDL and LDL particle levels in a synergistic manner. In addition, administration of $sPLA_2$ inhibitors and statins resulted in a synergistic decrease in plaque content. Therefore, also provided herein are compositions comprising one or more $sPLA_2$ inhibitors and one or more compounds used in the treatment of CVD, such as for example statins, and methods of using these compositions to treat dyslipidemia, CVD, and conditions associated with CVD such as atherosclerosis and metabolic syndrome.

30 Claims, 12 Drawing Sheets

OTHER PUBLICATIONS

Camejo, G., et al., "Association of Apo B Lipoproteins with Arterial Proteoglycans: Pathological Significance and Molecular Basis," Arterioscler. 139:205-222 (1998).

Chait, A., et al., "Lipoprotein-Associated Inflammatory Proteins: Markers or Mediators of Cardiovascular Disease?," J Lipid Res. 46:389-403 (2005).

Daugherty, A., et al., "Angiotensin II Promotes Atherosclerotic Lesions and Aneurysms in Apolipoprotein E-Deficient Mice," J Clin. Invest. 105:1605-1612 (2000).

De Beer, F. C., et al., "Secretory Non-Pancreatic Phospholipase A2: Influence on Lipoprotein Metabolism," J Lipid Res. 38:2232-2239 (1997).

Divchev, D., et al., "The Secretory Phospholipase A2 Group IIA: A Missing Link Between Inflammation, Activated Renin-Angiotensin System, and Atherogenesis," Vasc Health Risk Manag 4:597-604 (2008).

Draheim, S.E., et al., "Indole Inhibitors of Human Nonpancreatic Secretory Phospholipase A2. 3. Indole-3-Glyoxamides," J Med Chem 39:5159-5175 (1996).

Eckey, R., et al., "Increased Hepatic Cholesterol Accumulation in Transgenic Mice Overexpressing Human Secretory Phospholipase $A_2$ Group IIA," Inflammation 28:59-65 (2004).

Elinder, L. S., et al., "Expression of Phospholipase A2 Isoforms in Human Normal and Atherosclerotic Arterial Wall," Arterioscler. Thromb. Vasc. Biol. 17:2257-2263 (1997).

Flood, C., et al., "Molecular Mechanism for Changes in Proteoglycan Binding on Compositional Changes of the Core and the Surface of Low-Density Lipoprotein—Containing Human Apolipoprotein B100," Arterioscler Thromb Vasc Biol 24:564-570 (2004).

Ghesquiere, S., et al., "Macrophage-Specific Overexpression of Group IIa sPLA2 Increases Atherosclerosis and Enhances Collagen Deposition," J Lipid Res 46:201-210 (2005).

Hakala, J. K., et al., "Lipolysis of LDL by Human Secretory Phospholipase A2 Induces Particle Fusion and Enhances the Retention of LDL to Human Aortic Proteoglycans," Arterioscler. Thromb. Vasc. Biol. 21:1053-1058 (2001).

Hanasaki, K., et al., "Potent Modification of Low Density Lipoprotein by Group X Secretory Phospholipase A2 Is Linked to Macrophage Foam Cell Formation," J Biol Chem 277:29116-29124 (2002).

Hartford, M., et al., "CRP, Interleukin-6, Secretory Phospholipase A2 Group IIA, and Intercellular Adhesion Molecule-1 During the Early Phase of Acute Coronary Syndromes and Long-Term Follow-Up," J Cardiol. 108:55-62 (2006).

Hurt-Camejo, E., et al., "Localization of Nonpancreatic Secretory Phospholipase A2 in Normal and Atherosclerotic Arteries," Arterioscler Thromb Vasc Biol 17:300-309 (1997).

Hurt-Camejo, E., et al., "Cellular Consequences of the Association of ApoB Lipoproteins with Proteoglycans," Arterioscler Thromb Vasc Biol 17:1011-1017 (1997).

Hurt-Camejo, E., et al., "Phospholipase A2 in Vascular Disease," Circ Res 89:298-304 (2001).

Ivandic, B., et al., "Role of Group II Secretory Phospholipase A2 in Atherosclerosis: 1. Increased Atherogenesis and Altered Lipoproteins in Transgenic Mice Expressing Group IIa Phospholipase A2," Arterioscler. Thromb. Vasc. Biol. 19:1284-1290 (1999).

Jialal, I., "Evolving Lipoprotein Risk Factors: Lipoprotein(a) and Oxidized Low-Density Lipoprotein," Clin. Chem. 44:1827-1832 (1998).

Karabina, S.A., et al., "Atherogenic Properties of LDL Particles Modified by Human Group X Secreted Phospholipase A2 on Human Endothelial Cell Function," FASEB J 20:2547 (2006).

Kimura-Matsumoto, M., et al., "Expression of Secretory Phospholipase A2s in Human Atherosclerosis Development," Atherosclerosis, doi:10.1016/j.atherosclerosis.2006.08.062 (2007).

Kougias, P., et al., "Lysophosphatidylcholine and Secretory Phospholipase A2 in Vascular Disease: Mediators of Endothelial Dysfunction and Atherosclerosis," Med Sci Monit 12:RA5-RA16 (2006).

Kovanen, P. T., et al., "Secretory Group II Phospholipase A2: A Newly Recognized Acute-Phase Reactant With a Role in Atherogenesis," Circ Res 86:610-612 (2000).

Kugiyama, K., et al., "Circulating Levels of Secretory Type II Phospholipase A2 Predict Coronary Events in Patients with Coronary Artery Disease," Circulation 100:1280-1284 (1999).

Leitinger, N., et al., "Role of Group II Secretory Phospholipase A2 in Atherosclerosis : 2. Potential Involvement of Biologically Active Oxidized Phospholipids," Arterioscler Thromb Vasc Biol 19:1291-1298 (1999).

Levick, S. et al., "Antifibrotic Activity of an Inhibitor of Group IIA Secretory Phospholipase A2 in Young Spontaneously Hypertensive Rats," J Immunol 176:7000-7007 (2006).

Liu, P.Y., et al., "Prognostic Value and the Changes of Plasma Levels of Secretory Type II Phospholipase A2 in Patients with Coronary Artery Disease Undergoing Percutaneous Coronary Intervention," Eur Heart J 24:1824-1832 (2003).

Mallat, Z., et al., "Circulating Secretory Phospholipase A2 Activity and Risk of Incident Coronary Events in Healthy Men and Women: The Epic-Norfolk Study," Arterioslcer. Thromb. Vasc. Biol. 27:1177-1183 (2007).

Mallat, Z., et al., "Circulating Secretory Phospholipase A2 Activity Predicts Recurrent Events in Patients with Severe Acute Coronary Syndromes," J Am. Coll. Cardiol. 46:1249-1257 (2005).

Menschikowski, M., et al., "Secretory Group II Phospholipase A2 in Human Atherosclerotic Plaques," Atheroscler. 118:173-181 (1995).

Menschikowski, M., et al., "Secretory Phospholipase A2 of Group IIA: Is It an Offensive or a Defensive Player During Atherosclerosis and Other Inflammatory Diseases?," Prostaglandins Other Lipid Mediat 79:1-33 (2005).

Murakami, M. & Kudo, I., "New phospholipase A2 isozymes with a potential role in atherosclerosis," Curr Opin Lipidol 14:431-436 (2003).

Murakami, M., et al., "Diversity of Phospholipase A2 Enzymes: Secretory Phospholipase A2," Biol Pharm Bull 27:1158-1164 (2004).

Niessen, H., et al., "Type II Secretory Phospholipase A2 in Cardiovascular Disease: A Mediator in Atherosclerosis and Ischemic Damage to Cardiomyocytes?," Cardiovasc Res 60:68-77 (2003).

Nijmeijer, R., et al., "Secretory Type II Phospholipase A2 Binds to Ischemic Myocardium During Myocardial Infarction in Humans," Cardiovasc. Res. 53:138-146 (2002).

Oorni, K. et al., "PLA2-V: A Real Player in Atherogenesis," Arterioscler Thromb Vasc Biol 27:445-447 (2007).

Paradis, M-E., et al., "Visceral Adipose Tissue Accumulation, Secretory Phospholipase A2-IIA and Atherogenecity of LDL," Int. J Obesity 30:1615-1622 (2006).

Piek, J., et al., "Type II Secretory Phospholipase A2: The Emerging Role of Biochemical Markers of Plaque Inflammation," Eur Heart J 24:1804-1806 (2003).

Pruzanski, W., et al., "Lipoproteins are Substrates for Human Secretory Group IIA Phospholipase A2: Preferential Hydrolysis of Acute Phase HDL," J Lipid Res. 39:2150-2160 (1998).

Ramoner, R., et al., "Dendritic-Cell Activation by Secretory Phospholipase A2," Blood 105:3583-3587 (2005).

Romano, M., et al., "Ultrastructural Localization of Secretory Type II Phospholipase A2 in Atherosclerotic and Nonatherosclerotic Regions of Human Arteries," Arterioscler Thromb Vasc Biol 18:519-525 (1998).

Rosengren, B., et al., "Secretory Phospholipase A2 Group V: Lesion Distribution, Activation by Arterial Proteoglycans, and Induction in Aorta by a Western Diet," Arterioscler. Thromb. Vasc. Biol. 26:1579-1585 (2006).

Saiga, A., et al., "Group X Secretory Phospholipase A2 Induces Potent Productions of Various Lipid Mediators in Mouse Peritoneal Macrophages," Biochim Biophys Acta 1530:67-76 (2001).

Sartipy, P., et al., "Binding of Human Phospholipase A2 Type II to Proteoglycans," J Biol Chem 271:26307-26314 (1996).

Sartipy, P., et al., "Phospholipase A2 Modification of Low Density Lipoproteins Forms Small High Density Particles with Increased Affinity for Proteoglycans and Glycosaminoglycans," J Biol. Chem. 274:25913-25920 (1999).

Schiering, A., et al., "Analysis of secretory group II phospholipase A2 expression in human aortic tissue in dependence on the degree of atherosclerosis," Atherosclerosis 144:73-78 (1999).

Scott, K.F., et al., "Secreted Phospholipase A2 Enzymes as Therapeutic Targets," Expert Opin Ther Targets 7:427-440 (2003).

Snyder, D. W., et al., "Pharmacology of LY315920/S-5920,1 [[3-(Aminooxoacetyl)-2-ethyl-1-(phenylmethyl)-1H-indol-4-yl]oxy]acetate, A Potent and Selective Secretory Phospholipase A2 Inhibitor: A New Class of Anti-Inflammatory Drugs, SPI," J Pharmacol Exp Ther 288:1117 (1999).

Sparrow, C. P., et al., "Enzymatic Modification of Low Density Lipoprotein by Purified Lipoxygenase Plus Phospholipase AP Mimics Cell-Mediated Oxidative Modification," J Lipid Res 29:745-753 (1988).

Szmitko, P. E., et al., "Biomarkers of Vascular Disease Linking Inflammation to Endothelial Activation: Part II," Circulation 108:2041-2048 (2003).

Tietge, U. J. F., et al., "Overexpression of Secretory Phospholipase A2 Causes Rapid Catabolism and Altered Tissue Uptake of High Density Lipoprotein Cholesteryl Ester and Apolipoprotein A-I," J Biol. Chem. 275:10077-10084 (2000).

Tietge, U., et al., "Macrophage-Specific Expression of Group IIA sPLA2 Results in Accelerated Atherogenesis by Increasing Oxidative Stress," J Lipid Res 46:1604-1614 (2005).

United States Patent and Trademark Office, Combined International Search Report and Written Opinion for PCT/US08/62577, dated Aug. 4, 2008.

Webb, N., et al., "Macrophage-Expressed Group IIA Secretory Phospholipase A2 Increases Atherosclerotic Lesion Formation in LDL Receptor—Deficient Mice," Arterioscler Thromb Vasc Biol 23:263-268 (2003).

Webb, N., "Secretory Phospholipase A2 Enzymes in Atherogenesis," Curr Opin Lipidology 16:341-344 (2005).

Wootton, P., et al., "Tagging SNP Haplotype Analysis of the Secretory PLA2-V gene, PLA2G5, Shows Strong Association with LDL and oxLDL Levels, Suggesting Functional Distinction from sPLA2-IIA: Results From the UDACS Study," Hum Mol Genet 16:1437-1444 (2007).

Wooton-Kee, C. R., et al., "Group V sPLA2 Hydrolysis of Low-Density Lipoprotein Results in Spontaneous Particle Aggregation and Promotes Macrophage Foam Cell Formation," Arterioscler Thromb Vasc Biol 24:762-767 (2004).

Ballantyne, C.M., et al., "Effect of ezetimibe coadministered with atorvastatin in 628 patients with primary hypercholesterolemia: a prospective, randomized, double-blind trial," Circulation 97:2409-2415 (2003).

Bays, H.E., et al., "Effects of colesevelam hydrochloride on low-density lipoprotein cholesterol and high-sensitivity C-reactive protein when added to statins in patients with hypercholesterolemia," Am J Cardiol 97:1198-1205 (2006).

Davidson, M.H., et al., "Ezetimibe coadministered with simvastatin in patients with primary hypercholesterolemia," J Am Coll Cardiol 40:2125-2134 (2002).

Elsayed, R.K. and Evans, J.D., "Emerging lipid-lowering drugs: squalene synthase inhibitors," Expert Opin Emerging Drugs 13:309-322 (2008).

Fichtlscherer, S., et al., "Elevated Secretory Non-Pancreatic Type II Phospholipase A2 Serum Activity is Associated with Impaired Endothelial Vasodilator Function in Patients with Coronary Artery Disease," Clin Sci 106:511-517 (2004).

Hunninghake, D., et al., "Coadministration of colesevelam hydrochloride with atorvastatin lowers LDL cholesterol additively," Atherosclerosis 158:407-416 (2001).

Jaross, W., et al., "Biological effects of secretory phospholipase A2 group IIA on lipoproteins and in atherogenesis," Eur J Clin Invest 32:383-393 (2002).

Kerzner, B., et al., "Efficacy and safety of ezetimibe coadministered with lovastatin in primary hypercholesterolemia," Am J Cardiol 91:418-424 (2003).

Kugiyama, K, et al., "Prognostic Value of Plasma Levels of Secretory Type II Phospholipase A2 in Patients with Unstable Angina Pectoris," Am J Cardiol 86:718-722 (2000).

Labeque, R., et al., "Enzymatic Modification of Plasma Low Density Lipoproteins in Rabbits: A Potential Treatment for Hypercholesterolemia," Proc Natl Acad Sci USA 90:3476-3480 (1993).

Melani, L., et al., "Efficacy and safety of ezetimibe coadministered with pravastatin in patients with primary hypercholesterolemia: a prospective, randomized, double-blind trial," Eur Heart J 24:717-728 (2003).

Menschikowski, M., et al., "Expression of Human Secretory Group IIA Phospholipase A2 Is Associated with Reduced Concentrations of Plasma Cholesterol in Transgenic Mice," Inflammation 24:227-237 (2000).

Menschikowski, M., et al., "Statins potentiate the IFN-γ-induced upregulation of group IIA phospholipase A2 in human aortic smooth muscle cells and HepG2 hepatoma cells," Biochim Biophys Acta 1733:157-171 (2005).

Mohler, E. R., et al., "The Effect of Darapladib on Plasma Lipoprotein-Associated Phospholipase A2 Activity and Cardiovascular Biomarkers in Patients with Stable Coronary Heart Disease or Coronary Heart Disease Risk Equivalent," J Am Coll Cardiol 51:1632-1641 (2008).

Pearson, T.A., et al., "Pooled analyses of effects on C-reactive protein and low density lipoprotein cholesterol in placebo-controlled trials of ezetimibe monotherapy or ezetimibe added to baseline statin therapy," Biochim Biophys Acta 1636:108-118 (2004).

Petry, C., et al., "Inhibition of Rho modulates cytokine-induced prostaglandin E2 formation in renal mesangial cells," Biochim Biophys Acta 1636:108-118 (2004).

Pirkova, A.A., et al., "Effect of Therapy with Atorvastatin on the Level of Secretory Phospholipase A2 Group IIA and Modification of Low Density Lipoproteins in Patients with Ischemic Heart Disease," Kardiologiia 4:37-40 (2007).

Porela, P., et al., "Level of circulating phospholipase A2 in prediction of the prognosis of patients with suspected myocardial infarction," Basic Res Cardiol 95:413-417 (2000).

Serruys, P. W., et al., "Effects of the Direct Lipoprotein-Associated Phospholipase A2 Inhibitor Darapladib on Human Coronary Atherosclerotic Plaque," Circulation 118:1172-1182 (2008).

Tietge, U.J.F., et al., "Human Secretory Phospholipase A2 Mediates Decreased Plasma Levels of HDL Cholesterol and ApoA-I in Response to Inflammation in Human ApoA-I Transgenic Mice," Arterioscler. Thromb Vasc Biol 22:1213-1218 (2002).

Clark, J. D., et al., "Potential Therapeutic Uses of Phospholipase A2 Inhibitors," Expert Opin. Ther. Patents 14 (7):937-950 (2004).

Abraham, E., et al., "Efficacy and Safety of LY315920Na/S-5920, A Selective Inhibitor of 14-kDa Group IIA Secretory Phospholipase A2, in Patients with Suspected Sepsis and Organ Failure," Crit. Care. Med. 31:718-728 (2003).

Bowton, D. L., et al., "Impact of a Soluble Phospholipase A2 Inhibitor on Inhaled Allergen Challenge in Subjects with Asthma," Journal of Asthma 1:65-71 (2005).

Bradley, J. D., et al., "A Randomized, Double-Blinded, Placebo-Controlled Clinical Trial of LY333013, a Selective Inhibitor of Group II Secretory Phospholipase A2, in the Treatment of Rheumatoid Arthritis," J. Rheumatol. 32:417-23 (2005).

Pearson, T. A., et al., "Pooled Analyses of Effects on C-Reactive Protein and Low Density Lipoprotein Cholesterol in Placebo-Controlled Trials of Ezetimibe Monotherapy or Ezetimibe Added to Baseline Statin Therapy," Am. J. Cardiol. 103:369-374 (2009).

Winkler, E., et al., "Decreased Serum Cholesterol Level After Snake Bite (Vipera Palaestinae) as a Marker of Severity of Envenomation," J. Lab. Clin. Med. 121(6):774-8 (1993).

Zeiher, B. G., et al., "LY315920NA/S-5920, A Selective Inhibitor of Group IIA Secretory Phospholipase A2, Fails to Improve Clinical Outcome for Patients with Severe Sepsis," Crit. Care Med. 33:1741-1748 (2005).

Chen, W.M., et al., "Control of Capillary Formation by Membrane-Anchored Extracellular Inhibitor of Phospholipase $A_2$," FEBS Letters 522:113-118 (2002).

European Patent Office, Extended European Search Report dated Apr. 1, 2011 for European Application No. 08747605.7.

Ma, J., et al., "Are Evidence-Based Cardiovascular Prevention Therapies Being Used? A Review of Aspirin and Statin Therapies," Prevention and Control 1:285-295 (2005).

Robinson, J. G., et al., "Combination Therapy with Ezetimibe and Simvastatin to Achieve Aggressive LDL Reduction," Expert Reu. Cardiovasc. Ther. 4(4):461-476 (2006).

Rodondi, N., et al., "Aspirin for the Primary Prevention of Cardiovascular Disease a Comprehensive Review," Comp. Ther. 31(3):186-193 (2005).

Vervoordeldonk, M., et al., "Aspirin Inhibits Expression of the Interleukin-1 β-Inducible Group II Phospholipase $A_2$," FEBS Letters 397:108-112 (1996).

Wiklund, O., et al., "Effects of Simvastatin and Atorvastatin on Inflammation Markers in Plasma," J. Int. Med. 251:338-347 (2002).

* cited by examiner

TREATMENT OF CARDIOVASCULAR DISEASE AND DYSLIPIDEMIA USING SECRETORY PHOSPHOLIPASE $A_2$ ($sPLA_2$) INHIBITORS AND $sPLA_2$ INHIBITOR COMBINATION THERAPIES

CROSS-REFERENCE TO RELATED APPLICATIONS

The subject application claims the benefit of U.S. Provisional Patent Application No. 61/190,044, filed Oct. 18, 2007, U.S. Provisional Patent Application No. 60/969,591, filed Aug. 31, 2007, and U.S. Provisional Patent Application No. 60/915,910, filed May 3, 2007. The disclosures of each of these applications are incorporated herein by reference in their entirety, including drawings.

BACKGROUND

In 2004, it was estimated that over 75 million Americans had one or more forms of cardiovascular disease (CVD). Coronary heart disease (CHD) and coronary artery disease (CAD) are the most common types of CVD. CHD and CAD occur when coronary arteries that supply blood to the heart become hardened and narrowed due to atherosclerosis. A variety of therapeutic options are currently employed in the treatment of CVD and conditions associated with CVD. Many of these therapeutic options function by lowering cholesterol levels, particularly LDL levels. Among the most popular and effective of these therapeutic options are statins, a class of compounds that inhibit cholesterol biosynthesis and prevent the build-up of arterial plaque. Statin administration has been shown to lower LDL and triglyceride levels and to substantially reduce coronary events and death from CVD. However, statin therapy alone is insufficient to completely treat CVD. Therefore, there is a need in the art for more effective methods of treating CVD and conditions associated with CVD.

SUMMARY

In certain embodiments, methods are provided for treating dyslipidemia in a subject in need thereof by administering a therapeutically effective amount of one or more $sPLA_2$ inhibitors. In certain embodiments, the one or more $sPLA_2$ inhibitors are administered in a composition that further comprises one or more pharmaceutically acceptable carriers. In certain embodiments, the one or more $sPLA_2$ inhibitors comprise A-001 or a pharmaceutically acceptable prodrug, salt, polymorph, co-crystal, or solvate of A-001. In certain of these embodiments, the one or more $sPLA_2$ inhibitors comprise A-002, a prodrug of A-001. In certain embodiments, administration of one or more $sPLA_2$ inhibitors results in a decrease in cholesterol and/or triglyceride levels. In certain of these embodiments, administration of one or more $sPLA_2$ inhibitors results in a decrease in total cholesterol, non-HDL cholesterol, LDL, LDL particle, small LDL particle, oxidized LDL, and/or ApoB levels. In certain embodiments, administration of one or more $sPLA_2$ inhibitors results in an increase in HDL levels and/or LDL particle size. In certain embodiments, administration of one or more $sPLA_2$ inhibitors results in a decrease in levels of one or more inflammatory markers. In certain of these embodiments, the inflammatory markers may include, but are not limited to, $sPLA_2$, CRP, and/or IL-6. In certain embodiments, administration of one or more $sPLA_2$ inhibitors results in an improvement in HDL/LDL ratio. In certain embodiments, the one or more $sPLA_2$ inhibitors may be administered to the subject twice or more per day, and in certain of these embodiments the one or more $sPLA_2$ inhibitors are administered twice per day. In other embodiments, the one or more $sPLA_2$ inhibitors may be administered to the subject on a once a day basis. In certain embodiments, the one or more $sPLA_2$ inhibitors may be administered at a dosage of about 50 to about 500 mg.

In certain embodiments, methods are provided for decreasing cholesterol levels in a subject in need thereof by administering a therapeutically effective amount of one or more $sPLA_2$ inhibitors. In certain embodiments, the one or more $sPLA_2$ inhibitors are administered in a composition that further comprises one or more pharmaceutically acceptable carriers. In certain embodiments, the one or more $sPLA_2$ inhibitors comprise A-001 or a pharmaceutically acceptable prodrug, salt, polymorph, co-crystal, or solvate of A-001. In certain of these embodiments, the one or more $sPLA_2$ inhibitors comprise A-002, a prodrug of A-001. In certain embodiments, administration of one or more $sPLA_2$ inhibitors results in a decrease in total cholesterol, non-HDL cholesterol, LDL, LDL particle, small LDL particle, oxidized LDL, and/or ApoB levels. In certain embodiments, administration of one or more $sPLA_2$ inhibitors results in an improvement in HDL/LDL ratio. In certain embodiments, the one or more $sPLA_2$ inhibitors may be administered to the subject twice or more per day, and in certain of these embodiments the one or more $sPLA_2$ inhibitors are administered twice per day. In other embodiments, the one or more $sPLA_2$ inhibitors may be administered to the subject on a once a day basis. In certain embodiments, the one or more $sPLA_2$ inhibitors may be administered at a dosage of about 50 to about 500 mg.

In certain embodiments, methods are provided for decreasing triglyceride levels in a subject in need thereof by administering a therapeutically effective amount of one or more $sPLA_2$ inhibitors. In certain embodiments, the one or more $sPLA_2$ inhibitors are administered in a composition that further comprises one or more pharmaceutically acceptable carriers. In certain of these embodiments, the one or more $sPLA_2$ inhibitors comprise A-001 or a pharmaceutically acceptable prodrug, salt, polymorph, co-crystal, or solvate of A-001. In certain of these embodiments, the one or more $sPLA_2$ inhibitors comprise A-002, a prodrug of A-001. In certain embodiments, the one or more $sPLA_2$ inhibitors may be administered to the subject twice or more per day, and in certain of these embodiments the one or more $sPLA_2$ inhibitors are administered twice per day. In other embodiments, the one or more $sPLA_2$ inhibitors may be administered to the subject on a once a day basis. In certain embodiments, the one or more $sPLA_2$ inhibitors may be administered at a dosage of about 50 to about 500 mg.

In certain embodiments, methods are provided for increasing HDL levels in a subject in need thereof by administering a therapeutically effective amount of one or more $sPLA_2$ inhibitors. In certain embodiments, the one or more $sPLA_2$ inhibitors are administered in a composition that further comprises one or more pharmaceutically acceptable carriers. In certain embodiments, the one or more $sPLA_2$ inhibitors comprise A-001 or a pharmaceutically acceptable prodrug, salt, polymorph, co-crystal, or solvate of A-001. In certain of these embodiments, the one or more $sPLA_2$ inhibitors comprise A-002, a prodrug of A-001. In certain embodiments, administration of one or more $sPLA_2$ inhibitors results in an improvement in HDL/LDL ratio. In certain embodiments, improvement in HDL/LDL ratio is further accomplished by a reduction in LDL levels. In certain embodiments, the one or more $sPLA_2$ inhibitors may be administered to the subject twice or more per day, and in certain of these embodiments the one or more sPLA$_2$ inhibitors are administered twice per day. In other embodiments, the one or more sPLA$_2$ inhibitors may be administered to the subject on a once a day basis. In certain embodiments, the one or more sPLA$_2$ inhibitors may be administered at a dosage of about 50 to about 500 mg.

In certain embodiments, methods are provided for treating CVD or a condition associated with CVD in a subject in need thereof by administering a therapeutically effective amount of one or more sPLA$_2$ inhibitors. In certain embodiments, the one or more sPLA$_2$ inhibitors are administered in a composition that further comprises one or more pharmaceutically acceptable carriers. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the one or more sPLA$_2$ inhibitors may be administered to the subject twice or more per day, and in certain of these embodiments the one or more sPLA$_2$ inhibitors are administered twice per day. In other embodiments, the one or more sPLA$_2$ inhibitors may be administered to the subject on a once a day basis. In certain embodiments, the one or more sPLA$_2$ inhibitors may be administered at a dosage of about 50 to about 500 mg. In certain embodiments, administration of one or more sPLA$_2$ inhibitors results in a decrease in levels of one or more inflammatory markers. In certain of these embodiments, the inflammatory markers may include, but are not limited to, sPLA$_2$, CRP, and/or IL-6. In certain embodiments, CVD or a condition associated with CVD includes, but is not limited to, atherosclerosis, metabolic syndrome, coronary artery disease, coronary heart disease, cerebrovascular disease, peripheral vascular disease, and/or conditions associated with coronary artery disease, coronary heart disease, cerebrovascular disease, or peripheral vascular disease.

In certain embodiments, methods are provided for treating metabolic syndrome in a subject in need thereof by administering a therapeutically effective amount of one or more sPLA$_2$ inhibitors. In certain embodiments, the one or more sPLA$_2$ inhibitors are administered in a composition that further comprises one or more pharmaceutically acceptable carriers. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the one or more sPLA$_2$ inhibitors may be administered to the subject twice or more per day, and in certain of these embodiments the one or more sPLA$_2$ inhibitors are administered twice per day. In other embodiments, the one or more sPLA$_2$ inhibitors may be administered to the subject on a once a day basis. In certain embodiments, the one or more sPLA$_2$ inhibitors may be administered at a dosage of about 50 to about 500 mg. In certain embodiments, administration of one or more sPLA$_2$ inhibitors results in a decrease in levels of one or more inflammatory markers. In certain of these embodiments, the inflammatory markers may include, but are not limited to, sPLA$_2$, CRP, and/or IL-6.

In certain embodiments, compositions are provided comprising one or more sPLA$_2$ inhibitors and one or more compounds used in the treatment of CVD. In certain embodiments, the composition further comprises one or more pharmaceutically acceptable carriers. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, pitavastatin, and various salts, solvates, stereoisomers, and prodrug derivatives thereof. In certain of these embodiments, the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics.

In certain embodiments, methods are provided for treating dyslipidemia in a subject in need thereof by administering a therapeutically effective amount of one or more sPLA$_2$ inhibitors and a therapeutically effective amount of one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, pitavastatin, and various salts, solvates, stereoisomers, and prodrug derivatives thereof. In certain of these embodiments, the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain embodiments, administration of one or more sPLA$_2$ inhibitors and one or more compounds used in the treatment of CVD results in a decrease in cholesterol levels and/or triglyceride levels. In certain of these embodiments, administration of one or more sPLA$_2$ inhibitors and one or more compounds used in the treatment of CVD results in a decrease in total cholesterol, non-HDL cholesterol, LDL, LDL particle, small LDL particle, oxidized LDL, and/or ApoB levels. In certain embodiments, administration of one or more sPLA$_2$ inhibitors and one or more compounds used in the treatment of CVD results in an increase in HDL levels and/or LDL particle size. In certain embodiments, administration of one or more sPLA$_2$ inhibitors and one or more compounds used in the treatment of CVD results in an improvement in HDL/LDL ratio. In certain embodiments, the one or more sPLA$_2$ inhibitors and the one or more compounds used in the treatment of CVD may be administered simultaneously. In certain of these embodiments, the one or more sPLA$_2$ inhibitors and the one or more compounds used in the treatment of CVD may be administered in a single formulation, while in other embodiments the compounds may be administered simultaneously in two or more formulations. In each of these embodiments, the formulation(s) may further comprise one or more pharmaceutically acceptable carriers. In other embodiments, the one or more sPLA$_2$ inhibitors and the one or more compounds used in the treatment of CVD may be administered sequentially. In certain embodiments, the one or more sPLA$_2$ inhibitors may be administered to the subject twice or more per day, and in certain of these embodiments the one or more sPLA$_2$ inhibitors are administered twice per day. In other embodiments, the one or more sPLA$_2$ inhibitors may be administered to the subject on a once a day basis. In certain embodiments, the one or more sPLA$_2$ inhibitors may be administered at a dosage of about 50 to about 500 mg. In certain embodiments, administration of one or more sPLA$_2$ inhibitors and one or more compounds used in the treatment of CVD results in a decrease in levels of one or more inflammatory markers. In certain of these embodiments, the inflammatory markers may include, but are not limited to, sPLA$_2$, CRP, and/or IL-6.

In certain embodiments, methods are provided for decreasing cholesterol levels in a subject in need thereof by administering a therapeutically effective amount of one or more sPLA$_2$ inhibitors and a therapeutically effective amount of one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, pitavastatin, and various salts, solvates, stereoisomers, and prodrug derivatives thereof. In certain of these embodiments, the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain embodiments, administration of one or more sPLA$_2$ inhibitors and one or more compounds used in the treatment of CVD results in a decrease in total cholesterol, non-HDL cholesterol, LDL, LDL particle, small LDL particle levels, oxidized LDL, and/or ApoB levels. In certain embodiments, administration of one or more sPLA$_2$ inhibitors and one or more compounds used in the treatment of CVD results in an increase in LDL particle size. In certain embodiments, administration of one or more sPLA$_2$ inhibitors and one or more compounds used in the treatment of CVD results in an improvement in HDL/LDL ratio. In certain embodiments, the one or more sPLA$_2$ inhibitors and the one or more compounds used in the treatment of CVD may be administered simultaneously. In certain of these embodiments, the one or more sPLA$_2$ inhibitors and the one or more compounds used in the treatment of CVD may be administered in a single formulation, while in other embodiments the compounds may be administered simultaneously in two or more formulations. In each of these embodiments, the formulation(s) may further comprise one or more pharmaceutically acceptable carriers. In other embodiments, the one or more sPLA$_2$ inhibitors and the one or more compounds used in the treatment of CVD may be administered sequentially. In certain embodiments, the one or more sPLA$_2$ inhibitors may be administered to the subject twice or more per day, and in certain of these embodiments the one or more sPLA$_2$ inhibitors are administered twice per day. In other embodiments, the one or more sPLA$_2$ inhibitors may be administered to the subject on a once a day basis. In certain embodiments, the one or more sPLA$_2$ inhibitors may be administered at a dosage of about 50 to about 500 mg.

In certain embodiments, methods are provided for decreasing triglyceride levels in a subject in need thereof by administering a therapeutically effective amount of one or more sPLA$_2$ inhibitors and a therapeutically effective amount of one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, pitavastatin, and various salts, solvates, stereoisomers, and prodrug derivatives thereof. In certain of these embodiments, the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain embodiments, the one or more sPLA$_2$ inhibitors and the one or more compounds used in the treatment of CVD may be administered simultaneously. In certain of these embodiments, the one or more sPLA$_2$ inhibitors and the one or more compounds used in the treatment of CVD may be administered in a single formulation, while in other embodiments the compounds may be administered simultaneously in two or more formulations. In each of these embodiments, the formulation(s) may further comprise one or more pharmaceutically acceptable carriers. In other embodiments, the one or more sPLA$_2$ inhibitors and the one or more compounds used in the treatment of CVD may be administered sequentially. In certain embodiments, the one or more sPLA$_2$ inhibitors may be administered to the subject twice or more per day, and in certain of these embodiments the one or more sPLA$_2$ inhibitors are administered twice per day. In other embodiments, the one or more sPLA$_2$ inhibitors may be administered to the subject on a once a day basis. In certain embodiments, the one or more sPLA$_2$ inhibitors may be administered at a dosage of about 50 to about 500 mg.

In certain embodiments, methods are provided for increasing HDL levels in a subject in need thereof by administering a therapeutically effective amount of one or more sPLA$_2$ inhibitors and a therapeutically effective amount of one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain of these embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, pitavastatin, and various salts, solvates, stereoisomers, and prodrug derivatives thereof. In certain of these embodiments, the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain embodiments, administration of one or more sPLA$_2$ inhibitors and one or more compounds used in the treatment of CVD results in an improvement in HDL/LDL ratio. In certain embodiments, improvement in HDL/LDL ratio is further accomplished by a reduction in LDL levels. In certain embodiments, the one or more sPLA$_2$ inhibitors and the one or more compounds used in the treatment of CVD may be administered simultaneously. In certain of these embodiments, the one or more sPLA$_2$ inhibitors and the one or more compounds used in the treatment of CVD may be administered in a single formulation, while in other embodiments the compounds may be administered simultaneously in two or more formulations. In each of these embodiments, the formulation(s) may further comprise one or more pharmaceutically acceptable carriers. In other embodiments, the one or more sPLA$_2$ inhibitors and the one or more compounds used in the treatment of CVD may be administered sequentially. In certain embodiments, the one or more sPLA$_2$ inhibitors may be administered to the subject twice or more per day, and in certain of these embodiments the one or more sPLA$_2$ inhibitors are administered twice per day. In other embodiments, the one or more sPLA$_2$ inhibitors may be administered to the subject on a once a day basis. In certain embodiments, the one or more sPLA$_2$ inhibitors may be administered at a dosage of about 50 to about 500 mg.

In certain embodiments, methods are provided for treating CVD or a condition associated with CVD in a subject in need thereof by administering a therapeutically effective amount of one or more sPLA$_2$ inhibitors and one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, pitavastatin, and various salts, solvates, stereoisomers, and prodrug derivatives thereof. In certain of these embodiments, the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain embodiments, administration of one or more sPLA$_2$ inhibitors results in a decrease in levels of one or more inflammatory markers. In certain of these embodiments, the inflammatory markers may include, but are not limited to, sPLA$_2$, CRP, and/or IL-6. In certain embodiments, CVD or a condition associated with CVD includes, but is not limited to, atherosclerosis, metabolic syndrome, coronary artery disease, coronary heart disease, cerebrovascular disease, peripheral vascular disease, and/or conditions associated with coronary artery disease, coronary heart disease, cerebrovascular disease, or peripheral vascular disease. In certain embodiments, the one or more sPLA$_2$ inhibitors and the one or more compounds used in the treatment of CVD may be administered simultaneously. In certain of these embodiments, the one or more sPLA$_2$ inhibitors and the one or more compounds used in the treatment of CVD may be administered in a single formulation, while in other embodiments the compounds may be administered simultaneously in two or more formulations. In each of these embodiments, the formulation(s) may further comprise one or more pharmaceutically acceptable carriers. In other embodiments, the one or more sPLA$_2$ inhibitors and the one or more compounds used in the treatment of CVD may be administered sequentially. In certain embodiments, the one or more sPLA$_2$ inhibitors may be administered to the subject twice or more per day, and in certain of these embodiments the one or more sPLA$_2$ inhibitors are administered twice per day. In other embodiments, the one or more sPLA$_2$ inhibitors may be administered to the subject on a once a day basis. In certain embodiments, the one or more sPLA$_2$ inhibitors may be administered at a dosage of about 50 to about 500 mg.

In certain embodiments, methods are provided for treating metabolic syndrome in a subject in need thereof by administering a therapeutically effective amount of one or more sPLA$_2$ inhibitors and one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, pitavastatin, and various salts, solvates, stereoisomers, and prodrug derivatives thereof. In certain of these embodiments, the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain embodiments, administration of one or more sPLA$_2$ inhibitors results in a decrease in levels of one or more inflammatory markers. In certain of these embodiments, the inflammatory markers may include, but are not limited to, sPLA$_2$, CRP, and/or IL-6. In certain embodiments, the one or more sPLA$_2$ inhibitors and the one or more compounds used in the treatment of CVD may be administered simultaneously. In certain of these embodiments, the one or more sPLA$_2$ inhibitors and the one or more compounds used in the treatment of CVD may be administered in a single formulation, while in other embodiments the compounds may be administered simultaneously in two or more formulations. In each of these embodiments, the formulation(s) may further comprise one or more pharmaceutically acceptable carriers. In other embodiments, the one or more sPLA$_2$ inhibitors and the one or more compounds used in the treatment of CVD may be administered sequentially. In certain embodiments, the one or more sPLA$_2$ inhibitors may be administered to the subject twice or more per day, and in certain of these embodiments the one or more sPLA$_2$ inhibitors are administered twice per day. In other embodiments, the one or more sPLA$_2$ inhibitors may be administered to the subject on a once a day basis. In certain embodiments, the one or more sPLA$_2$ inhibitors may be administered at a dosage of about 50 to about 500 mg.

In certain embodiments, methods are provided for increasing the effectiveness of a compound used in the treatment of CVD in a subject by administering one or more sPLA$_2$ inhibitors to said subject. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the compound used in the treatment of CVD may be a statin or statin combination drug. In certain of these embodiments, the statin may be selected from the group consisting of atorvastatin, simvastatin, rosuvastatin, lovastatin, pravastatin, cerivastatin, fluvastatin, mevastatin, pitavastatin, and various salts, solvates, stereoisomers, and prodrug derivatives thereof. In certain of these embodiments, the statin combination drug may be selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the compound used in the treatment of CVD may be a non-statin compound selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain embodiments, the one or more sPLA$_2$ inhibitors may be administered simultaneously with the compound used in the treatment of CVD. In certain of these embodiments, the one or more sPLA$_2$ inhibitors and the compound used in the treatment of CVD may be administered in a single formulation, while in other embodiments the compounds may be administered simultaneously in two or more formulations. In each of these embodiments, the formulation(s) may further comprise one or more pharmaceutically acceptable carriers. In other embodiments, the one or more sPLA$_2$ inhibitors and the compound used in the treatment of CVD may be administered sequentially. In certain embodiments, the one or more sPLA$_2$ inhibitors may be administered to the subject twice or more per day, and in certain of these embodiments the one or more sPLA$_2$ inhibitors are administered twice per day. In other embodiments, the one or more sPLA$_2$ inhibitors may be administered to the subject on a once a day basis. In certain embodiments, the one or more sPLA$_2$ inhibitors may be administered at a dosage of about 50 to about 500 mg.

In certain embodiments, the use of one or more sPLA$_2$ inhibitors for preparation of a medicament for treating dyslipidemia, treating CVD and conditions associated with CVD, lowering cholesterol levels, lowering triglyceride levels, increasing HDL levels, and improving HDL/LDL ratios in a subject is provided. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the medicament further comprises one or more pharmaceutically acceptable carriers.

In certain embodiments, the use of one or more sPLA$_2$ inhibitors and one or more compounds used in the treatment of CVD for preparation of a medicament for treating dyslipidemia, treating CVD and conditions associated with CVD, lowering cholesterol levels, lowering triglyceride levels, increasing HDL levels, and/or improving HDL/LDL ratios in a subject is provided. In certain embodiments, the one or more sPLA$_2$ inhibitors comprise A-001 or a pharmaceutically acceptable prodrug, salt, polymorph, co-crystal, or solvate of A-001. In certain of these embodiments, the one or more sPLA$_2$ inhibitors comprise A-002, a prodrug of A-001. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, pitavastatin, and various salts, solvates, stereoisomers, and prodrug derivatives thereof. In certain of these embodiments, the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain embodiments, the medicament further comprises one or more pharmaceutically acceptable carriers.

In addition to the exemplary embodiments described above, further embodiments and aspects will become apparent by reference to the drawings and by study of the following descriptions.

DETAILED DESCRIPTION

Figure 1:
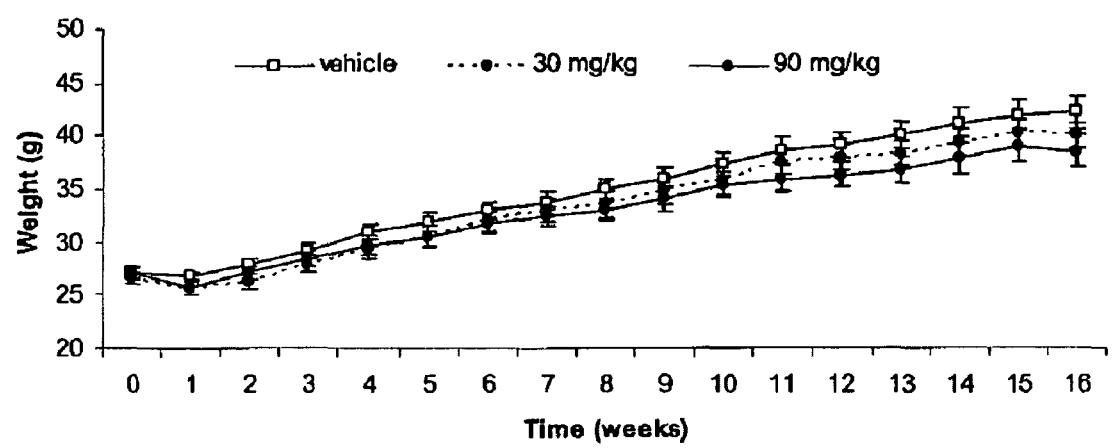
FIG. 1: Effect of A-002 administration on body weight in mice. ApoE$^{-/-}$-mice were administered vehicle only, 30 mg/kg A-002, or 90 mg/kg A-002 twice daily over 16 weeks. Body weight was measured once a week.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Abbreviations

AA, arachidonic acid; ACE, angiotensin converting enzyme; Ang, angiotensin; ApoB, apolipoprotein B; ARB, Angiotensin Receptor Blocker; BID, twice daily; BMI, body mass index; CAD, coronary artery disease; CETP, cholesteryl ester transfer protein; cfm, cubic feet per minute; CHD, coronary heart disease; CRP, C-reactive protein; CVD, cardiovascular disease; ECG, electrocardiogram; ERN, extended release niacin; HDL, high density lipoprotein; HMG-CoA, hydroxymethyl glutaryl coenzyme A; HPLC, high performance liquid chromatography; ICAM-1, intercellular adhesion molecule 1; IDL, intermediate density lipoprotein; IL, interleukin (e.g., IL-6, IL-8); ITT, intent to treat; LDL, low density lipoprotein; LPA, lysophosphatidic acid; MCP-1, monocyte chemotactic protein-1; MI, myocardial infarction; MIP-1α, macrophage inflammatory protein 1 alpha; MTP, microsomal triglyceride transfer protein; PAD, peripheral artery disease; PAF, platelet activating factor; PLA2, phospholipase $A_2$; QD, once daily; sPLA$_2$, secretory phospholipase $A_2$; TEAE, treatment-emergent adverse event; TG, triglyceride; TIA, transient ischemic attack; TNFα, tumor necrosis factor alpha; VCAM-1, vascular cell adhesion molecule 1; VLDL, very low density lipoprotein.

The terms "treat," "treating," or "treatment" as used herein with regards to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. For example, with regard to atherosclerosis, "treatment" may refer to a decrease in the likelihood of developing atherosclerotic plaque deposits, a decrease in the rate of development of deposits, a decrease in the number or size of existing deposits, or improved plaque stability. Likewise, "treatment" with regard to dyslipidemia may refer to a decrease in lipid levels, cholesterol levels, and/or triglyceride (TG) levels.

The term "subject" as used herein refers to any mammal, preferably a human.

In certain embodiments, a "subject in need thereof" refers to a subject diagnosed with CVD or exhibiting one or more conditions associated with CVD, a subject who has been diagnosed with or exhibited one or more conditions associated with CVD in the past, or a subject who has been deemed at risk of developing CVD or one or more conditions associated with CVD in the future due to hereditary or environmental factors. "Cardiovascular disease" or "CVD" as used herein includes, for example, atherosclerosis, including coronary artery atherosclerosis and carotid artery atherosclerosis, coronary artery disease (CAD), coronary heart disease (CHD), conditions associated with CAD and CHD, cerebrovascular disease and conditions associated with cerebrovascular disease, peripheral vascular disease and conditions associated with peripheral vascular disease, aneurysm, vasculitis, venous thrombosis, diabetes mellitus, and metabolic syndrome. "Conditions associated with CAD and CHD" as used herein include, for example, angina and myocardial infarction (MI; heart attack). "Conditions associated with cerebrovascular disease" as used herein include, for example, transient ischemic attack (TIA) and stroke. "Conditions associated with peripheral vascular disease" as used herein include, for example, claudication. "Conditions associated with CVD" as used herein include, for example, dyslipidemia, such as for example hyperlipidemia (elevated lipid levels), hypercholesterolemia (elevated cholesterol levels), and hypertriglyceridemia (elevated TG levels), elevated glucose levels, low HDL/LDL ratio, and hypertension. Therefore, in certain embodiments, a subject in need thereof may be a subject exhibiting dyslipidemia or a subject that has exhibited dyslipidemia in the past or has been deemed at risk for developing dyslipidemia in the future. In certain of these embodiments, the subject may exhibit elevated cholesterol levels, or may have exhibited elevated cholesterol levels in the past or been deemed at risk for developing elevated cholesterol levels in the future. Likewise, in certain of these embodiments, the subject may exhibit elevated triglyceride levels, or may have exhibited elevated triglyceride levels in the past or been deemed at risk for developing elevated triglyceride levels in the future. In certain embodiments, a subject in need thereof may have a condition associated with inflammation, may have been diagnosed with such a condition in the past, or may have been deemed at risk for developing such a condition in the future. In addition to atherosclerosis and certain other forms of CVD, conditions associated with inflammation include, for example, multiple sclerosis (Cunningham 2006), Alzheimer's disease (Moses 2006), sickle cell (Styles 1996), rheumatoid arthritis, and osteoarthritis (Jamal 1998). In these embodiments, a subject in need thereof may exhibit elevated $sPLA_2$ levels, may have exhibited elevated $sPLA_2$ levels in the past, or may have been deemed at risk for developing elevated $sPLA_2$ levels. In other embodiments, a subject in need thereof may exhibit $sPLA_2$ levels falling within a normal range. In certain embodiments, a subject in need thereof may exhibit elevated levels of one or more additional markers associated with inflammation, including but not limited to CRP, IL-6, MCP-1, TNFα, IL-8, ICAM-1, VCAM-1, and MIP-1α.

The term "cholesterol level" as used herein refers to blood cholesterol level, serum cholesterol level, plasma cholesterol level, or cholesterol level from another biological fluid. A decrease in cholesterol levels as used herein may refer to a decrease in total cholesterol levels or a decrease in one or more of total cholesterol, non-HDL cholesterol, LDL, VLDL, and/or IDL levels. A decrease in LDL as used herein may refer to a decrease in total LDL, a decrease in LDL particles, a decrease in small LDL particles, a decrease in oxidized LDL levels, and/or a decrease in ApoB levels. A decrease in VLDL as used herein may refer to a decrease in total VLDL or to a decrease in the level of one or more of VLDL subparticles V1 to V6. An improvement in HDL/LDL ratio as used herein refers to any increase in the ratio of HDL to LDL, and may be accomplished by decreasing LDL levels, increasing HDL levels, or some combination thereof. An increase in LDL particle size as used herein refers to an increase in mean particle size.

The term "elevated cholesterol level" as used herein refers to a cholesterol level that is above an accepted normal threshold level, such as those promulgated by the National Heart Lung and Blood Institute (NHLBI) National Cholesterol Education Program (NCEP). The accepted normal threshold cholesterol level may vary from subject to subject based on various risk factors, such as for example a prior history of CVD. In certain embodiments, a subject exhibiting elevated cholesterol levels may have a blood LDL level greater than or equal to 70 mg/dl. In certain of these embodiments, a subject exhibiting elevated cholesterol levels may have a blood LDL greater than or equal to 100 mg/dl, in other embodiments greater than or equal to 130 mg/dl, in other embodiments greater than or equal to 160 mg/dl, and in still other embodiments greater than or equal to 190 mg/dl. In certain embodiments, a subject exhibiting elevated cholesterol levels may have a blood total cholesterol level greater than or equal to 200 mg/dl. In certain of these embodiments, a subject exhibiting elevated cholesterol levels may have a blood total cholesterol greater than or equal to 240 mg/dl.

The term "triglyceride level" as used herein refers to blood triglyceride level, serum triglyceride level, plasma triglyceride level, or triglyceride level from another biological fluid. The term "elevated triglyceride level" as used herein refers to a triglyceride level that is above an accepted normal threshold level. The accepted normal threshold triglyceride level may vary from subject to subject based on various risk factors, such as for example a prior history of CVD. In certain embodiments, a subject exhibiting elevated triglyceride levels may have a blood triglyceride level greater than or equal to 150 mg/dl. In certain of these embodiments, a subject exhibiting elevated triglyceride levels may have a blood triglyceride level greater than or equal to 200 mg/dl, in other embodiments greater than or equal to 300 mg/dl, in other embodiments greater than or equal to 400 mg/dl, and in still other embodiments greater than or equal to 500 mg/dl.

The term "statin" as used herein refers to any compound that inhibits HMG-CoA reductase, an enzyme that catalyzes the conversion of HMG-CoA to mevalonate.

The term "$sPLA_2$ inhibitor" as used herein refers to any compound or prodrug thereof that inhibits the activity of $sPLA_2$.

A "therapeutically effective amount" of a composition as used herein is an amount of a composition that produces a desired therapeutic effect in a subject, such as treating a target condition. The precise therapeutically effective amount is an amount of the composition that will yield the most effective results in terms of therapeutic efficacy in a given subject. This amount will vary depending upon a variety of factors, including but not limited to the characteristics of the therapeutic composition (including, e.g., activity, pharmacokinetics, pharmacodynamics, and bioavailability), the physiological condition of the subject (including, e.g., age, body weight, sex, disease type and stage, medical history, general physical condition, responsiveness to a given dosage, and other present medications), the nature of the pharmaceutically acceptable carrier or carriers in the composition, and the route of administration. One skilled in the clinical and pharmacological arts will be able to determine a therapeutically effective amount through routine experimentation, namely by monitoring a subject's response to administration of a composition and adjusting the dosage accordingly. For additional guidance, see, e.g., Remington: The Science and Practice of Pharmacy, $21^{st}$ Edition, Univ. of Sciences in Philadelphia (USIP), Lippincott Williams & Wilkins, Philadelphia, Pa., 2005, and Goodman & Gilman's The Pharmacological Basis of Therapeutics, 11th Edition, McGraw-Hill, New York, N.Y., 2006, the entire disclosures of which are incorporated by reference herein.

A "pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. Such a carrier may comprise, for example, a liquid, solid, or semi-solid filler, solvent, surfactant, diluent, excipient, adjuvant, binder, buffer, dissolution aid, solvent, encapsulating material, sequestering agent, dispersing agent, preservative, lubricant, disintegrant, thickener, emulsifier, antimicrobial agent, antioxidant, stabilizing agent, coloring agent, or some combination thereof. Each component of the carrier must be "pharmaceutically acceptable" in that it must be compatible with the other ingredients of the composition and must be suitable for contact with any tissue, organ, or portion of the body that it may encounter, meaning that it must not carry a risk of toxicity, irritation, allergic response, immunogenicity, or any other complication that excessively outweighs its therapeutic benefits. Examples of pharmaceutically acceptable carriers for use in the presently disclosed pharmaceutical compositions include, but are not limited to, diluents such as microcrystalline cellulose or lactose (e.g., anhydrous lactose, lactose fast flo), binders such as gelatin, polyethylene glycol, wax, microcrystalline cellulose, synthetic gums such as polyvinylpyrrolidone, or cellulosic polymers such as hydroxypropyl cellulose (e.g., hydroxypropyl methylcellulose (HPMC)), lubricants such as magnesium stearate, calcium stearate, stearic acid, or microcrystalline cellulose, disintegrants such as starches, cross-linked polymers, or celluloses (e.g., croscarmellose sodium (CCNa), fillers such as silicon dioxide, titanium dioxide, microcrystalline cellulose, or powdered cellulose, surfactants or emulsifiers such as polysorbates (e.g., Polysorbate 20, 40, 60, or 80; Span 20, 40, 60, 65, or 80), antioxidant agents such as butylated hydroxyanisole (BHA), butylated hydroxytoluene (BHT), propyl gallate, or ascorbic acid (either free acid or salt forms thereof), buffers such as phosphate or citrate buffers, sequestering agents such as ethylenediaminetetraacetic acid (EDTA), ethylene glycol tetraacetic acid (EGTA), or edetate disodium, dispersing agents such as sodium carboxymethylceluose, hydroxypropyl methylcellulose, povidone, or polyvinylpyrrolidone, dissolution aids such as calcium carbonate, and excipients such as water, saline, dextrose, glycerol, or ethanol, citric acid, calcium metabisulfite, lactic acid, malic acid, succinic acid, or tartaric acid.

Metabolic syndrome is a disorder characterized by a group of metabolic risk factors. These factors include, for example, dyslipidemia, abdominal obesity, elevated blood pressure (hypertension), insulin resistance or glucose intolerance, prothrombotic state, and proinflammatory state. Subjects are generally classified as having metabolic syndrome if they meet three of the five following criteria: 1) abdominal obesity (waist circumference >35 inches in women, >40 inches in men); 2) low HDL levels (<50 mg/dL in women, <40 mg/dL in men); 3) high blood pressure ($\geqq$1130/85 mm Hg) or current treatment with antihypertensive medication; 4) hypertriglyceridemia (TG levels $\geqq$150 mg/dL); and 5) impaired fasting glucose (blood glucose levels of $\geqq$110 mg/dL). Metabolic syndrome is associated with elevated levels of various inflammatory markers, such as CRP or IL-6. Subjects with metabolic syndrome are at increased risk of developing CAD, CHD, conditions associated with CAD and CHD, and type 2 diabetes.

Over time, hypercholesterolemia and hypertriglyceridemia can lead to the development of atheromatous plaques on the inner arterial linings via the process of atherogenesis, which in turn results in atherosclerosis. Atherosclerosis leads to significantly reduced blood flow through the arteries, which in turn leads to the development of CAD, CHD, and conditions associated with CAD and CHD.

Reduction of cholesterol levels, particularly LDL levels, and/or reduction of TG levels have been shown to delay the onset and decrease the progression of atherosclerosis, thereby reducing the risk of developing CAD and CHD. In certain cases, adequate cholesterol and/or TG reduction may be accomplished through diet adjustment. In other cases, however, adequate reduction requires the administration of one or more compounds used in the treatment of CVD. Compounds used in the treatment of CVD include compounds for lowering cholesterol levels and/or increasing HDL levels, such as for example statins, bile acid sequestrants such as cholestyramine resin (Questran®, Prevalite®), colestipol hydrochloride (Colestid®), or colesevelam hydrochloride (WelChol®, Cholestagel®), fibrates such as bezafibrate (Bezalip®), ciprofibrate (Modalim®), clofibrate, gemfibrozil (Lopid®), or fenofibrate (Antara®, TriCor®, ABT-335), niacin or niacin derivatives such as xanthinol niacinate, niacin immediate-release (Niacor®), extended release forms of niacin (ERN) (Niaspan®, Niaspan MF, or Niaspan CF), or extended release niacin combinations (e.g., extended release niacin plus the DP-1 antagonist laropiprant (MK-0524), combination known as MK-0524A and marketed as Cordaptive®), cholesterol absorption inhibitors such as ezetimibe (Zetia®), AVE 5530, or MD-0727, cholesteryl ester transfer protein (CETP) inhibitors such as JTT-705/RO4607381 (R1658), CP-529414 (Torcetrapib®), or MK-0859, microsomal triglyceride transfer protein (MTP) inhibitors such as AEGR-733 and AEGR-733 combinations (e.g., AEGR-733 plus ezetimibe), squalene synthase inhibitors such as lapaquistat acetate (TAK-475) and lapaquistat acetate combinations (e.g., TAK-475 plus one or more statins), and other miscellaneous compounds such as dextrothyroxine, ISIS 301012, cardioprotectants such as MC-1 antibody, glycoprotein IIb/IIIa inhibitors such as tirofiban hydrochloride (Aggrastat®), TG100-115, AEGR 773, AEGR 427, stanols, or sterols. In addition to compounds that lower cholesterol levels or increase HDL levels, compounds used in the treatment of CVD include, for example, ACE inhibitors such as lisinopril, captopril, enalapril, nitrosated ACE inhibitors, or ACE inhibitor combinations (e.g., lisinopril plus MC-1 antibody, combination referred to as MC-4232), angiotensin II receptor antagonists, nitrosated angiotensin II receptor antagonists, or angiotensin II receptor antagonist combinations (e.g., Angiotensin Receptor Blocker (ARB) plus MC-1, combination referred to as MC-4262), beta-adrenergic blockers or nitrosated beta-adrenergic blockers, calcium channel blockers, or antithrombotics such as aspirin or nitrosated aspirin.

Among the most well-known and commonly used compounds used in the treatment of CVD are statins. Statins are compounds that inhibit HMG-CoA reductase from catalyzing the conversion of HMG-CoA to mevalonate, a rate-limiting step in the cholesterol biosynthetic pathway. As such, statins function as potent lipid lowering agent. Statin administration significantly decreases blood LDL levels, and moderately decreases blood TG levels. In addition, it has been proposed that statins may prevent CVD by improving endothelial function, modulating inflammatory responses, maintaining plaque stability, and preventing thrombus formation. Examples of statins that may be used in conjunction with the compositions and methods disclosed herein include, but are not limited to, atorvastatin or atorvastatin calcium (marketed as Lipitor® or Torvast®; see, e.g., U.S. Pat. Nos. 4,681,893 or 5,273,995) and atorvastatin combinations (e.g., atorvastatin plus amlodipine (marketed as Norvasc®), combination marketed as Caduet®, see, e.g., U.S. Pat. No. 6,455,574; atorvastatin plus CP-529414 (marketed as Torcetrapib®); atorvastatin plus APA-01; atorvastatin plus ezetimibe), cerivastatin (marketed as Lipobay® or Baycol®), fluvastatin (marketed as Lescol®; U.S. Pat. No. 4,739,073), lovastatin (marketed as Mevacor® or Altocor®; see, e.g., U.S. Pat. No. 4,231,938), lovastatin combinations (e.g., lovastatin plus Niaspan®, combination marketed as Advicor®), mevastatin, pitavastatin (marketed as Livalo® or Pitava®), pravastatin (marketed as Pravachol®, Mevalotin®, Selektine®, or Lipostat®; see, e.g., U.S. Pat. No. 4,346,227), pravastatin combinations (e.g., pravastatin plus fenofibrate), rosuvastatin (marketed as Crestor®), rosuvastatin combinations (e.g., rosuvastatin plus TriCor®), simvastatin (marketed as Zocor® or Lipex®; see, e.g., U.S. Pat. Nos. 4,444,784; 4,916,239; and 4,820,850), and simvastatin combinations (e.g., simvastatin plus ezetimibe, combination marketed as Vytorin®, see, e.g., U.S. Pat. No. 7,229,982; simvastatin plus Niaspan®, combination marketed as Simcor®; simvastatin plus MK-0524A, combination referred to as MK-0524B), as well as various pharmaceutically acceptable salts, solvates, salts, stereoisomers, prodrugs derivatives, or nitroderivatives of the compounds listed above. In some cases, such as for example with simvastatin, the active form of the statin is a metabolite formed in the body of a subject following administration. In other cases, statins are administered in their active form.

Phospholipases $A_2$ ($PLA_2$s) are a family of enzymes that catalyze hydrolysis of the sn-2 fatty acyl ester bond of phospholipids to produce free fatty acids and lysophospholipids such as arachidonic acid (AA) and lysophosphatidylcholine. AA can then be converted into eicosanoids such as prostaglandins, leukotrienes, thromboxanes, and lipoxins, while lysophosphatidylcholine can be metabolized to lysophosphatidic acid (LPA) or platelet-activating factor (PAF). $PLA_2$s have been classified into several groups based on factors such as cellular localization, amino acid sequence, molecular mass, and calcium requirement for enzymatic activity (Ramoner 2005).

Secretory phospholipase $A_2$ ($sPLA_2$) is an extracellular or secreted subgroup of $PLA_2$ that plays a role in inducing inflammation. Elevated levels of $sPLA_2$ types IIA, IID, IIE, IIF, III, V, and X have been observed in all stages of atherosclerosis development and have been implicated in atherogenesis based on their ability to degrade phospholipid (Kimura-Matsumoto 2007). $sPLA_2$ type IIA has been found to be expressed at vascular smooth muscle cells and foam cells in human arteriosclerosis lesions, and this expression has been recognized to have a correlation with the development of arteriosclerosis (Menschikowski 1995; Elinder 1997). Transgenic mice that express high levels of human type IIA $sPLA_2$ have increased LDL levels, decreased HDL levels, and arteriosclerotic lesions (Ivandic 1999; Tietge 2000), and develop arteriosclerosis at a higher rate compared to normal mice when given a high fat diet (Ivandic 1999). Treatment with $sPLA_2$ modifies LDL lipoproteins such that they have higher affinity for extracellular matrix proteins (Camejo 1998; Sartipy 1999; Hakala 2001), resulting in an increased retention of LDL particles in the arterial wall. In addition, there is some evidence that $sPLA_2$ remodels HDL, resulting in HDL catabolism (Pruzanski 1998). Increased expression of $sPLA_2$ type V has been shown to increase arteriosclerosis in mice, while a deficiency of $sPLA_2$ type V has been shown to reduce arteriosclerosis (Rosengren 2006; Bostrom 2007).

$sPLA_2$ expression has also been correlated with an increased risk of development of CAD. Higher circulating levels of $sPLA_2$, and of $sPLA_2$ type IIA specifically, have been observed in patients with documented CAD than in control patients (Kugiyama 1999; Liu 2003; Boekholdt 2005; Chait 2005; Hartford 2006). In addition, higher circulating levels of $sPLA_2$ were found to provide an accurate prognostic indicator for development of CAD in healthy individuals (Mallat 2007). Measurement of $sPLA_2$ activity has been shown to be an independent predictor of death and new or recurrent myocardial infarction in subjects with acute coronary syndrome, and provides greater prognostic accuracy than measuring type IIA concentration only (Mallat 2005). It has also been proposed that $sPLA_2$ may have detrimental effects in the setting of ischemic events. This is based largely on the finding of $sPLA_2$ depositions in the necrotic center of infarcted human myocardium (Nijmeijer 2002).

As disclosed herein, administration of the $sPLA_2$ inhibitor A-002, which is a prodrug form of A-001, decreased plasma total cholesterol levels, increased plasma HDL levels, and decreased atherosclerotic plaque formation and aortic aneurysm in mice. In humans with CVD, twice daily administration of A-002 decreased serum LDL, LDL particle, small LDL particle, total cholesterol, and TG levels. Decreases in LDL were observed in a diabetic subpopulation, as well as in a subpopulation exhibiting elevated baseline LDL levels, while decreases in TG levels were observed in a metabolic syndrome subpopulation. Additionally, administration of A-002 was found to decrease serum levels of the inflammatory markers $sPLA_2$, CRP, and IL-6. Surprisingly, similar results were obtained with once a day administration of A-002, which caused a decrease in LDL, non-HDL cholesterol, total cholesterol, small LDL particle, oxidized LDL, triglyceride, and ApoB levels and an increase in LDL particle size. In addition, once a day dosing with A-002 prevented the large increase in CRP levels observed in the placebo group. Based on the experimental results disclosed herein showing that administration of $sPLA_2$ inhibitors decreases total cholesterol levels, atherosclerotic plaque formation, and aortic aneurysm in mice, decreases total cholesterol, non-HDL cholesterol, LDL, LDL particle, small LDL particle, oxidized LDL particle, TG, and ApoB levels in humans, and increases LDL particle size in humans, administration of a therapeutically effective amount of one or more $sPLA_2$ inhibitors may be used to treat CVD and conditions associated with CVD, such as for example dyslipidemia, atherosclerosis, metabolic syndrome, CAD, CHD, and conditions associated with CAD and CHD.

Provided herein in certain embodiments are methods of treating CVD and conditions associated with CVD in a subject in need thereof by administering a therapeutically effective amount of one or more $sPLA_2$ inhibitors. In certain of these embodiments, administration of one or more $sPLA_2$ inhibitors may result in, among other effects, a decrease in cholesterol levels, a decrease in TG levels, an increase in LDL particle size, and/or an improvement in HDL/LDL ratio. Therefore, also provided herein are methods of treating dyslipidemia in a subject in need thereof. In certain embodiments, one or more $sPLA_2$ inhibitors for use in these methods comprise A-001 or a pharmaceutically acceptable prodrug, salt, polymorph, co-crystal, or solvate of A-001. In certain of these embodiments, the pharmaceutically acceptable prodrug is A-002. In certain embodiments, administration of one or more sPLA$_2$ inhibitors may result in a decrease in one or more markers associated with inflammation. Such markers include, but are not limited to, sPLA$_2$, CRP, and IL-6. Also provided herein are compositions comprising one or more sPLA$_2$ inhibitors for use in the methods disclosed herein, such as for example in the treatment of CVD, conditions associated with CVD, and/or dyslipidemia or to lower total cholesterol, LDL, non-HDL cholesterol, LDL particle, small LDL particle, oxidized LDL, ApoB, and/or triglyceride levels or to raise HDL levels. In certain embodiments, these compositions further comprise one or more pharmaceutically acceptable carriers.

Compositions comprising one or more sPLA$_2$ inhibitors for use in the methods disclosed herein may be administered to a subject on a one-time basis or in multiple administrations. In those embodiments wherein these compositions are given in multiple administrations, the compositions may be administered at set intervals over a particular time period determined in advance, or they may be administered indefinitely or until a particular therapeutic benchmark is reached, such as for example until a subject exhibits cholesterol levels below a specified threshold. In certain embodiments, the one or more sPLA$_2$ inhibitors may be administered from one or more times per day to once every week, once every month, or once every several months. In certain embodiments, the one or more sPLA$_2$ inhibitors may be administered twice a day, and in other embodiments the one or more sPLA$_2$ inhibitors may be administered once a day. As disclosed herein, both twice a day and once a day administration of A-002 resulted in significant decreases in serum lipid levels.

In certain embodiments, kits are provided that comprise one or more sPLA$_2$ inhibitors. In certain embodiments, the one or more sPLA$_2$ inhibitors comprise A-001 or a pharmaceutically acceptable prodrug, salt, polymorph, co-crystal, or solvate of A-001, and in certain of these embodiments, the pharmaceutically acceptable prodrug is A-002. In certain embodiments, the kit provides instructions for usage, such as dosage or administration instructions.

As disclosed herein, twice daily administration of A-002 was shown to further decrease total cholesterol levels in mice and LDL, LDL particle, and small LDL particle levels in humans that were receiving statin treatment. Likewise, A-002 was shown to further decrease serum LDL levels in humans that were receiving ezetimibe treatment. Similar results were obtained when A-002 was administered once a day in combination with statins. These results indicate that administration of an sPLA$_2$ inhibitor unexpectedly causes an additional decrease in cholesterol levels in subjects that are already being treated with another compound used in the treatment of CVD, such as a statin. As further disclosed herein, administration of A-002 in conjunction with statins resulted in an unexpected synergistic decrease in total cholesterol levels and aortic lesion formation in mice and in LDL and small LDL particle levels in humans. The synergistic decrease in LDL following co-administration of A-002 and statins was observed in the statin subpopulation as a whole. In addition, synergism appeared to occur between A-002 and each of the individual statins within the general statin subpopulation, although statistical analysis of this effect was complicated by the limited number of test and placebo subjects for each statin. These results indicate that the synergistic decrease in LDL levels generated by co-administration of A-002 and statins is not limited to one particular statin, but rather occurs across the entire range of statins. Administration of A-002 in conjunction with ezetimibe led to a similar synergistic decrease in LDL levels, indicating that the synergism between A-002 and compounds used in the treatment of CVD is not limited to statins. Therefore, methods are provided herein for treating CVD and conditions associated with CVD, including dyslipidemia and atherosclerosis, in a subject in need thereof by administering a therapeutically effective amount of one or more sPLA$_2$ inhibitors and a therapeutically effective amount of one or more compounds used in the treatment of CVD, such as for example statins. Also provided herein are methods of increasing the effectiveness of a compound used in the treatment of CVD, such as for example a statin, by administering one or more sPLA$_2$ inhibitors in conjunction with the compound used in the treatment of CVD.

Provided herein in certain embodiments are methods of treating dyslipidemia in a subject in need thereof by administering a therapeutically effective amount of one or more sPLA$_2$ inhibitors and a therapeutically effective amount of one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001, and in certain of these embodiments the pharmaceutically acceptable prodrug is A-002. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, and pitavastatin, and the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain of these embodiments, the one or more compounds used in the treatment of CVD comprise ezetimibe. In certain embodiments, administration of one or more sPLA$_2$ inhibitors and one or more statins results in a decrease in cholesterol levels, and in certain of these embodiments the decrease in cholesterol levels is greater than that observed following administration of one or more sPLA$_2$ inhibitors or one or more statins alone. In certain of these embodiments, the decrease in cholesterol levels is synergistic, meaning that the decrease is greater than the expected additive effect of one or more sPLA$_2$ inhibitors and one or more statins. In certain of these embodiments, administration of one or more sPLA$_2$ inhibitors and one or more statins results in an improved HDL/LDL ratio, either by decreasing LDL levels, increasing HDL levels, or both.

Provided herein in certain embodiments are methods of treating CVD or conditions associated with CVD in a subject in need thereof by administering a therapeutically effective amount of one or more sPLA$_2$ inhibitors and a therapeutically effective amount of one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001, and in certain of these embodiments, the pharmaceutically acceptable prodrug is A-002. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, and pitavastatin, and the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain of these embodiments, the one or more compounds used in the treatment of CVD comprise ezetimibe. In certain embodiments, treatment of CVD or a condition associated with CVD may be associated with a decrease in cholesterol levels. In other embodiments, however, treatment of certain forms of CVD may not be associated with a concomitant decrease in cholesterol levels. For example, sPLA$_2$ inhibitor and statin administration may result in a decrease in atherosclerotic plaque formation without a measurable decrease in cholesterol levels via a mechanism such as inhibition of inflammation. In these embodiments, treatment of CVD may be associated with a decrease in levels of one or more inflammatory markers, such as for example sPLA$_2$, CRP, and/or IL-6. In certain embodiments, administration of a combination of one or more sPLA$_2$ inhibitors and one or more statins results in a greater degree of treatment than that observed following administration of one or more sPLA$_2$ inhibitors or statins alone. In certain of these embodiments, the degree of treatment is synergistic, meaning that the degree of treatment is greater than the expected additive effect of one or more sPLA$_2$ inhibitors and one or more statins.

Provided herein in certain embodiments are methods for increasing the effectiveness of a compound used in the treatment of CVD by administering one or more sPLA$_2$ inhibitors in conjunction with the compound used in the treatment of CVD. In certain embodiments, the one or more sPLA$_2$ inhibitors comprise A-001 or a pharmaceutically acceptable prodrug, salt, polymorph, co-crystal, or solvate of A-001, and in certain of these embodiments, the pharmaceutically acceptable prodrug is A-002. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, and pitavastatin, and the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain of these embodiments, the one or more compounds used in the treatment of CVD comprise ezetimibe. An increase in effectiveness of a compound used in the treatment of CVD as used herein refers to an increase the therapeutic effect of the compound, a decrease in the dosage of the compound required to obtain a particular level of therapeutic effect, or some combination thereof. For example, an increase in effectiveness of a statin as used herein may refer to a greater decrease in LDL levels following administration of a particular dosage of a statin, a decrease in the dosage of statin required to bring about a particular decrease in LDL levels, or some combination thereof.

Likewise, in certain embodiments methods are provided for increasing the effectiveness of an sPLA$_2$ inhibitor by administering one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001, and in certain of these embodiments, the pharmaceutically acceptable prodrug is A-002. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, and pitavastatin, and the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain of these embodiments, the one or more compounds used in the treatment of CVD comprise ezetimibe.

In certain embodiments, one or more sPLA$_2$ inhibitors and one or more compounds used in the treatment of CVD, such as for example one or more statins, may be administered to a subject separately, i.e., as separate compositions. In these embodiments, the one or more sPLA$_2$ inhibitors and the one or more compounds used in the treatment of CVD may be administered simultaneously or sequentially. Further, the one or more sPLA$_2$ inhibitors and the one or more compounds used in the treatment of CVD may be administered at different times, and one compound may be administered more frequently than another. In certain embodiments wherein the one or more compounds used in the treatment of CVD are statins and wherein the sPLA$_2$ inhibitors and/or statins are given in multiple administrations, one or both may be administered anywhere from once or more times per day to once every week, once every month, or once every several months. In certain preferred embodiments, the one or more sPLA$_2$ inhibitors and/or statins may be administered twice a day, and in other preferred embodiments the one or more sPLA$_2$ inhibitors and/or statins may be administered once a day.

In certain embodiments, kits are provided that comprise one or more sPLA$_2$ inhibitors and one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001, and in certain of these embodiments, the pharmaceutically acceptable prodrug is A-002. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, and pitavastatin, and the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. Within the kit, the one or more sPLA$_2$ inhibitors and one or more compounds used in the treatment of CVD may be divided into separate compartments. For example, the kit may comprise multiple bottles or packets, wherein each bottle or packet contains either one or more sPLA$_2$ inhibitors or one or more compounds used in the treatment of CVD. In other embodiments, the one or more sPLA$_2$ inhibitors and one or more compounds used in the treatment of CVD may be found in a single, undivided container. In certain embodiments, the kit provides instructions for usage, such as dosage or administration instructions.

Provided herein in certain embodiments are pharmaceutical compositions comprising a therapeutically effective amount of one or more sPLA$_2$ inhibitors and a therapeutically effective amount of one or more compounds used in the treatment of CVD. In certain embodiments, the one or more sPLA$_2$ inhibitors comprise A-001 or a pharmaceutically acceptable prodrug, salt, polymorph, co-crystal, or solvate of A-001, and in certain of these embodiments, the pharmaceutically acceptable prodrug is A-002. In certain embodiments, the one or more compounds used in the treatment of CVD comprise one or more statins or statin combination drugs. In certain of these embodiments, the one or more statins are selected from the group consisting of atorvastatin, simvastatin, rosuvastatin, lovastatin, pravastatin, cerivastatin, fluvastatin, mevastatin, and pitavastatin, and the statin combination drugs are selected from the group consisting of atorvastatin plus ezetimibe, atorvastatin plus amlodipine, atorvastatin plus CP-529414, atorvastatin plus APA-01, simvastatin plus ezetimibe, simvastatin plus extended release niacin, simvastatin plus MK-0524A, lovastatin plus extended release niacin, rosuvastatin plus fenofibrate, pravastatin plus fenofibrate, and statin plus TAK-457. In certain embodiments, the one or more compounds used in the treatment of CVD comprise one or more non-statin compounds selected from the group consisting of bile acid sequestrants, fibrates, niacin or niacin derivatives, cholesterol absorption inhibitors, cholesteryl ester transfer protein (CETP) inhibitors, microsomal triglyceride transfer protein (MTP) inhibitors, squalene synthase inhibitors, ACE inhibitors, angiotensin II receptor antagonists, beta-adrenergic blockers, calcium channel blockers, and antithrombotics. In certain of these embodiments, the one or more compounds used in the treatment of CVD comprise ezetimibe.

Pharmaceutical compositions comprising one or more sPLA$_2$ inhibitors and one or more compounds used in the treatment of CVD, such as for example one or more statins, may be administered to a subject on a one-time basis or in multiple administrations. In those embodiments wherein the compositions are given in multiple administrations, they may be administered at set intervals over a particular time period determined in advance, or they may be administered indefinitely or until a particular therapeutic benchmark is reached, such as for example until a subject exhibits cholesterol levels, triglyceride levels, or inflammatory marker levels that are below a specified threshold. In certain embodiments, the compositions may be administered from once or more times per day to once every month or once every several months. In certain of these embodiments, the compositions are administered once or twice per day.

Pharmaceutical compositions comprising one or more sPLA$_2$ inhibitors, one or more compounds used in the treatment of CVD, or one or more sPLA$_2$ inhibitors plus one or more compounds used in the treatment of CVD as disclosed herein may be delivered to a subject by any administration pathway known in the art, including but not limited to oral, aerosol, enteral, nasal, ophthalmic, parenteral, or transdermal (e.g., topical cream or ointment, patch). "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. sPLA$_2$ inhibitor, statin, or combined sPLA$_2$ inhibitor and statin pharmaceutical compositions as described herein may be administered in any pharmaceutically acceptable form, including for example in the form of a solid, liquid solution, suspension, emulsion, dispersion, micelle, or liposome. Preparations for injection may include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile emulsions. The solutions may be either aqueous or nonaqueous. In certain embodiments, the compositions may comprise one or more pharmaceutically acceptable carriers or may be administered in conjunction with one or more pharmaceutically acceptable carriers.

In certain embodiments, pharmaceutical compositions comprising one or more sPLA$_2$ inhibitors, one or more compounds used in the treatment of CVD, or one or more sPLA$_2$ inhibitors plus one or more compounds used in the treatment of CVD as described herein may be formed into oral dosage units, such as for example tablets, pills, or capsules. Such an oral dosage unit may comprise the active ingredients (e.g., A-002 and one or more statins) and one or more pharmaceutically acceptable carriers. As disclosed herein, the feasibility of such an oral dosage unit was demonstrated by producing a batch of tablets comprising A-002 and simvastatin as the active ingredients. Each tablet was formulated with 250 mg of A-002 and 40 mg of simvastatin. Pharmaceutically acceptable carriers utilized in formulating the tablets included anhydrous lactose, lactose fast flo, and microcrystalline cellulose as diluents, hydroxypropyl cellulose as a binder, croscarmellose sodium as a disintegrants, butylated hydroxyanisole as an antioxidant, magnesium stearate as a lubricant, and polysorbate 80 as a surfactant. Water was used as a solvent when formulating the tablet. The final tablets contained high concentrations of both active ingredients as determined by HPLC analysis, indicating that an $sPLA_2$ inhibitor and one or more compounds used in the treatment of CVD, such as for example one or more statins, may be formulated into a single oral dosage unit. The specific tablet formulation disclosed herein is provided as an example only. One of ordinary skill in the art will recognize that the therapeutically acceptable carriers utilized in the formulation may be varied, and that such variations are routine in the art. Likewise, the active ingredients may vary. As disclosed herein, administration of A-002 in combination with a variety of statins causes a synergistic decrease in serum lipid levels. Therefore, in certain embodiments, A-002 may be combined with any statin known in the art, including but not limited to atorvastatin or atorvastatin calcium, cerivastatin, fluvastatin, lovastatin, mevastatin, pitavastatin, pravastatin, rosuvastatin, and/or simvastatin. In certain embodiments, an oral dosage unit may comprise a coating that surrounds the active ingredients and pharmaceutically acceptable carrier(s).

In certain embodiments, pharmaceutical compositions comprising one or more $sPLA_2$ inhibitors, one or more compounds used in the treatment of CVD, or one or more $sPLA_2$ inhibitors plus one or more compounds used in the treatment of CVD as disclosed herein may be administered via a time release delivery vehicle, such as for example a time release oral dosage unit. A "time release vehicle" as used herein refers to any delivery vehicle that releases active agent (e.g., A-002 and one or more statins) at some time after administration or over a period of time following administration rather than immediately upon administration. Time release may be obtained by a coating on the vehicle that dissolves over a set timeframe following administration. In certain embodiments, the time release vehicle may comprise multiple layers of coating alternated with multiple layers of active ingredients, such that each layer of coating releases a certain volume of active ingredients as it dissolves. In other embodiments, $sPLA_2$ inhibitor, statin, or combined $sPLA_2$ inhibitor and statin pharmaceutical compositions may be administered via an immediate release delivery vehicle.

A therapeutically effective amount of an $sPLA_2$ inhibitor or a compound used in the treatment of CVD for use in the methods or compositions disclosed herein may be determined for each compound individually. For example, statins or statin combination drugs may be administered or included in a pharmaceutical composition at a dosage that is well known in the art to decrease cholesterol levels. One of skill in the art will recognize that in those embodiments wherein one or more compounds used in the treatment of CVD are combined with one or more $sPLA_2$ inhibitors in a single composition, the amount of the compound used in the treatment of CVD that constitutes a therapeutically effective amount may be different than the amount of the compound that constitutes a therapeutically effective amount of the compound when administered alone due to, for example, interactions between the compound and the one or more $sPLA_2$ inhibitors. For example, the effective dosage of a statin for use in combination therapy may be lower than the standard dosage for the statin when administered alone. In this situation, one of skill in the art will be able to readily determine a therapeutically effective amount for the combination composition using methods well known in the art. In certain embodiments, a therapeutically effective amount of an $sPLA_2$ inhibitor for use alone or in combination with one or more compounds used in the treatment of CVD may be from about 5 to about 10,000 mg/dose. In certain of these embodiments, a therapeutically effective amount of an $sPLA_2$ inhibitor may be from about 25 to about 5,000 mg/dose, and in certain of these embodiments a therapeutically effective amount may be from about 50 to about 500 mg/dose.

In certain embodiments, an $sPLA_2$ inhibitor for use in the compositions and methods disclosed herein may be an indole-based $sPLA_2$ inhibitor, meaning that the compound contains an indole nucleus having the structure:

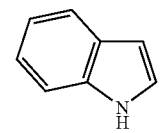

A variety of indole-based $sPLA_2$ inhibitors are known in the art. For example, indole-based $sPLA_2$ inhibitors that may be used in conjunction with the present invention include but are not limited to those set forth in U.S. Pat. Nos. 5,654,326 (Bach); 5,733,923 (Bach); 5,919,810 (Bach); 5,919,943 (Bach); 6,175,021 (Bach); 6,177,440 (Bach); 6,274,578 (Denney); and 6,433,001 (Bach), the entire disclosures of which are incorporated by reference herein. Methods of making indole-based $sPLA_2$ inhibitors are set forth in, for example, U.S. Pat. Nos. 5,986,106 (Khau); 6,265,591 (Anderson); and 6,380,397 (Anderson), the entire disclosures of which are incorporated by reference herein. $sPLA_2$ inhibitors for use in the present invention may be generated using these synthesis methods, or using any other synthesis method known in the art. In certain embodiments, $sPLA_2$ inhibitors for use in the present invention may be $sPLA_2$ type IIA, type V, and/or type X inhibitors. Various examples of indole-based $sPLA_2$ inhibitors are set forth below. These examples are merely provided as illustrations of the types of inhibitors that may be used in conjunction with the present invention, and as such are not meant to be limiting. One of ordinary skill in the art will recognize that a variety of other indole-based $sPLA_2$ inhibitors may be used.

In certain embodiments, $sPLA_2$ inhibitors for use in the current invention are 1H-indole-3-glyoxylamide compounds having the structure:

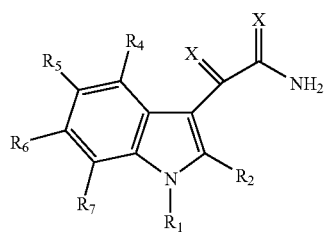

wherein:
each X is independently oxygen or sulfur;
$R_1$ is selected from the group consisting of (a), (b), and (c), wherein:
(a) is $C_7$-$C_{20}$ alkyl, $C_7$-$C_{20}$ alkenyl, $C_7$-$C_{20}$ alkynyl, carbocyclic radicals, or heterocyclic radicals;

(b) is a member of (a) substituted with one or more independently selected non-interfering substituents; and (c) is the group -(L)-$R_{80}$, where, -(L)- is a divalent linking group of 1 to 12 atoms selected from carbon, hydrogen, oxygen, nitrogen, and sulfur, wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) carbon, hydrogen, and oxygen only; and where $R_{80}$ is a group selected from (a) or (b);

$R_2$ is hydrogen, halo, $C_1$-$C_3$ alkyl, $C_3$-$C_4$ cycloalkyl, $C_3$-$C_4$ cycloalkenyl, —O—($C_1$-$C_2$ alkyl), —S—($C_1$-$C_2$ alkyl), or a non-interfering substituent having a total of 1 to 3 atoms other than hydrogen;

$R_4$ and $R_5$ are independently selected from the group consisting of hydrogen, a non-interfering substituent, and -($L_a$)-(acidic group), wherein -($L_a$)- is an acid linker having an acid linker length of 1 to 4; provided that at least one of $R_4$ and $R_5$ must be -($L_a$)-(acidic group);

$R_6$ and $R_7$ are each independently selected from hydrogen, non-interfering substituents, carbocyclic radicals, carbocyclic radicals substituted with non-interfering substituents, heterocyclic radicals, and heterocyclic radicals substituted with non-interfering substituents;

provided that for any of the groups $R_1$, $R_6$, and $R_7$, the carbocyclic radical is selected from the group consisting of cycloalkyl, cycloalkenyl, phenyl, naphthyl, norbornanyl, bicycloheptadienyl, toluoyl, xylenyl, indenyl, stilbenzyl, terphenylyl, diphenylethylenyl, phenyl-cyclohexenly, acenaphthylenyl, and anthracenyl, biphenyl, bibenzylyl and related bibenzylyl homologues represented by the formula (bb),

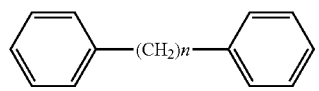

(bb)

where n is a number from 1 to 8; provided, that for any of the groups $R_1$, $R_6$, and $R_7$, the heterocyclic radical is selected from the group consisting of pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1.2-A)pyridinyl, benzotriazolyl, anthranilyl, 1,2-benzisoxazolyl, benzoxazolyl, benzotriazolyl, purinyl, pryidinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl; and provided that for the groups $R_1$, $R_2$, $R_4$, $R_5$, $R_6$, and $R_7$ the non-interfering substituent is selected from the group consisting of $C_1$-$C_6$ alkyl, $C_2$-$C_6$ alkenyl, $C_2$-$C_6$ alkynyl, $C_7$-$C_{12}$ aralkyl, $C_7$-$C_{12}$ alkaryl, $C_3$-$C_8$ cycloalkyl, $C_3$-$C_8$ cycloalkenyl, phenyl, toluoyl, xylenyl, biphenyl, $C_1$-$C_6$ alkoxy, $C_2$-$C_6$ alkenyloxy, $C_2$-$C_6$ alkynyloxy, $C_2$-$C_{12}$ alkoxyalkyl, $C_2$-$C_{12}$ alkoxyalkyloxy, $C_2$-$C_{12}$ alkylcarbonyl, $C_2$-$C_{12}$ alkylcarbonylamino, $C_2$-$C_{12}$ alkoxyamino, $C_2$-$C_{12}$ alkoxyaminocarbonyl, $C_2$-$C_{12}$ alkylamino, $C_1$-$C_6$ alkylthio, $C_2$-$C_{12}$ alkylthiocarbonyl, $C_1$-$C_6$ alkylsulfinyl, $C_1$-$C_6$ alkylsulfonyl, $C_2$-$C_6$ haloalkoxy, $C_1$-$C_6$ haloalkylsulfonyl, $C_2$-$C_6$ haloalkyl, $C_1$-$C_6$ hydroxyalkyl, —C(O)O($C_1$-$C_6$ alkyl), —($CH_2$)$_n$—O—($C_1$-$C_6$ alkyl), benzyloxy, phenoxy, phenylthio, —(CONHSO$_2$R), —CHO, amino, amidino, bromo, carbamyl, carboxyl, carbalkoxy, —($CH_2$)$_n$—$CO_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$-$C_6$ carbonyl, where n is from 1 to 8; and pharmaceutically acceptable salts, solvates, prodrug derivatives, racemates, tautomers, or optical isomers thereof.

In certain of these embodiments, -(L)- has the formula:

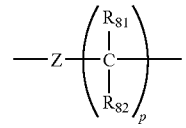

wherein $R_{81}$ and $R_{82}$ are each independently selected from the group consisting of hydrogen, $C_1$-$C_{10}$ alkyl, carboxy, carbalkoxy, and halo; p is a number from 1 to 5; and Z is selected from the group consisting of a bond, —(CH$_2$)—, —O—, —N($C_1$-$C_{10}$ alkyl)-, —NH—, and —S—.

In certain of these embodiments wherein $R_4$ is -($L_a$)-(acidic group), the acid linker -($L_a$)- has the formula:

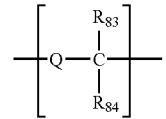

wherein Q is selected from the group consisting of —(CH$_2$)—, —O—, —NH—, and —S—; and $R_{83}$ and $R_{84}$ are each independently selected from the group consisting of hydrogen, $C_1$-$C_{10}$ alkyl, aryl, $C_1$-$C_{10}$ alkaryl, $C_1$-$C_{10}$ aralkyl, hydroxy, and halo.

In certain of these embodiments wherein $R_5$ is -($L_a$)-(acidic group), the acid linker -($L_a$)- has the formula:

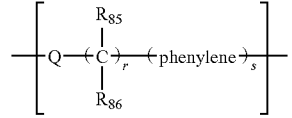

wherein r is a number from 2 to 7; s is 0 or 1; Q is selected from the group consisting of —(CH$_2$)—, —O—, —NH—, and —S—; and $R_{85}$ and $R_{86}$ are each independently selected from the group consisting of hydrogen, $C_1$-$C_{10}$ alkyl, aryl, $C_1$-$C_{10}$ alkaryl, $C_1$-$C_{10}$ aralkyl, carboxy, carbalkoxy, and halo.

In certain embodiments, a 1H-indole-3-glyoxylamide compound for use in the present invention is selected from the group consisting of: ((3-(2-Amino-1,2-dioxoethyl)-2-ethyl-1-(phenylmethyl)-1H-indol-4-yl)oxy)acetic acid; [[3-(2-Amino-1,2-dioxoethyl)-2-ethyl-1-(phenylmethyl)-1H-indol-4-yl]oxy]acetic acid methyl ester; ((3-(2-Amino-1,2-dioxoethyl)-2-methyl-1-(phenylmethyl)-1H-indol-4-yl)oxy) acetic acid; dl-2-((3-(2-Amino-1,2-dioxoethyl)-2-methyl-1-(phenylmethyl)-1H-indol-4-yl) oxy)propanoic acid; ((3-(2-Amino-1,2-dioxoethyl)-1-((1,1'-biphenyl)-2-ylmethyl)-2-methyl-1H-indol-4-yl)oxy)acetic acid; ((3-(2-Amino-1,2-dioxoethyl)-1-((1,1'-biphenyl)-3-ylmethyl)-2-methyl-1H-indol-4-yl)oxy)acetic acid; ((3-(2-Amino-1,2-dioxoethyl)-1-((1,1'-biphenyl)-4-ylmethyl)-2-methyl-1H-indol-4-yl)oxy) acetic acid; ((3-(2-Amino-1,2-dioxoethyl)-1-((2,6-dichlorophenyl)methyl)-2-methyl-1H-indol-4-yl)oxy)acetic acid; ((3-(2-Amino-1,2-dioxoethyl)-1-(4(-fluorophenyl)methyl)-2-methyl-1H-indol-4-yl)oxy)acetic acid; ((3-(2-

Amino-1,2-dioxoethyl)-2-methyl-1-((1-naphthalenyl)methyl)-1H-indol-4-yl)oxy)acetic acid; ((3-(2-Amino-1,2-dioxoethyl)-1-((3-chlorophenyl)methyl)-2-ethyl-1H-indol-4-yl)oxy)acetic acid; ((3-(2-Amino-1,2-dioxoethyl)-1-((1,1'-biphenyl)-2-ylmethyl)-2-ethyl-1H-indol-4-yl)oxy)acetic acid; ((3-(2-amino-1,2-dioxoethyl)-1-((1,1'-biphenyl)-2-ylmethyl)-2-propyl-1H-indol-4-yl)oxy)acetic acid; ((3-(2-Amino-1,2-dioxoethyl)-2-cyclopropyl-1-(phenylmethyl)-1H-indol-4-yl)oxy)acetic acid; ((3-(2-Amino-1,2-dioxoethyl)-1-((1,1'-biphenyl)-2-ylmethyl)-2-cyclopropyl-1H-indol-4-yl)oxy)acetic acid; and 4-((3-(2-Amino-1,2-dioxoethyl)-2-ethyl-1-(phenylmethyl)-1H-indol-5-yl)oxy) butanoic acid, or pharmaceutically acceptable salts, solvates, prodrug derivatives, racemates, tautomers, or optical isomers thereof.

In certain embodiments, sPLA$_2$ inhibitors for use in the current invention are 1H-indole-3-glyoxylamide compounds having the structure:

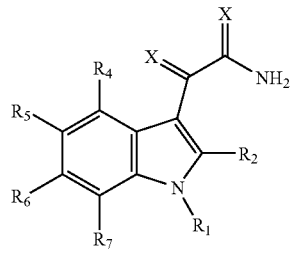

wherein:

both X are oxygen;

$R_1$ is selected from the group consisting of:

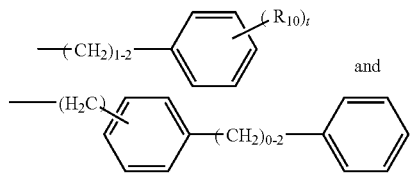

wherein $R_{10}$ is a radical independently selected from halo, $C_1$-$C_{10}$ alkoxy, —S—($C_1$-$C_{10}$ alkyl), and $C_1$-$C_{10}$ haloalkyl, and t is a number from 0 to 5;

$R_2$ is selected from the group consisting of halo, cyclopropyl, methyl, ethyl, and propyl;

$R_4$ and $R_5$ are independently selected from the group consisting of hydrogen, a non-interfering substituent, and -($L_a$)-(acidic group), wherein -($L_a$)- is an acid linker; provided that the acid linker -($L_a$)- for $R_4$ is selected from the group consisting of:

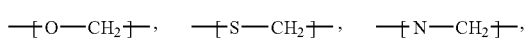

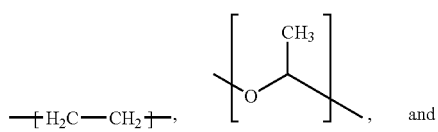

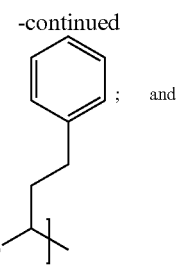

provided that the acid linker -($L_a$)- for $R_5$ is selected from the group consisting of:

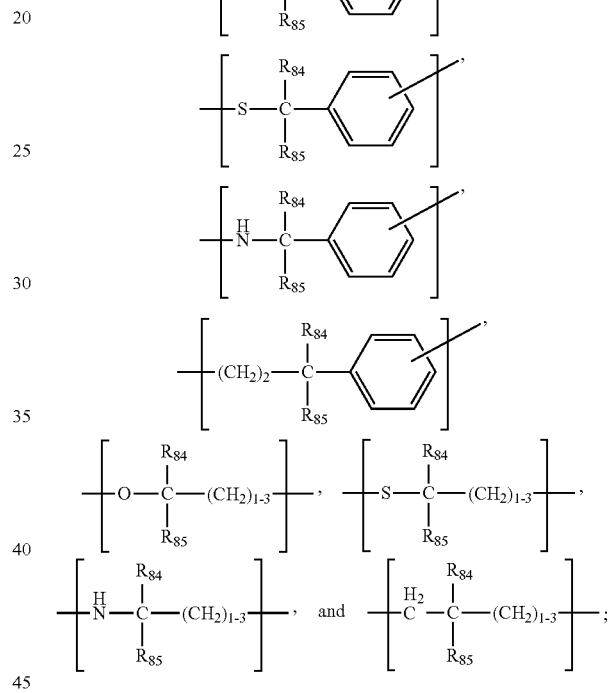

wherein $R_{84}$ and $R_{85}$ are each independently selected from the group consisting of hydrogen, $C_1$-$C_{10}$ alkyl, aryl, $C_1$-$C_{10}$ alkaryl, $C_1$-$C_{10}$ aralkyl, carboxy, carbalkoxy, and halo; provided that at least one of $R_4$ and $R_5$ must be -($L_a$)-(acidic group), and (acidic group) on -($L_a$)-(acidic group) of $R_4$ or $R_5$ is selected from —CO$_2$H, —SO$_3$H, or —P(O)(OH)$_2$;

$R_6$ and $R_7$ are each independently selected from the group consisting of hydrogen and non-interfering substituents, with the non-interfering substituents being selected from the group consisting of: $C_1$-$C_6$ alkyl, $C_2$-$C_6$ alkenyl, $C_2$-$C_6$ alkynyl, $C_7$-$C_{12}$ aralkyl, $C_7$-$C_{12}$ alkaryl, $C_3$-$C_8$ cycloalkyl, $C_3$-$C_8$ cycloalkenyl, phenyl, toluoyl, xylenyl, biphenyl, $C_1$-$C_6$ alkoxy, $C_2$-$C_6$ alkenyloxy, $C_2$-$C_6$ alkynyloxy, $C_2$-$C_{12}$ alkoxyalkyl, $C_2$-$C_{12}$ alkoxyalkyloxy, $C_2$-$C_{12}$ alkylcarbonyl, $C_2$-$C_{12}$ alkylcarbonylamino, $C_2$-$C_{12}$ alkoxyamino, $C_2$-$C_{12}$ alkoxyaminocarbonyl, $C_2$-$C_{12}$ alkylamino, $C_1$-$C_6$ alkylthio, $C_2$-$C_{12}$ alkylthiocarbonyl, $C_1$-$C_6$ alkylsulfinyl, $C_1$-$C_6$ alkylsulfonyl, $C_2$-$C_6$ haloalkoxy, $C_1$-$C_6$ haloalkylsulfonyl, $C_2$-$C_6$ haloalkyl, $C_1$-$C_6$ hydroxyalkyl, —C(O)O($C_1$-$C_6$ alkyl), —(CH$_2$)$_n$—O—($C_1$-$C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$-C$_6$ carbonyl; wherein n is from 1 to 8;

and pharmaceutically acceptable salts, solvates, prodrug derivatives, racemates, tautomers, or optical isomers thereof.

In certain embodiments, 1H-indole-3-glyoxylamide compounds for use in the present invention are selected from the group consisting of: ((3-(2-Amino-1,2-dioxoethyl)-2-methyl-1-(phenylmethyl)-1H-indol-4-yl)oxy)acetic acid; ((3-(2-Amino-1,2-dioxoethyl)-2-methyl-1-(phenylmethyl)-1H-indol-4-yl)oxy)acetic acid methyl ester; dl-2-((3-(2-Amino-1,2-dioxoethyl)-2-methyl-1-(phenylmethyl)-1H-indol-4-yl)oxy)propanoic acid; dl-2-((3-(2-Amino-1,2-dioxoethyl)-2-methyl-1-(phenylmethyl)-1H-indol-4-yl)oxy)propanoic acid methyl ester; ((3-(2-Amino-1,2-dioxoethyl)-1-((1,1'-biphenyl)-2-ylmethyl)-2-methyl-1H-indol-4-yl)oxy)acetic acid; ((3-(2-Amino-2-dioxoethyl)-1-((1,1'-biphenyl)-2-ylmethyl)-2-methyl-1H-indol-4-yl)oxy)acetic acid methyl ester; ((3-(2-Amino-1,2-dioxoethyl)-1-((1,1'-biphenyl)-3-ylmethyl)-2-methyl-1H-indol-4-yl)oxy)acetic acid; ((3-(2-Amino-1,2-dioxoethyl)-1-((1,1'-biphenyl)-3-ylmethyl)-2-methyl-1H-indol-4-yl)oxy)acetic acid methyl ester; ((3-(2-Amino-1,2-dioxoethyl)-1-((1,1'-biphenyl)-4-ylmethyl)-2-methyl-1H-indol-4-yl)oxy)acetic acid; ((3-(2-Amino-1,2-dioxoethyl)-1-((1,1'-biphenyl)-4-ylmethyl)-2-methyl-1H-indol-4-yl)oxy)acetic acid methyl ester; ((3-(2-Amino-1,2-dioxoethyl)-1-((2,6-dichlorophenyl)methyl)-2-methyl-1H-indol-4-yl)oxy)acetic acid; ((3-(2-Amino-1,2-dioxoethyl)-1-((2,6-dichlorophenyl)methyl)-2-methyl-1H-indol-4-yl)oxy)acetic acid methyl ester; ((3-(2-Amino-1,2-dioxoethyl)-1-(4 (-fluorophenyl)methyl)-2-methyl-1H-indol-4-yl)oxy)acetic acid; ((3-(2-Amino-1,2-dioxoethyl))-1-(4(-fluorophenyl)methyl)-2-methyl-1H-indol-4-yl)oxy)acetic acid methyl ester; ((3-(2-Amino-1,2-dioxoethyl)-2-methyl-1-((1-naphthalenyl)methyl)-1H-indol-4-yl)oxy)acetic acid; ((3-(2-Amino-1,2-dioxoethyl)-2-methyl-1-((1-naphthalenyl)methyl)-1H-indol-4-yl)oxy)acetic acid methyl ester; ((3-(2-Amino-1,2-dioxoethyl)-1-((3-chlorophenyl)methyl)-2-ethyl-1H-indol-4-yl)oxy)acetic acid; ((3-(2-Amino-1,2-dioxoethyl)-1-((3-chlorophenyl)methyl)-2-ethyl-1H-indol-4-yl)oxy)acetic acid methyl ester; ((3-(2-Amino-1,2-dioxoethyl)-1-((1,1'-biphenyl)-2-ylmethyl)-2-ethyl-1H-indol-4-yl)oxy)acetic acid; ((3-(2-Amino-1,2-dioxoethyl)-1-((1,1'-biphenyl)-2-ylmethyl)-2-ethyl-1H-indol-4-yl)oxy) acetic acid methyl ester; ((3-(2-amino-1,2-dioxoethyl)-1-((1,1'-biphenyl)-2-ylmethyl)-2-propyl-1H-indol-4-yl)oxy) acetic acid; ((3-(2-amino-1,2-dioxoethyl)-1-((1,1'-biphenyl)-2-ylmethyl)-2-propyl-1H-indol-4-yl)oxy)acetic acid methyl ester; ((3-(2-Amino-1,2-dioxoethyl)-2-cyclopropyl-1-(phenylmethyl)-1H-indol-4-yl)oxy)acetic acid; ((3-(2-Amino-1,2-dioxoethyl)-2-cyclopropyl-1-(phenylmethyl)-1H-indol-4-yl)oxy)acetic acid methyl ester; ((3-(2-Amino-1,2-dioxoethyl)-1-((1,1'-biphenyl)-2-ylmethyl)-2-cyclopropyl-1H-indol-4-yl)oxy)acetic acid; ((3-(2-Amino-1,2-dioxoethyl)-1-((1,1'-biphenyl)-2-ylmethyl)-2-cyclopropyl-1H-indol-4-yl)oxy)acetic acid methyl ester; 4-((3-(2-Amino-1,2-dioxoethyl)-2-ethyl-1-(phenylmethyl)-1H-indol-5-yl)oxy)butanoic acid; 4-((3-(2-Amino-1,2-dioxoethyl)-2-ethyl-1-(phenylmethyl)-1H-indol-5-yl)oxy) butanoic acid tert-butyl ester, or pharmaceutically acceptable salts, solvates, prodrug derivatives, racemates, tautomers, or optical isomers thereof.

In certain embodiments, sPLA$_2$ inhibitors for use in the current invention are 1H-indole-3-glyoxylamide compounds having the structure:

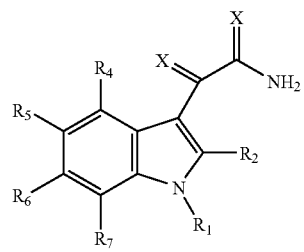

wherein:

each X is independently oxygen or sulfur;

R$_1$ is selected from groups (a), (b), and (c) wherein:

(a) is C$_7$-C$_{20}$ alkyl, C$_7$-C$_{20}$ alkenyl, C$_7$-C$_{20}$ alkynyl, carbocyclic radical, or heterocyclic radical;

(b) is a member of (a) substituted with one or more independently selected non-interfering substituents; and (c) is the group -(L)-R$_{80}$, wherein -(L)- is a divalent linking group of 1 to 12 atoms selected from carbon, hydrogen, oxygen, nitrogen, and sulfur;

wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where R$_{80}$ is a group selected from (a) or (b);

R$_2$ is selected from the group consisting of hydrogen, halo, C$_1$-C$_3$ alkyl, C$_3$-C$_4$ cycloalkyl, C$_3$-C$_4$ cycloalkenyl, —O—(C$_1$-C$_2$ alkyl), —S—(C$_1$-C$_2$ alkyl), and a non-interfering substituent having a total of 1 to 3 atoms other than hydrogen;

R$_4$ and R$_5$ are independently selected from the group consisting of hydrogen, a non-interfering substituent, and the group -(L$_a$)-(acidic group), wherein -(L$_a$)- is an acid linker having an acid linker length of 1 to 4; provided that at least one of R$_4$ and R$_5$ is -(L$_a$)-(acidic group);

R$_6$ and R$_7$ are each independently selected from the group consisting of hydrogen, non-interfering substituents, carbocyclic radicals, carbocyclic radicals substituted with non-interfering substituents, heterocyclic radicals, and heterocyclic radicals substituted with non-interfering substituents;

and pharmaceutically acceptable salts, solvates, prodrug derivatives, racemates, tautomers, or optical isomers thereof.

In certain embodiments, sPLA$_2$ inhibitors for use in the current invention are methyl ester prodrug derivatives of 1H-indole-3-glyoxylamide compounds having the structure:

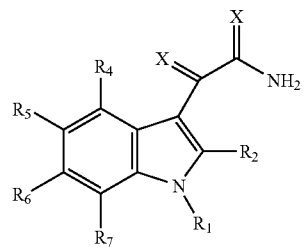

wherein:
both X are oxygen;
$R_1$ is selected from the group consisting of:

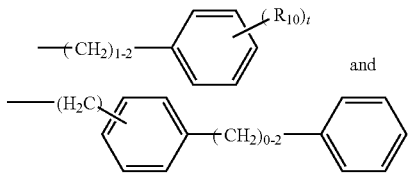
and wherein $R_{10}$ is a radical independently selected from halo, $C_1$-$C_{10}$ alkyl, $C_1$-$C_{10}$ alkoxy, —S—($C_1$-$C_{10}$ alkyl), and $C_1$-$C_{10}$ haloalkyl, and t is a number from 0 to 5;

$R_2$ is selected from the group consisting of halo, cyclopropyl, methyl, ethyl, and propyl;

$R_4$ and $R_5$ are independently selected from the group consisting of hydrogen, a non-interfering substituent, and -($L_a$)-(acidic group), wherein -($L_a$)- is an acid linker; provided that the acid linker -($L_a$)- for $R_4$ is selected from the group consisting of:

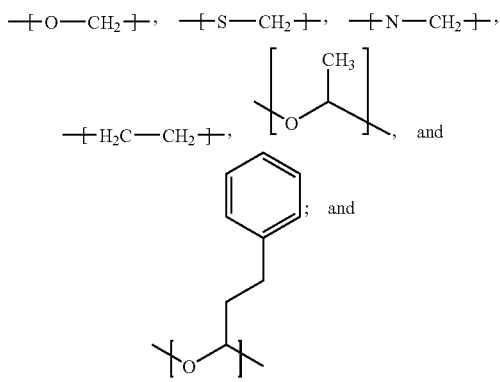

provided that the acid linker -($L_a$)- for $R_5$ is selected from the group consisting of:

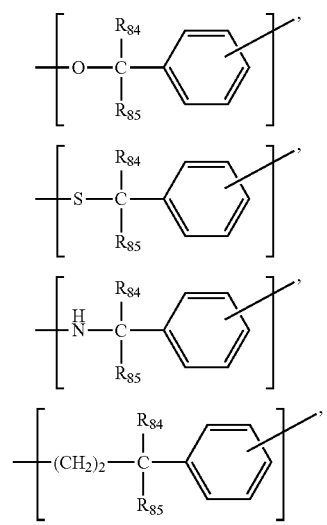

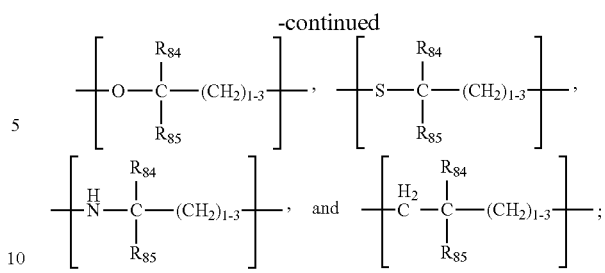

wherein $R_{84}$ and $R_{85}$ are each independently selected from the group consisting of hydrogen, $C_1$-$C_{10}$ alkyl, aryl, $C_1$-$C_{10}$ alkaryl, $C_1$-$C_{10}$ aralkyl, carboxy, carbalkoxy, and halo; provided that at least one of $R_4$ and $R_5$ must be -($L_a$)-(acidic group), and (acidic group) on -($L_a$)-(acidic group) of $R_4$ or $R_5$ is selected from —$CO_2H$, —$SO_3H$, or —$P(O)(OH)_2$;

$R_6$ and $R_7$ are each independently selected from the group consisting of hydrogen and non-interfering substituents, with the non-interfering substituents being selected from the group consisting of: $C_1$-$C_6$ alkyl, $C_2$-$C_6$ alkenyl, $C_2$-$C_6$ alkynyl, $C_7$-$C_{12}$ aralkyl, $C_7$-$C_{12}$ alkaryl, $C_3$-$C_8$ cycloalkyl, $C_3$-$C_8$ cycloalkenyl, phenyl, toluoyl, xylenyl, biphenyl, $C_1$-$C_6$ alkoxy, $C_2$-$C_6$ alkenyloxy, $C_2$-$C_6$ alkynyloxy, $C_2$-$C_{12}$ alkoxyalkyl, $C_2$-$C_{12}$ alkoxyalkyloxy, $C_2$-$C_{12}$ alkylcarbonyl, $C_2$-$C_{12}$ alkylcarbonylamino, $C_2$-$C_{12}$ alkoxyamino, $C_2$-$C_{12}$ alkoxyaminocarbonyl, $C_2$-$C_{12}$ alkylamino, $C_1$-$C_6$ alkylthio, $C_2$-$C_{12}$ alkylthiocarbonyl, $C_1$-$C_6$ alkylsulfinyl, $C_1$-$C_6$ alkylsulfonyl, $C_2$-$C_6$ haloalkoxy, $C_1$-$C_6$ haloalkylsulfonyl, $C_2$-$C_6$ haloalkyl, $C_1$-$C_6$ hydroxyalkyl, —C(O)O($C_1$-$C_6$ alkyl), —$(CH_2)_n$—O—($C_1$-$C_6$ alkyl), benzyloxy, phenoxy, phenylthio, —$(CONHSO_2R)$, —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$-$C_6$ carbonyl; wherein n is from 1 to 8;
and pharmaceutically acceptable salts, solvates, prodrug derivatives, racemates, tautomers, or optical isomers thereof.

In certain embodiments, sPLA$_2$ inhibitors for use in the current invention are (acyloxy) alkyl ester prodrug derivatives of 1H-indole-3-glyoxylamide compounds having the structure:

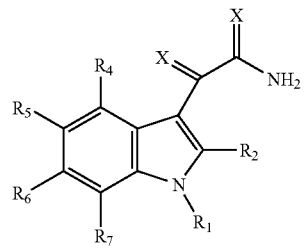

wherein:
both X are oxygen;
$R_1$ is selected from the group consisting of:

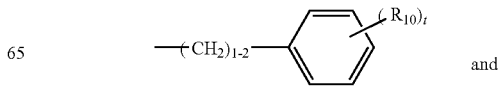
and

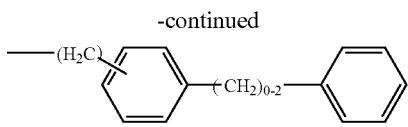

wherein $R_{10}$ is a radical independently selected from halo, $C_1$-$C_{10}$ alkyl, $C_1$-$C_{10}$ alkoxy, —S—($C_1$-$C_{10}$ alkyl), and $C_1$-$C_{10}$ haloalkyl, and t is a number from 0 to 5;

$R_2$ is selected from the group consisting of halo, cyclopropyl, methyl, ethyl, and propyl;

$R_4$ and $R_5$ are independently selected from the group consisting of hydrogen, a non-interfering substituent, and -($L_a$)-(acidic group), wherein -($L_a$)- is an acid linker; provided that the acid linker -($L_a$)- for $R_4$ is selected from the group consisting of:

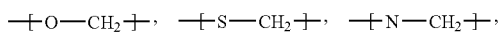

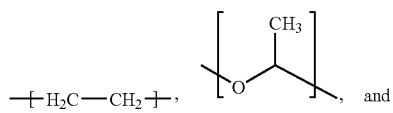

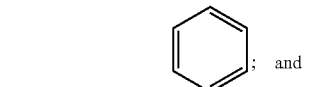

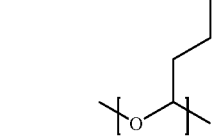

provided that the acid linker -($L_a$)- for $R_5$ is selected from the group consisting of:

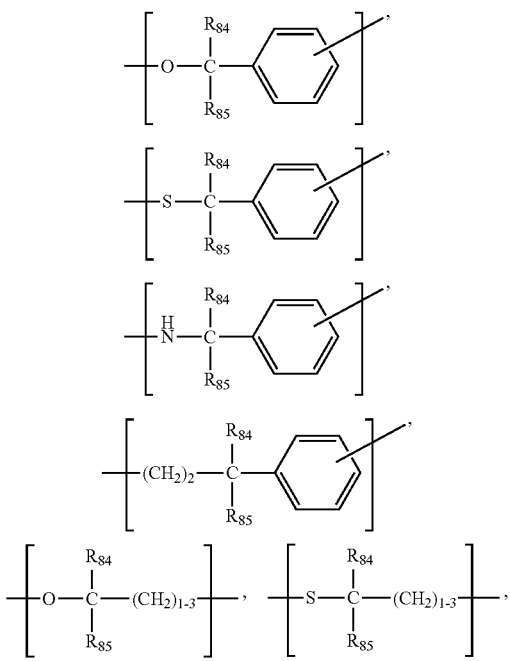

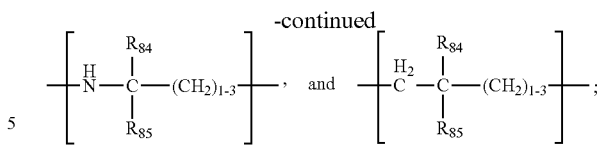

wherein $R_{84}$ and $R_{85}$ are each independently selected from the group consisting of hydrogen, $C_1$-$C_{10}$ alkyl, aryl, $C_1$-$C_{10}$ alkaryl, $C_1$-$C_{10}$ aralkyl, carboxy, carbalkoxy, and halo; provided that at least one of $R_4$ and $R_5$ must be -($L_a$)-(acidic group), and (acidic group) on -($L_a$)-(acidic group) of $R_4$ or $R_5$ is selected from —$CO_2H$, —$SO_3H$, or —$P(O)(OH)_2$;

$R_6$ and $R_7$ are each independently selected from the group consisting of hydrogen and non-interfering substituents, with the non-interfering substituents being selected from the group consisting of: $C_1$-$C_6$ alkyl, $C_2$-$C_6$ alkenyl, $C_2$-$C_6$ alkynyl, $C_7$-$C_{12}$ aralkyl, $C_7$-$C_{12}$ alkaryl, $C_3$-$C_8$ cycloalkyl, $C_3$-$C_8$ cycloalkenyl, phenyl, toluoyl, xylenyl, biphenyl, $C_1$-$C_6$ alkoxy, $C_2$-$C_6$ alkenyloxy, $C_2$-$C_6$ alkynyloxy, $C_2$-$C_{12}$ alkoxyalkyl, $C_2$-$C_{12}$ alkoxyalkyloxy, $C_2$-$C_{12}$ alkylcarbonyl, $C_2$-$C_{12}$ alkylcarbonylamino, $C_2$-$C_{12}$ alkoxyamino, $C_2$-$C_{12}$ alkoxyaminocarbonyl, $C_2$-$C_{12}$ alkylamino, $C_1$-$C_6$ alkylthio, $C_2$-$C_{12}$ alkylthiocarbonyl, $C_1$-$C_6$ alkylsulfinyl, $C_1$-$C_6$ alkylsulfonyl, $C_2$-$C_6$ haloalkoxy, $C_1$-$C_6$ haloalkylsulfonyl, $C_2$-$C_6$ haloalkyl, $C_1$-$C_6$ hydroxyalkyl, —C(O)O($C_1$-$C_6$ alkyl), —$(CH_2)_n$—O—($C_1$-$C_6$ alkyl), benzyloxy, phenoxy, phenylthio, —($CONHSO_2R$), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$-$C_6$ carbonyl; wherein n is from 1 to 8;

and pharmaceutically acceptable salts, solvates, prodrug derivatives, racemates, tautomers, or optical isomers thereof.

In certain embodiments, sPLA$_2$ inhibitors for use in the current invention are substituted tricyclics having the structure:

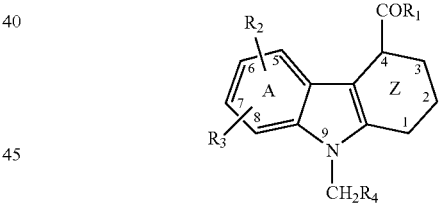

wherein:

$R_1$ is selected from the group consisting of —NHNH$_2$ and —NH$_2$;

$R_2$ is selected from the group consisting of —OH and —O(CH$_2$)$_m$R$_5$; wherein R$_5$ is selected from the group consisting of H, —CO$_2$H, —CO$_2$(C$_1$-C$_4$ alkyl), —SO$_3$H, —SO$_3$ (C$_1$-C$_4$ alkyl), tetrazolyl, —CN, —NH$_2$, —NHSO$_2$R$_{15}$, —CONHSO$_2$R$_{15}$, phenyl, phenyl substituted with —CO$_2$H or —CO$_2$(C$_1$-C$_4$)alkyl, and

wherein R$_6$ and R$_7$ are each independently selected from the group consisting of —OH, —O(C$_1$-C$_4$)alkyl; R$_{15}$ is selected from the group consisting of —(C$_1$-C$_6$)alkyl and —CF$_3$; and m is 1-3;

$R_3$ is selected from the group consisting of H, —O($C_1$-$C_4$)alkyl, halo, —($C_1$-$C_6$)alkyl, phenyl, —($C_1$-$C_4$)alkylphenyl, phenyl substituted with —($C_1$-$C_6$)alkyl, halo, or —$CF_3$, —$CH_2OSi$($C_1$-$C_6$)alkyl, furyl, thiophenyl, —($C_1$-$C_6$)hydroxyalkyl, and —($CH_2$)$_n$$R_8$; wherein $R_8$ is selected from the group consisting of H, —$CONH_2$, —$NR_9R_{10}$, —CN, and phenyl; wherein $R_9$ and $R_{10}$ are each independently —($C_1$-$C_4$)alkyl or -phenyl($C_1$-$C_4$)alkyl; and n is 1 to 8;

$R_4$ is selected from the group consisting of H, —($C_5$-$C_{14}$)alkyl, —($C_3$-$C_{14}$)cycloalkyl, pyridyl, phenyl, and phenyl substituted with —($C_1$-$C_6$)alkyl, halo, —$CF_3$, —$OCF_3$, —($C_1$-$C_4$)alkoxy, —CN, —($C_1$-$C_4$)alkylthio, phenyl($C_1$-$C_4$)alkyl, —($C_1$-$C_4$)alkylphenyl, phenyl, phenoxy, or naphthyl;

A is selected from the group consisting of phenyl and pyridyl wherein the nitrogen is at the 5-, 6-, 7-, or 8-position;

Z is selected from the group consisting of cyclohexenyl, phenyl, pyridyl wherein the nitrogen is at the 1-, 2-, or 3-position, and a 6-membered heterocyclic ring having one heteroatom selected from the group consisting of sulfur and oxygen at the 1-, 2-, or 3-position and nitrogen at the 1-, 2-, 3-, or 4- position, or wherein one carbon on the heterocyclic ring is optionally substituted with =O; and wherein one of A or Z is a heterocyclic ring;

and pharmaceutically acceptable salts, solvates, prodrug derivatives, racemates, tautomers, or optical isomers thereof.

In certain embodiments, sPLA$_2$ inhibitors for use in the current invention are substituted tricyclics having the structure:

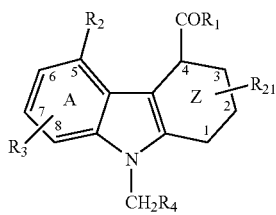

wherein:
Z is selected from the group consisting of cyclohexenyl and phenyl;
$R_{21}$ is a non-interfering substituent;
$R_1$ is —$NHNH_2$ or —$NH_2$;
$R_2$ is selected from the group consisting of —OH and —O($CH_2$)$_m$$R_5$; wherein $R_5$ is selected from the group consisting of H, —$CO_2H$, —$CONH_2$, —$CO_2$($C_1$-$C_4$ alkyl), —$SO_3H$, —$SO_3$($C_1$-$C_4$ alkyl), tetrazolyl, —CN, —$NH_2$, —$NHSO_2R_{15}$, —$CONHSO_2R_{15}$, phenyl, phenyl substituted with —$CO_2H$ or —$CO_2$($C_1$-$C_4$)alkyl, and

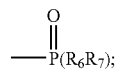

wherein $R_6$ and $R_7$ are each independently selected from the group consisting of —OH, —O($C_1$-$C_4$)alkyl; $R_{15}$ is selected from the group consisting of —($C_1$-$C_6$)alkyl and —$CF_3$; and m is 1-3;

$R_3$ selected from the group consisting of H, —O($C_1$-$C_4$)alkyl, halo, —($C_1$-$C_6$)alkyl, phenyl, —($C_1$-$C_4$)alkylphenyl, phenyl substituted with —($C_1$-$C_6$)alkyl, halo, or —$CF_3$, —$CH_2OSi$($C_1$-$C_6$)alkyl, furyl, thiophenyl, —($C_1$-$C_6$)hydroxyalkyl, and —($CH_2$)$_n$$R_8$; wherein $R_8$ is selected from the group consisting of H, —$CONH_2$, —$NR_9R_{10}$, —CN, and phenyl; $R_9$ and $R_{10}$ are each independently selected from the group consisting of H, —$CF_3$, phenyl, —($C_1$-$C_4$)alkyl, —($C_1$-$C_4$)alkylphenyl, and -phenyl($C_1$-$C_4$)alkyl; and n is 1 to 8;

$R_4$ is selected from the group consisting of H, —($C_5$-$C_{14}$)alkyl, —($C_3$-$C_{14}$)cycloalkyl, pyridyl, phenyl, phenyl substituted with —($C_1$-$C_6$)alkyl, halo, —$CF_3$, —$OCF_3$, —($C_1$-$C_4$)alkoxy, —CN, —($C_1$-$C_4$)alkylthio, -phenyl($C_1$-$C_4$)alkyl, —($C_1$-$C_4$)alkylphenyl, phenyl, phenoxy and naphthyl;

and pharmaceutically acceptable salts, solvates, prodrug derivatives, racemates, tautomers, or optical isomers thereof.

In certain embodiments, sPLA$_2$ inhibitors for use in the current invention are selected from the group consisting of: {9-[(phenyl)methyl]-5-carbamoylcarbazol-4-yl}oxyacetic acid; 9-benzyl-5,7-dimethoxy-1,2,3,4-tetrahydrocarbazole-4-carboxylic acid hydrazide; 9-benzyl-5,7-dimethoxy-1,2,3,4-tetrahydrocarbazole-4-carboxamide; [9-benzyl-4-carbamoyl-7-methoxy-1,2,3,4-tetrahydrocarbazol-5-yl]oxyacetic acid; [9-benzyl-4-carbamoyl-7-methoxycarbazol-5-yl]oxyacetic acid; methyl[9-benzyl-4-carbamoyl-7-methoxycarbazol-5-yl]oxyacetic acid; 9-benzyl-7-methoxy-5-cyanomethyloxy-1,2,3,4-tetrahydrocarbazole-4-carboxamide; 9-benzyl-7-methoxy-5-(1H-tetrazol-5-yl-methyl)oxy)-1,2,3,4-tetrahydrocarbazole-4-carboxamide; {9-[(phenyl)methyl]-5-carbamoyl-2-methyl-carbazol-4-yl}oxyacetic acid; {9-[(3-fluorophenyl)methyl]-5-carbamoyl-2-methylcarbazol-4-yl}oxyacetic acid; {9-[(3-methylphenyl)methyl]-5-carbamoyl-2-methylcarbazol-4-yl}oxyacetic acid; {9-[(phenyl)methyl]-5-carbamoyl-2-(4-trifluoromethylphenyl)-carbazol-4-yl}oxyacetic acid; 9-benzyl-5-(2-methanesulfonamido)ethyloxy-7-methoxy-1,2,3,4-tetrahydrocarbazole-4-carboxamide; 9-benzyl-4-(2-methanesulfonamido) ethyloxy-2-methoxycarbazole-5-carboxamide; 9-benzyl-4-(2-trifluoromethanesulfonamido) ethyloxy-2-methoxycarbazole-5-carboxamide; 9-benzyl-5-methanesulfonamidoylmethyloxy-7-methoxy-1,2,3,4-tetrahydrocarbazole-4-carboxamide; 9-benzyl-4-methanesulfonamidoylmethyloxy-carbazole-5-carboxamide; [5-carbamoyl-2-pentyl-9-(phenylmethyl)carbazol-4-yl]oxyacetic acid; [5-carbamoyl-2-(1-methylethyl)-9-(phenylmethyl)carbazol-4-yl]oxyacetic acid; [5-carbamoyl-9-(phenylmethyl)-2-[(tri(-1-methylethyl)silyl)oxymethyl]carbazol-4-yl]oxyacetic acid; [5-carbamoyl-2-phenyl-9-(phenylmethyl)carbazol-4-yl]oxyacetic acid; [5-carbamoyl-2-(4-chlorophenyl)-9-(phenylmethyl)carbazol-4-yl]oxyacetic acid; [5-carbamoyl-2-(2-furyl)-9-(phenylmethyl)carbazol-4-yl]oxyacetic acid; [5-carbamoyl-9-(phenylmethyl)-2-[(tri(-1-methylethyl)silyl)oxymethyl]carbazol-4-yl]oxyacetic acid; {9-[(2-Fluorophenyl)methyl]-5-carbamoylcarbazol-4-yl}oxyacetic acid; {9-[(2-trifluoromethylphenyl)methyl]-5-carbamoylcarbazol-4-yl}oxyacetic acid; {9-[(2-benzylphenyl)methyl]-5-carbamoylcarbazol-4-yl}oxyacetic acid; {9-[(1-naphthyl)methyl]-5-carbamoylcarbazol-4-yl}oxyacetic acid; {9-[(2-cyanophenyl)methyl]-5-carbamoylcarbazol-4-yl}oxyacetic acid; {9-[(3-cyanophenyl)methyl]-5-carbamoylcarbazol-4-yl}oxyacetic acid; {9-[(3,5-dimethylphenyl)methyl]-5-carbamoylcarbazol-4-yl}oxyacetic acid; {9-[(3-iodophenyl)methyl]-5-carbamoylcarbazol-4-yl}oxyacetic acid; {9-[(2-Chlorophenyl)methyl]-5-carbamoylcarbazol-4-yl}oxyacetic acid; {9-[(2,3-difluorophenyl)methyl]-5-carbamoylcarbazol-4-yl}oxyacetic acid; {9-[(2,6-difluorophenyl)methyl]-5-carbamoylcarbazol-4-yl}oxyacetic acid; {9-[(2,6-dichlorophenyl)methyl]-5-carbamoylcarbazol-4-yl}oxyacetic acid; {9-[(2-biphenyl)methyl]-5-carbamoylcarbazol-4-yl}oxyacetic acid; {9-[(2-Biphenyl)methyl]-5-carbamoylcarbazol-4-yl}oxyacetic acid methyl ester; [9-Benzyl-4-carbamoyl-1,2,3,4-tetrahydrocarbazol-5-yl]oxyacetic acid; {9-

[(2-Pyridyl)methyl]-5-carbamoylcarbazol-4-yl}oxyacetic acid; {9-[(3-Pyridyl)methyl]-5-carbamoylcarbazol-4-yl}oxyacetic acid; [9-benzyl-4-carbamoyl-8-methyl-1,2,3,4-tetrahydrocarbazol-5-yl]oxyacetic acid; [9-benzyl-5-carbamoyl-1-methylcarbazol-4-yl]oxyacetic acid; [9-benzyl-4-carbamoyl-8-fluoro-1,2,3,4-tetrahydrocarbazol-5-yl] oxyacetic acid; [9-benzyl-4-carbamoyl-8-chloro-1,2,3,4-tetrahydrocarbazol-5-yl]oxyacetic acid; [5-carbamoyl-9-(phenylmethyl)-2-[[(propen-3-yl)oxy]methyl]carbazol-4-yl]oxyacetic acid; [5-carbamoyl-9-(phenylmethyl)-2-[(propyloxy)methyl]carbazol-4-yl]oxyacetic acid; 9-benzyl-7-methoxy-5-((carboxamidomethyl)oxy)-1,2,3,4-tetrahydrocarbazole-4-carboxamide; 9-benzyl-7-methoxy-5-cyanomethyloxy-carbazole-4-carboxamide; 9-benzyl-7-methoxy-5-((1H-tetrazol-5-yl-methyl)oxy)-carbazole-4-carboxamide; 9-benzyl-7-methoxy-5-((carboxamidomethyl)oxy)-carbazole-4-carboxamide; [9-Benzyl-4-carbamoyl-1,2,3,4-tetrahydrocarbazole-5-yl]oxyacetic acid; {9-[(phenyl)methyl]-5-carbamoyl-2-methyl-carbazol-4-yl}oxyacetic acid; {9-[(3-fluorophenyl)methyl]-5-carbamoyl-2-methyl-carbazol-4-yl}oxyacetic acid; {9-[(3-methylphenyl)methyl]-5-carbamoyl-2-methylcarbazol-4-yl}oxyacetic acid; {9-[(phenyl)methyl]-5-carbamoyl-2-(4-trifluoromethylphenyl)-carbazol-4-yl}oxyacetic acid; 9-benzyl-5-(2-methanesulfonamido)ethyloxy-7-methoxy-1,2,3,4-tetrahydrocarbazole-4-carboxamide; 9-benzyl-4-(2-methanesulfonamido)ethyloxy-2-methoxycarbazole-5-carboxamide; 9-benzyl-4-(2-trifluoromethanesulfonamido)ethyloxy-2-methoxycarbazole-5-carboxamide; 9-benzyl-5-methanesulfonamidoylmethyloxy-7-methoxy-1,2,3,4-tetrahydrocarbazole-4-carboxamide; 9-benzyl-4-methanesulfonamidoylmethyloxy-carbazole-5-carboxamide; [5-carbamoyl-2-pentyl-9-(phenylmethyl) carbazol-4-yl]oxyacetic acid; [5-carbamoyl-2-(1-methylethyl)-9-(phenylmethyl)carbazol-4-yl]oxyacetic acid; [5-carbamoyl-9-(phenylmethyl)-2-[(tri-1-methylethyl)silyl]oxymethyl]carbazol-4-yl]oxyacetic acid; [5-carbamoyl-2-phenyl-9-(phenylmethyl)carbazol-4-yl]oxyacetic acid; [5-carbamoyl-2-(4-chlorophenyl)-9-(phenylmethyl)carbazol-4-yl]oxyacetic acid; [5-carbamoyl-2-(2-furyl)-9-(phenylmethyl)carbazol-4-yl]oxyacetic acid; [5-carbamoyl-9-(phenylmethyl)-2-[(tri(-1-methylethyl)silyl)oxymethyl] carbazol-4-yl]oxyacetic acid; {9-[(3-fluorophenyl)methyl]-5-carbamoylcarbazol-4-yl}oxyacetic acid; {9-[(3-chlorophenyl)methyl]-5-carbamoylcarbazol-4-yl}oxyacetic acid; {9-[(3-phenoxyphenyl)methyl]-5-carbamoylcarbazol-4-yl}oxyacetic acid; {9-[(2-Fluorophenyl)methyl]-5-carbamoylcarbazol-4-yl}oxyacetic acid; {9-[(2-trifluoromethylphenyl)methyl]-5-carbamoylcarbazol-4-yl}oxyacetic acid; {9-[(2-benzylphenyl)methyl]-5-carbamoylcarbazol-4-yl}oxyacetic acid; {9-[(3-trifluoromethylphenyl)methyl]-5-carbamoylcarbazol-4-yl}oxyacetic acid; {9-[(1-naphthyl)methyl]-5-carbamoylcarbazol-4-yl}oxyacetic acid; {9-[(2-cyanophenyl)methyl]-5-carbamoylcarbazol-4-yl}oxyacetic acid; {9-[(3-cyanophenyl)methyl]-5-carbamoylcarbazol-4-yl}oxyacetic acid; {9-[(2-methylphenyl)methyl]-5-carbamoylcarbazol-4-yl}oxyacetic acid; {9-[(3-methylphenyl)methyl]-5-carbamoylcarbazol-4-yl}oxyacetic acid; {9-[(3,5-dimethylphenyl)methyl]-5-carbamoylcarbazol-4-yl}oxyacetic acid; {9-[(3-iodophenyl)methyl]-5-carbamoylcarbazol-4-yl}oxyacetic acid; {9-[(2-Chlorophenyl)methyl]-5-carbamoylcarbazol-4-yl}oxyacetic acid; {9-[(2,3-difluorophenyl)methyl]-5-carbamoylcarbazol-4-yl}oxyacetic acid; {9-[(2,6-difluorophenyl)methyl]-5-carbamoylcarbazol-4-yl}oxyacetic acid; {9-[(2,6-dichlorophenyl)methyl]-5-carbamoylcarbazol-4-yl}oxyacetic acid; {9-[(3-trifluoromethoxyphenyl)methyl]-5-carbamoylcarbazol-4-yl}oxyacetic acid; {9-[(2-biphenyl)methyl]-5-carbamoylcarbazol-4-yl}oxyacetic acid; {9-[(2-Biphenyl) methyl]-5-carbamoylcarbazol-4-yl}oxyacetic acid methyl ester; [9-Benzyl-4-carbamoyl-1,2,3,4-tetrahydrocarbazole-5-yl]oxyacetic acid; {9-[(2-Pyridyl)methyl]-5-carbamoylcarbazol-4-yl}oxyacetic acid; {9-[(3-Pyridyl)methyl]-5-carbamoylcarbazol-4-yl}oxyacetic acid; [9-benzyl-4-carbamoyl-8-methyl-1,2,3,4-tetrahydrocarbazol-5-yl] oxyacetic acid; [9-benzyl-5-carbamoyl-1-methylcarbazol-4-yl]oxyacetic acid; [9-benzyl-4-carbamoyl-8-fluoro-1,2,3,4-tetrahydrocarbazol-5-yl]oxyacetic acid; [9-benzyl-5-carbamoyl-1-fluorocarbazol-4-yl]oxyacetic acid; [9-benzyl-4-carbamoyl-8-chloro-1,2,3,4-tetrahydrocarbazol-5-yl] oxyacetic acid; [9-benzyl-5-carbamoyl-1-chlorocarbazol-4-yl]oxyacetic acid; [9-[(Cyclohexyl)methyl]-5-carbamoylcarbazol-4-yl]oxyacetic acid; [9-[(Cyclopentyl)methyl]-5-carbamoylcarbazol-4-yl]oxyacetic acid; [5-carbamoyl-9-(phenylmethyl)-2-(2-thienyl)carbazol-4-yl] oxyacetic acid; [5-carbamoyl-9-(phenylmethyl)-2-[[(propen-3-yl)oxy]methyl]carbazol-4-yl]oxyacetic acid; [5-carbamoyl-9-(phenylmethyl)-2-[(propyloxy)methyl]carbazol-4-yl]oxyacetic acid; 9-benzyl-7-methoxy-5-((carboxamidomethyl)oxy)-1,2,3,4-tetrahydrocarbazole-4-carboxamide; 9-benzyl-7-methoxy-5-cyanomethyloxy-carbazole-4-carboxamide; 9-benzyl-7-methoxy-5-((1H-tetrazol-5-yl-methyl)oxy)-carbazole-4-carboxamide; 9-benzyl-7-methoxy-5-((carboxamidomethyl)oxy)-carbazole-4-carboxamide; [9-Benzyl-4-carbamoyl-1,2,3,4-tetrahydrocarbazole-5-yl]oxyacetic acid; (R,S)-(9-benzyl-4-carbamoyl-1-oxo-3-thia-1,2,3,4-tetrahydrocarbazol-5-yl) oxyacetic acid; (R,S)-(9-benzyl-4-carbamoyl-3-thia-1,2,3,4-tetrahydrocarbazol-5-yl)oxyacetic acid; 2-(4-oxo-5-carboxamido-9-benzyl-9H-pyrido[3,4-b]indolyl)acetic acid chloride; [N-benzyl-1-carbamoyl-1-aza-1,2,3,4-tetrahydrocarbazol-8-yl]oxyacetic acid; 4-methoxy-6-methoxycarbonyl-10-phenylmethyl-6,7,8,9-tetrahydropyrido[1,2-a]indole; (4-carboxamido-9-phenylmethyl-4,5-dihydrothiopyrano[3,4-b]indol-5-yl)oxyacetic acid; 3,4-dihydro-4-carboxamidol-5-methoxy-9-phenylmethylpyrano[3,4-b]indole; 2-[(2,9 bis-benzyl-4-carbamoyl-1,2,3,4-tetrahydro-betacarbolin-5-yl) oxy]acetic acid; 2-[4-oxo-5-carboxamido-9-(2-methylbenzyl)-9H-pyrido[3,4-b]indolyl]acetic acid; 2-[4-oxo-5-carboxamido-9-(3-methylbenzyl)-9H-pyrido[3,4-b]indolyl]acetic acid; 2-[4-oxo-5-carboxamido-9-(4-methylbenzyl)-9H-pyrido[3,4-b]indolyl]acetic acid; 2-[4-oxo-5-carboxamido-9-(4-tert-butylbenzyl)-9H-pyrido[3,4-b]indolyl]acetic acid; 2-[4-oxo-5-carboxamido-9-pentafluorobenzyl-9H-pyrido[3,4-b]indolyl]acetic acid; 2-[4-oxo-5-carboxamido-9-(2-fluorobenzyl)-9H-pyrido[3,4-b]indolyl]acetic acid; 2-[4-oxo-5-carboxamido-9-(3-fluorobenzyl)-9H-pyrido[3,4-b]indolyl]acetic acid; 2-[4-oxo-5-carboxamido-9-(4-fluorobenzyl)-9H-pyrido[3,4-b]indolyl] acetic acid; 2-[4-oxo-5-carboxamido-9-(2,6-difluorobenzyl)-9H-pyrido[3,4-b]indolyl]acetic acid; 2-[4-oxo-5-carboxamido-9-(3,4-difluorobenzyl)-9H-pyrido[3,4-b]indolyl]acetic acid; 2-[4-oxo-5-carboxamido-9-(2,5-difluorobenzyl)-9H-pyrido[3,4-b]indolyl]acetic acid; 2-[4-oxo-5-carboxamido-9-(3,5-difluorobenzyl)-9H-pyrido[3,4-b]indolyl]acetic acid; 2-[4-oxo-5-carboxamido-9-(2,4-difluorobenzyl)-9H-pyrido[3,4-b]indolyl]acetic acid; 2-[4-oxo-5-carboxamido-9-(2,3-difluorobenzyl)-9H-pyrido[3,4-b]indolyl]acetic acid; 2-[4-oxo-5-carboxamido-9-[2-(trifluoromethyl)benzyl]-9H-pyrido[3,4-b]indolyl]acetic acid; 2-[4-oxo-5-carboxamido-9-[2-(trifluoromethyl)benzyl]-9H-pyrido[3,4-b]indolyl]acetic acid; 2-[4-oxo-5-carboxamido-9-[3-(trifluoromethyl)benzyl]-9H-pyrido[3,4-b]indolyl]acetic acid; 2-[4-oxo-5-carboxamido-9-[4-

(trifluoromethyl)benzyl]-9H-pyrido[3,4-b]indolyl]acetic acid; 2-[4-oxo-5-carboxamido-9-[3,5-bis(trifluoromethyl)benzyl]-9H-pyrido[3,4-b]indolyl]acetic acid; 2-[4-oxo-5-carboxamido-9-[2,4-bis(trifluoromethyl)benzyl]-9H-pyrido[3,4-b]indolyl]acetic acid; 2-[4-oxo-5-carboxamido-9-(a-methylnaphthyl)-9H-pyrido[3,4-b]indolyl]acetic acid; 2-[4-oxo-5-carboxamido-9-(b-methylnaphthyl)-9H-pyrido[3,4-b]indolyl]acetic acid; 2-[4-oxo-5-carboxamido-9-(3,5-dimethylbenzyl)-9H-pyrido[3,4-b]indolyl]acetic acid; 2-[4-oxo-5-carboxamido-9-(2,4-dimethylbenzyl)-9H-pyrido[3,4-b]indolyl]acetic acid; 2-[4-oxo-5-carboxamido-9-(2-phenylbenzyl)-9H-pyrido[3,4-b]indolyl]acetic acid; 2-[4-oxo-5-carboxamido-9-(3-phenylbenzyl)-9H-pyrido[3,4-b]indolyl]acetic acid; 2-[4-oxo-5-carboxamido-9-(4-phenylbenzyl)-9H-pyrido[3,4-b]indolyl]acetic acid; 2-[4-oxo-5-carboxamido-9-(1-fluorenylmethy)-9H-pyrido[3,4-b]indolyl]acetic acid; 2-[4-oxo-5-carboxamido-9-(2-fluoro-3-methylbenzyl)-9H-pyrido[3,4-b]indolyl]acetic acid; 2-[4-oxo-5-carboxamido-9-(3-benzoylbenzyl)-9H-pyrido[3,4-b]indolyl]acetic acid; 2-[4-oxo-5-carboxamido-9-(2-phenoxybenzyl)-9H-pyrido[3,4-b]indolyl]acetic acid; 2-[4-oxo-5-carboxamido-9-(3-phenoxybenzyl)-9H-pyrido[3,4-b]indolyl]acetic acid; 2-[4-oxo-5-carboxamido-9-(4-phenoxybenzyl)-9H-pyrido[3,4-b]indolyl]acetic acid; 2-[4-oxo-5-carboxamido-9-[3-[2-(fluorophenoxy)benzyl]]-9H-pyrido[3,4-b]indolyl]acetic acid; 2-[4-oxo-5-carboxamido-9-[3-[4-(fluorophenoxy)benzyl]]-9H-pyrido[3,4-b]indolyl]acetic acid; 2-[4-oxo-5-carboxamido-9-[2-fluoro-3-(trifluoromethyl)benzyl]-9H-pyrido[3,4-b]indolyl]acetic acid; 2-[4-oxo-5-carboxamido-9-[2-fluoro-4-(trifluoromethyl)benzyl]-9H-pyrido[3,4-b]indolyl]acetic acid; 2-[4-oxo-5-carboxamido-9-[2-fluoro-5-(trifluoromethyl)benzyl]-9H-pyrido[3,4-b]indolyl]acetic acid; 2-[4-oxo-5-carboxamido-9-[3-fluoro-5-(trifluoromethyl)benzyl]-9H-pyrido[3,4-b]indolyl]acetic acid; 2-[4-oxo-5-carboxamido-9-[4-fluoro-2-(trifluoromethyl)benzyl]-9H-pyrido[3,4-b]indolyl]acetic acid; 2-[4-oxo-5-carboxamido-9-[4-fluoro-3-(trifluoromethyl)benzyl]-9H-pyrido[3,4-b]indolyl]acetic acid; 2-[4-oxo-5-carboxamido-9-[2-fluoro-6-(trifluoromethyl)benzyl]-9H-pyrido[3,4-b]indolyl]acetic acid; 2-[4-oxo-5-carboxamido-9-(2,3,6-trifluorobenzyl)-9H-pyrido[3,4-b]indolyl]acetic acid; 2-[4-oxo-5-carboxamido-9-(2,3,5-trifluorobenzyl)-9H-pyrido[3,4-b]indolyl]acetic acid; 2-[4-oxo-5-carboxamido-9-(2,4,5-trifluorobenzyl)-9H-pyrido[3,4-b]indolyl]acetic acid; 2-[4-oxo-5-carboxamido-9-(2,4,6-trifluorobenzyl)-9H-pyrido[3,4-b]indolyl]acetic acid; 2-[4-oxo-5-carboxamido-9-(2,3,4-trifluorobenzyl)-9H-pyrido[3,4-b]indolyl]acetic acid; 2-[4-oxo-5-carboxamido-9-(3,4,5-trifluorobenzyl)-9H-pyrido[3,4-b]indolyl]acetic acid; 2-[4-oxo-5-carboxamido-9-[3-(trifluoromethoxy)benzyl]-9H-pyrido[3,4-b]indolyl]acetic acid; 2-[4-oxo-5-carboxamido-9-[4-(trifluoromethoxy)benzyl]-9H-pyrido[3,4-b]indolyl]acetic acid; 2-[4-oxo-5-carboxamido-9-[4-methoxy(tetrafluoro)benzyl]-9H-pyrido[3,4-b]indolyl]acetic acid; 2-[4-oxo-5-carboxamido-9-(2-methoxybenzyl)-9H-pyrido[3,4-b]indolyl]acetic acid; 2-[4-oxo-5-carboxamido-9-(3-methoxybenzyl)-9H-pyrido[3,4-b]indolyl]acetic acid; 2-[4-oxo-5-carboxamido-9-(4-methoxybenzyl)-9H-pyrido[3,4-b]indolyl]acetic acid; 2-[4-oxo-5-carboxamido-9-(4-ethylbenzyl)-9H-pyrido[3,4-b]indolyl]acetic acid; 2-[4-oxo-5-carboxamido-9-(4-isopropylbenzyl)-9H-pyrido[3,4-b]indolyl]acetic acid; 2-[4-oxo-5-carboxamido-9-(3,4,5-trimethoxybenzyl)-9H-pyrido[3,4-b]indolyl]acetic acid; 2-[4-oxo-5-carboxamido-9-(3,4-methylenedioxybenzyl)-9H-pyrido[3,4-b]indolyl]acetic acid; 2-[4-oxo-5-carboxamido-9-(4-methoxy-3-methylbenzyl)-9H-pyrido[3,4-b]indolyl]acetic acid; 2-[4-oxo-5-carboxamido-9-(3,5-dimethoxybenzyl)-9H-pyrido[3,4-b]indolyl]acetic acid; 2-[4-oxo-5-carboxamido-9-(2,5-dimethoxybenzyl)-9H-pyrido[3,4-b]indolyl]acetic acid; 2-[4-oxo-5-carboxamido-9-(4-ethoxybenzyl)-9H-pyrido[3,4-b]indolyl]acetic acid; 2-[4-oxo-5-carboxamido-9-(cyclohexyl methyl)-9H-pyrido[3,4-b]indolyl]acetic acid; 2-[4-oxo-5-carboxamido-9-(cyclopentylmethyl)-9H-pyrido[3,4-b]indolyl]acetic acid; 2-[4-oxo-5-carboxamido-9-ethyl-9H-pyrido[3,4-b]indolyl]acetic acid; 2-[4-oxo-5-carboxamido-9-(1-propyl)-9H-pyrido[3,4-b]indolyl]acetic acid; 2-[4-oxo-5-carboxamido-9-(2-propyl)-9H-pyrido[3,4-b]indolyl]acetic acid; 2-[4-oxo-5-carboxamido-9-(1-butyl)-9H-pyrido[3,4-b]indolyl]acetic acid; 2-[4-oxo-5-carboxamido-9-(2-butyl)-9H-pyrido[3,4-b]indolyl]acetic acid; 2-[4-oxo-5-carboxamido-9-isobutyl-9H-pyrido[3,4-b]indolyl]acetic acid; 2-[4-oxo-5-carboxamido-9-[2-(1-phenylethyl)]-9H-pyrido[3,4-b]indolyl]acetic acid; 2-[4-oxo-5-carboxamido-9-[3-(1-phenylpropyl)]-9H-pyrido[3,4-b]indolyl]acetic acid; 2-[4-oxo-5-carboxamido-9-[4-(1-phenylbutyl)]-9H-pyrido[3,4-b]indolyl]acetic acid; 2-[4-oxo-5-carboxamido-9-(1-pentyl)-9H-pyrido[3,4-b]indolyl]acetic acid; 2-[4-oxo-5-carboxamido-9-(1-hexyl)-9H-pyrido[3,4-b]indolyl]acetic acid; 4-[(9-benzyl-4-carbamoyl-1,2,3,4-tetrahydrocarbazol-6-yl)oxy]butyric acid; 3-[(9-benzyl-4-carbamoyl-1,2,3,4-tetrahydrocarbazol-6-yl)oxy]propylphosphonic acid; 2-[(9-benzyl-4-carbamoyl-1,2,3,4-tetrahydrocarbazol-6-yl)oxy]methylbenzoic acid; 3-[(9-benzyl-4-carbamoyl-7-n-octyl-1,2,3,4-tetrahydrocarbazol-6-yl)oxy]propylphosphonic acid; 4-[(9-benzyl-4-carbamoyl-7-ethyl-1,2,3,4-tetrahydrocarbazol-6-yl)oxy]butyric acid; 3-[(9-benzyl-4-carbamoyl-7-ethyl-1,2,3,4-tetrahydrocarbazol-6-yl)oxy]propylphosphonic acid; 3-[(9-benzyl-4-carbamoyl-7-ethyl-1,2,3,4-tetrahydrocarbazol-6-yl)oxy]propylphosphonic acid; (S)-(+)-4-[(9-benzyl-4-carbamoyl-7-ethyl-1,2,3,4-tetrahydrocarbazol-6-yl)oxy]butyric acid; 4-[9-benzyl-4-carbamoyl-6-(2-cyanoethyl)-1,2,3,4-tetrahydrocarbazol-6-yl]oxybutyric acid; 4-[9-benzyl-4-carboxamido-7-(2-phenylethyl)-1,2,3,4-tetrahydrocarbazol-6-yl]oxybutyric acid; 4-[9-benzyl-4-carboxamidocarbazol-6-yl]oxybutyric acid; methyl 2-[(9-benzyl-4-carbamoyl-1,2,3,4-tetrahydrocarbazol-6-yl)oxy]methylbenzoate; 4-[9-benzyl-4-carbamoyl-7-(2-cyanoethyl)-1,2,3,4-tetrahydrocarbazol-6-yl]oxybutyric acid; 9-benzyl-7-methoxy-5-cyanomethyloxy-1,2,3,4-tetrahydrocarbazole-4-carboxamide; [9-benzyl-4-carbamoyl-8-methyl-carbazole-5-yl]oxyacetic acid; and [9-benzyl-4-carbamoyl-carbazole-5-yl]oxyacetic acid, or pharmaceutically acceptable salts, solvates, prodrug derivatives, racemates, tautomers, or optical isomers thereof.

In certain preferred embodiments, an sPLA$_2$ inhibitor for use in the present invention is ((3-(2-Amino-1,2-dioxoethyl)-2-ethyl-1-(phenylmethyl)-1H-indol-4-yl)oxy)acetic acid, also referred to herein as compound A-001. Compound A-001, which is also referred to in the art as S-5920 or LY315920, has the structure:

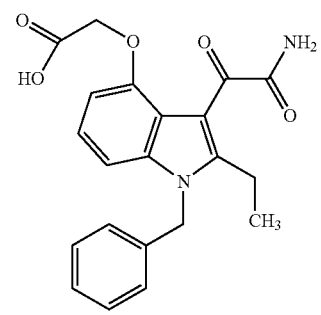

A-001 competitively inhibits sPLA$_2$.

In certain other preferred embodiments, an sPLA$_2$ inhibitor for use in the present invention is [[3-(2-Amino-1,2-dioxoethyl)-2-ethyl-1-(phenylmethyl)-1H-indol-4-yl]oxy]acetic acid methyl ester, also referred to herein as compound A-002. Compound A-002 has the structure:

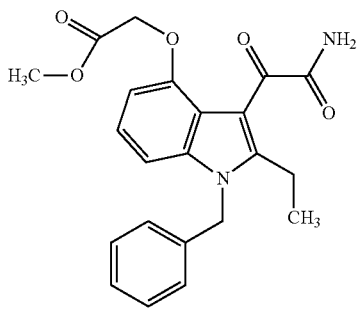

Compound A-002, which is sometimes referred to in the art as S-3013 or LY333013, is a prodrug form of A-001 that is rapidly absorbed and hydrolyzed to A-001 following administration to a subject.

In certain other preferred embodiments, an sPLA$_2$ inhibitor for use in the present invention is {9-[(phenyl)methyl]-5-carbamoylcarbazol-4-yl}oxyacetic acid, also referred to herein as compound A-003 or LY433771. Compound A-003 has the structure:

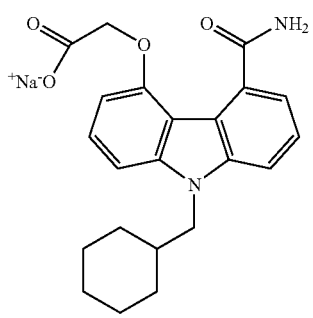

In still other preferred embodiments, an sPLA$_2$ inhibitor for use in the present invention is ((3-(2-amino-1,2-dioxoethyl)-2-methyl-1-(phenylmethyl)-1H-indol-4-yl)oxy)acetic acid N-morpholino ethyl ester, also referred to herein as compound 421079. Compound 421079 has the structure:

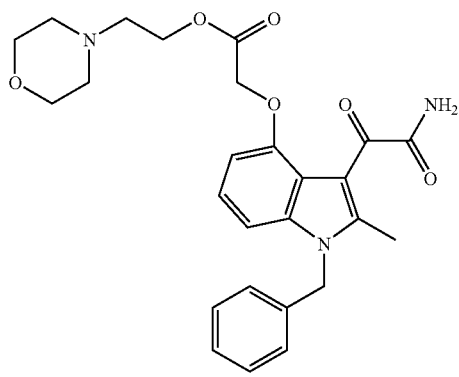

Like A-002, compound 421079 is a prodrug of A-001.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Effect of A-002 Administration on Plasma Cholesterol Levels and Atherosclerotic Plaque Formation in Mice Male ApoE$^{-/-}$ mice were fed a high fat diet (21% fat, 0.15% cholesterol, 19.5% casein) ad libitum for two weeks in order to acclimate to the diet. Plasma cholesterol levels and body weight were measured in order to obtain baseline levels, and mice were randomized into three groups of 20 mice based on these measurements. After the acclimation period, mice remained on the high fat diet and were administered A-002 (30 mg/kg or 90 mg/kg) or vehicle only (5% acacia) twice a day for 16 weeks by oral gavage.

Plasma cholesterol levels and body weight were measured at 4, 8, 12, and 16 weeks after the start of A-002 administration. Comparisons of measurements between test and control mice at each time period were performed using a two-way analysis of variance test (ANOVA) for repeated measures, followed by post-hoc Bonferroni test for significance.

At the end of the 16th week, mice were sacrificed and plasma samples, heart tissue, and aortas from the heart to approximately 3 mm distal to the iliac bifurcation were collected. Aortas were placed on microscope slides and stained with Oil Red O for scanning and image analysis of atherosclerotic lesion size. Vessel images were captured using a Microtek Scanmaker 9600XL scanner (Microtek, Carson, Calif.) and Photoshop 6.0 software (Adobe Systems Inc., San Jose, Calif.). Atherosclerotic plaque coverage was quantified for the entire length of the vessel including the arch using Image-Pro Plus software. Vessels were also analyzed for plaque coverage in the descending abdominal aorta, starting in the region of the first intercostal branches to the iliac bifurcation (not including the arch). Plaque content was expressed as a percent of the aortic surface. For assessment of significance in atherosclerotic plaque content between test and control mice, a one-way analysis of variance test followed by Bonferroni post-hoc test was used.

All three groups of mice (control, 30 mg/kg A-002, and 90 mg/kg A-002) had similar baseline body weights (FIG. 1). Body weight increased over the 16 week test period by approximately 155%, 150%, and 141% for control, 30 mg/kg A-002, and 90 mg/kg A-002 mice, respectively (FIG. 1). There was no statistically significant difference in body weight between the three groups.

Figure 2:
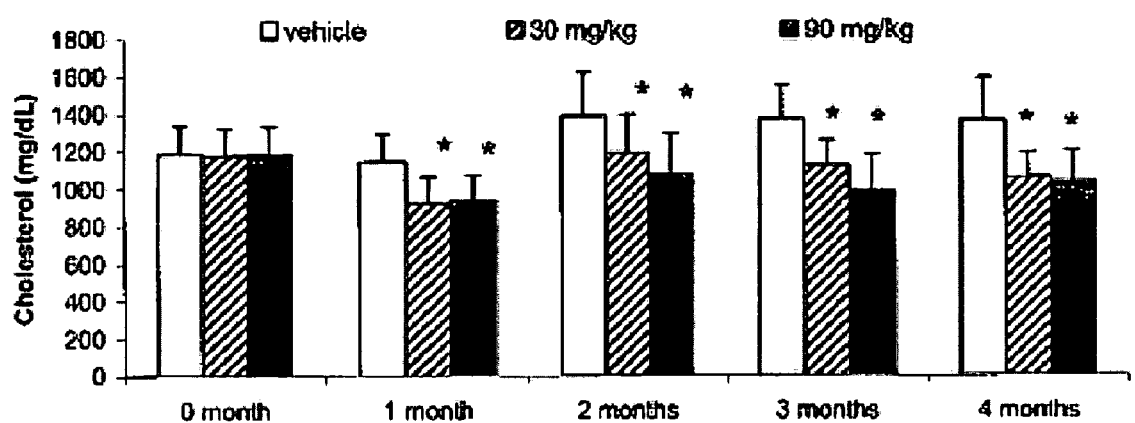
FIG. 2: Effect of A-002 administration on plasma total cholesterol levels in mice. ApoE$^{-/-}$ mice were administered vehicle only, 30 mg/kg A-002, or 90 mg/kg A-002 twice daily over 16 weeks. Total plasma cholesterol levels were measured at 0, 4, 8, 12, and 16 weeks.

Baseline total plasma cholesterol levels were not significantly different between the three groups (FIG. 2). At four weeks, mice receiving A-002 at either dosage exhibited a significant decrease in total cholesterol. This effect remained consistent throughout the remainder of the 16 week test period. At 16 weeks, the change from baseline in total cholesterol was +15%, −10%, and −12% in control, 30 mg/kg A-002, and 90 mg/kg A-002 mice, respectively (FIG. 2). There was no apparent dose-response effect.

Figure 3:
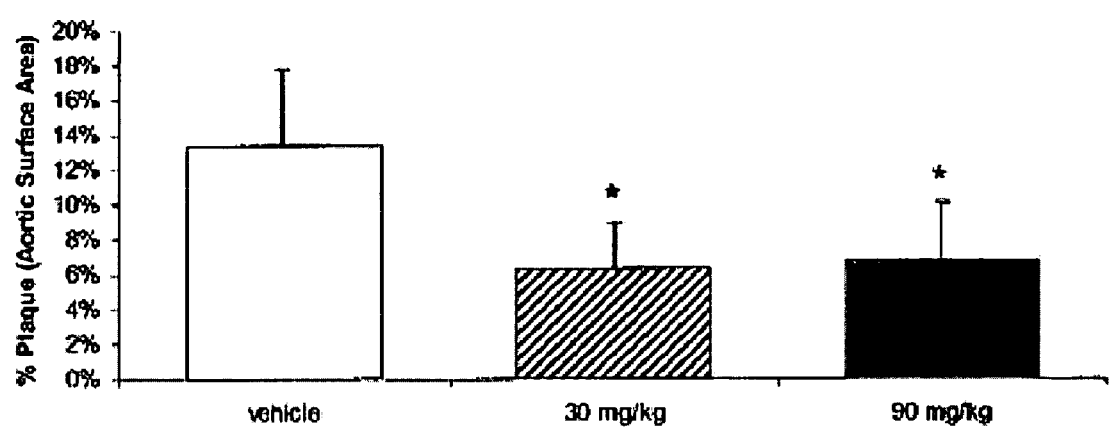
FIG. 3: Effect of A-002 administration on atherosclerotic plaque coverage in mice. ApoE$^{-/-}$ mice were administered vehicle only, 30 mg/kg A-002, or 90 mg/kg A-002 twice daily over 16 weeks. At 16 weeks, aortic plaque coverage was measured.

Control mice exhibited approximately 13% plaque coverage in aortic tissue at 16 weeks (FIG. 3). 30 mg/kg A-002 and 90 mg/kg A-002 mice exhibited 6.3% and 6.8% plaque coverage, respectively (FIG. 3). Therefore, A-002 treatment resulted in a significant decrease in plaque content.

Example 2

Effect of A-002 Administration on Angiotensin II-Mediated Atherosclerotic Plaque Formation and Aneurysm A mouse model of accelerated atherosclerosis was utilized to determine the effect of A-002 administration on atherosclerosis and aneurysm formation. ApoE$^{-/-}$ mice acclimated to the same high fat diet utilized in Example 1 were administered angiotensin II with water, angiotensin with 5% acacia, or saline infusion and water twice daily for four weeks. Angiotensin II has been shown to promote atherosclerosis and aneurysm formation in apoE deficient mice (Daugherty 2000). At the end of the test period, plaque coverage was assessed by three independent reviewers, and their assessments were averaged to determine plaque coverage.

Figure 4:
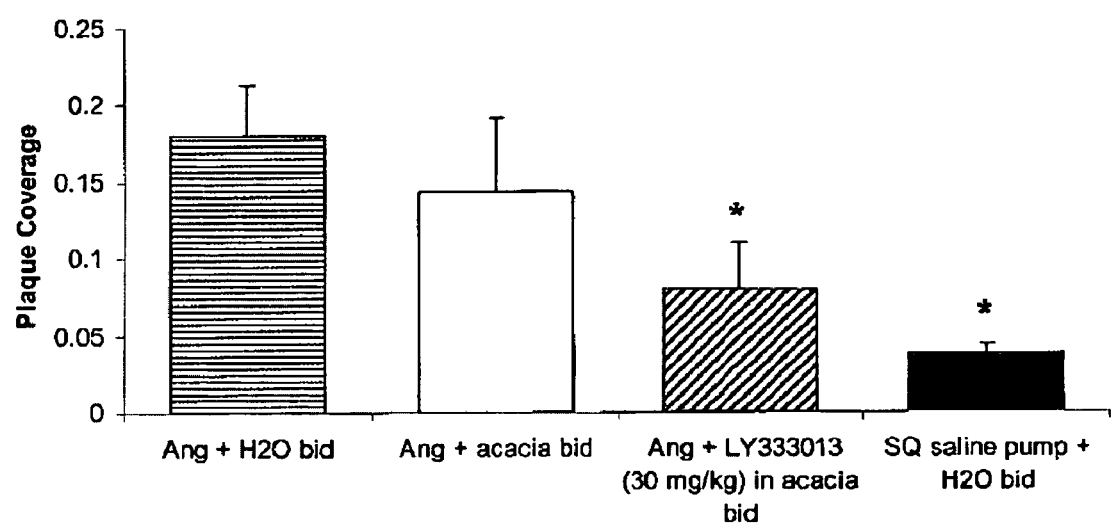
FIG. 4: Effect of A-002 administration on angiotensin II-mediated atherosclerotic plaque formation and aortic aneurysm. ApoE$^{-/-}$ mice were administered saline plus water, angiotensin II in water vehicle, angiotensin II in acacia vehicle, or angiotensin II in acacia vehicle plus 30 mg/kg A-002. At 4 weeks, aortic plaque coverage was measured.

Angiotensin II with water or with 5% acacia resulted in similar rates of plaque coverage (FIG. 4) and aneurysm (Table 1). Administration of A-002 at 30 mg/kg twice daily significantly decreased plaque content and aortic level aneurysms in angiotensin II/acacia mice (FIG. 4).

TABLE 1

Effect of A-002 administration on aneurysm rate:

| Treatment group | Aneurysm rate (%) |
|---|---|
| Angiotensin II + 5% acacia | 22% (2/9) |
| Angiotensin + water | 25% (5/20) |
| Saline + water | 0% (0/25) |
| Angiotensin II + 5% acacia + 30 mg/kg A-002 | 0% (0/16) |

Example 3

Effect of A-002 or A-002 Plus Statin on Lesion Formation and Composition in Mice Body weight, plasma total cholesterol, and plasma HDL levels were measured for six groups of twelve ApoE$^{-/-}$ mice. The mice were then placed on a high fat diet for twelve weeks to allow for formation of significant fatty atherosclerotic plaques. The high fat diet was a modified version of the Western diet (TD.88137, Harlan Teklad, Madison, Wis.) consisting of casein (195 g/kg), DL-methionine (3 g/kg), sucrose (341.44 g/kg), corn starch (150 g/kg), anhydrous milkfat (210 g/kg), cholesterol (1.5 g/kg), cellulose (50 g/kg), mineral mix AIN-76 (Teklad; 35 g/kg), calcium carbonate (4 g/kg), vitamin mix (Teklad #40060; 10 g/kg), ethyoxyquin (antioxidant, 0.04 g/kg), and either 0.0156 g/kg ("low dose") A-002 (Group A), 1.56 g/kg ("high dose") A-002 (Group B), 0.02 g/kg pravastatin (Group C), low dose A-002 plus 0.02 g/kg pravastatin (Group D), high dose A-002 plus 0.02 g/kg pravastatin (Group E), or vehicle only (Group F). Mice were administered diets A-F in a blinded manner, and food was provided ad libitum. The diet was initially prepared based on the assumption that each mouse weighed 22.5 g and ate 4.5 g/day. Based on body weight and food consumption, the diet was modified over the 12 week course of treatment to adjust for a body weight of 26 g and a food intake of 2.5 g/day. The dosages of A-002 were selected to cover a range of 100-fold based on pharmacokinetics in ApoE$^{-/-}$ mice as well as toxicology and previously observed efficacy in this model.

Figure 5:
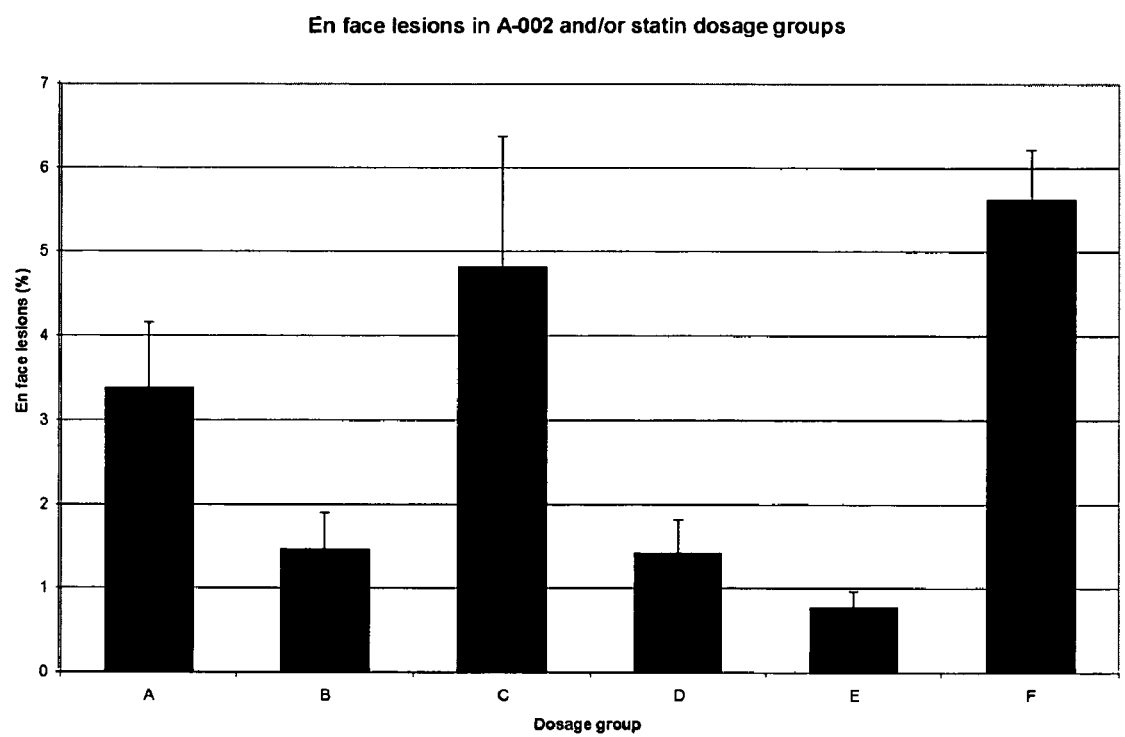
FIG. 5: En face lesions in A-002 and/or statin dosage groups. ApoE$^{-/-}$ mice on a high fat diet were administered various dosages of A-002, statin, or A-002 plus statin over twelve weeks, and en face lesion content was measured using digital imaging methods. Lesion size is expressed as percent coverage over entire tissue sample. A: low dose A-002; B: high dose A-002; C: statin; D: low dose A-002 plus statin; E: high dose A-002 plus statin; and F: vehicle only.

After twelve weeks, mice were sacrificed and plasma, heart tissue, and aortic tissue were collected. En face lesion size was determined via digital imaging analysis. Percent lesion coverage for each dosage group is summarized in Table 2 and FIG. 5. Plaque content (as measured as en face lesion) was reduced in mice administered A-002 alone, statin alone, or A-002 in combination with statin. The reduction in plaque content in mice administered A-002 plus statin was substantially greater than the reduction in mice administered either compound alone (Table 2, compare Group D vs. Groups A and C; Group E vs. Groups B and C). Further, the reduction in plaque content in mice administered A-002 plus statin was substantially greater than the sum of the reduction in plaque content in mice administered A-002 alone and mice administered statin alone. (Table 2, compare the change in mean % en face lesion vs. control for Group D (i.e., −4.210%) with the sum of the change in mean % en face lesion vs. control for Group A and Group C (i.e., the sum of −2.241% and −0.813%, or −3.054%).) Thus, the administration of A-002 plus statin reduces plaque content in a synergistic manner.

TABLE 2

Effect of A-002 and/or statin administration on en face lesion size:

| Dosage group | # of mice | Mean % en face lesion | Change in mean % en face lesion vs. control | P-value vs. control |
|---|---|---|---|---|
| Low A-002 (A) | 11 | 3.386 | −2.241 | 0.0597 |
| High A-002 (B) | 12 | 1.469 | −4.158 | 0.0006 |
| Statin (C) | 12 | 4.814 | −0.813 | 0.4797 |
| Low A-002 plus statin (D) | 10 | 1.417 | −4.210 | 0.0008 |
| High A-002 plus statin (E) | 10 | 0.774 | −4.853 | 0.0001 |
| Control (F) | 12 | 5.627 | — | — |

Figure 6:
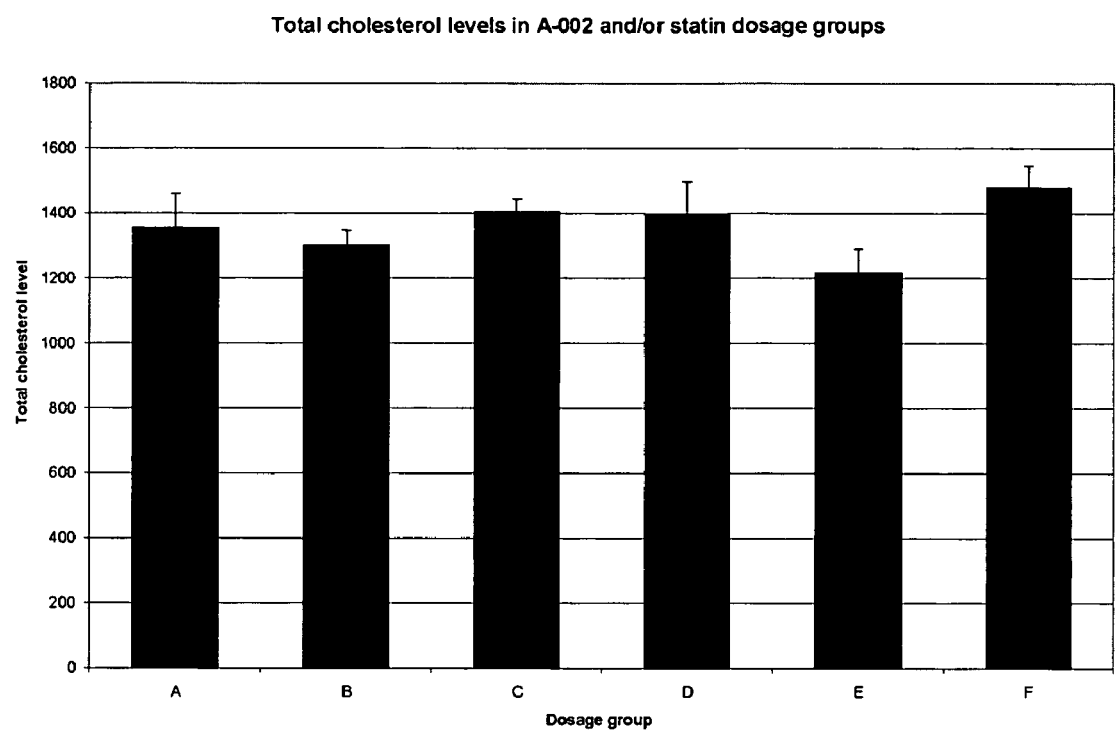
FIG. 6: Total plasma cholesterol levels in A-002 and/or statin dosage groups. ApoE$^{-/-}$ mice on a high fat diet were administered various dosages of A-002, statin, or A-002 plus statin over twelve weeks, and total cholesterol levels were measured. A: low dose A-002; B: high dose A-002; C: statin; D: low dose A-002 plus statin; E: high dose A-002 plus statin; and F: vehicle only.
Figure 7:
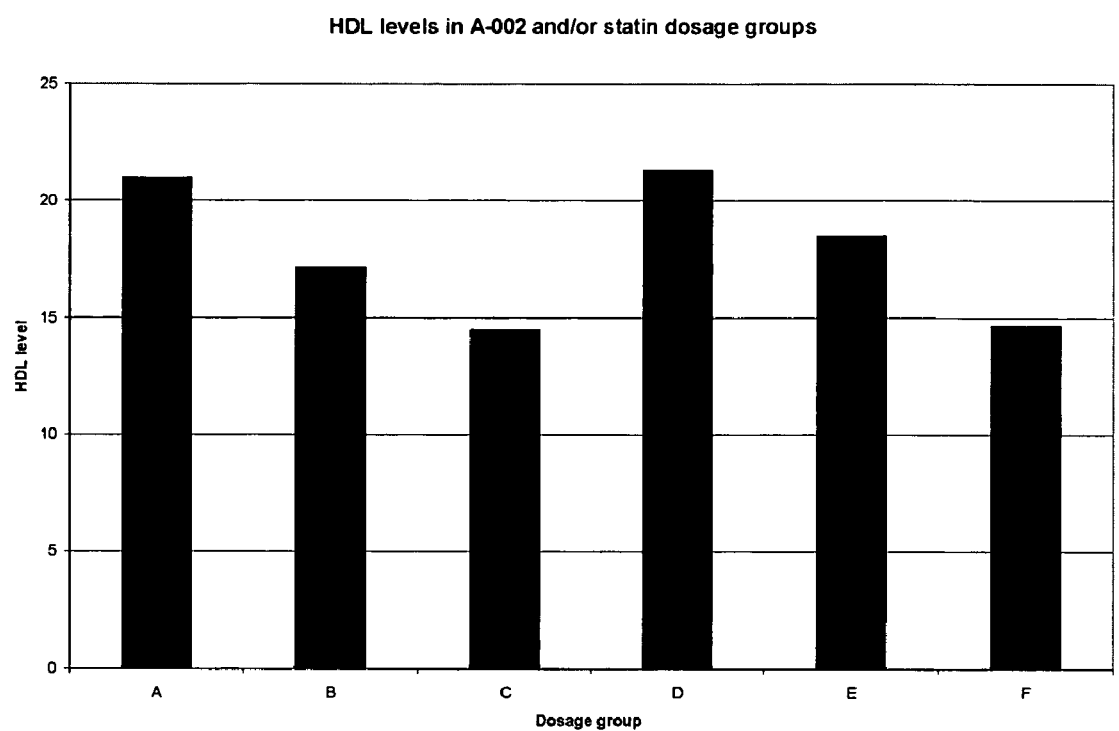
FIG. 7: HDL levels in A-002 and/or statin dosage groups. ApoE$^{-/-}$ mice on a high fat diet were administered various dosages of A-002, statin, or A-002 plus statin over twelve weeks, and HDL levels were measured. A: low dose A-002; B: high dose A-002; C: statin; D: low dose A-002 plus statin; E: high dose A-002 plus statin; and F: vehicle only.

Plasma total cholesterol and HDL levels were measured. Mean levels of total cholesterol were decreased in mice administered A-002 alone or in combination with statin (Table 3, FIG. 6). Administration of high dosage A-002 plus statin resulted in a greater decrease in total cholesterol than administration of high dosage A-002 or statin alone (Table 3, compare Group E vs. Groups B and C; FIG. 6). Mean levels of HDL were increased in mice administered A-002 at either dosage (Table 4). This increase was greater in mice administered high dose A-002 plus statin than in mice administered high dose A-002 or statin alone (Table 4 compare Group E vs. Groups B and C; FIG. 7).

TABLE 3

Effect of A-002 and/or statin administration on plasma total cholesterol levels

| Dosage group | # of mice | Mean total cholesterol concentration (mg/dl) | P-value vs. control |
|---|---|---|---|
| Low A-002 (A) | 11 | 1355.545 | 0.2296 |
| High A-002 (B) | 12 | 1301.750 | 0.0792 |
| Statin (C) | 12 | 1405.417 | 0.4647 |
| Low A-002 plus statin (D) | 10 | 1399.700 | 0.4521 |
| High A-002 plus statin (E) | 10 | 1219.300 | 0.0152 |
| Control (F) | 12 | 1478.083 | — |

TABLE 4

Effect of A-002 and/or statin administration on plasma HDL levels

| Dosage group | # of mice | Mean HDL concentration (mg/dl) | P-value vs. control |
|---|---|---|---|
| Low A-002 (A) | 11 | 21.000 | <0.0001 |
| High A-002 (B) | 12 | 17.167 | 0.0825 |
| Statin (C) | 12 | 14.500 | 0.9067 |
| Low A-002 plus statin (D) | 10 | 21.300 | <0.0001 |
| High A-002 plus statin (E) | 10 | 18.500 | 0.0123 |
| Control (F) | 12 | 14.667 | — |

Example 4

Effect of A-002 or A-002 Plus Statin Administration on Serum Lipid Levels in Humans 204 human subjects from the United States with CVD, specifically stable coronary artery disease, were randomized to receive placebo or A-002 via oral administration twice a day over an eight week administration period at dosages of 50 mg, 100 mg, 250 mg, or 500 mg. Levels of various lipids and inflammatory markers were measured at the outset of the trial and at the end of weeks four and/or eight. For data sets with a normal distribution, mean levels of lipids or inflammatory markers were analyzed. For data sets with non-normal distribution, median levels were analyzed. Administration of A-002 at all dosages tested resulted in a decrease in mean levels of serum LDL (Table 5), LDL particles (Table 6), small LDL particles (Table 7), total cholesterol (Table 8), and TG (Table 9), and median levels of sPLA$_2$ (Table 10). In addition, administration of A-002 decreased median levels of CRP (Table 11). The magnitude of the observed decreases in LDL particle, small LDL particle, and CRP levels are particularly noteworthy because subjects treated with placebo exhibited increases in these markers over the course of the trial (Tables 6, 7, and 11).

TABLE 5

Changes in serum LDL concentration in ITT population following A-002 administration

| | | A-002 | Placebo |
|---|---|---|---|
| Baseline | # of subjects | 154 | 37 |
| | Mean [LDL] | 76.8 mg/dl | 77.7 mg/dl |
| Week 8 | # of subjects observed | 143 | 36 |
| | Change in mean [LDL] vs. baseline | −8.2 mg/dl | −1.5 mg/dl |
| | % change vs. baseline | −10.68% | −1.93% |
| | p-value vs. baseline | <0.0001 | 0.5456 |

TABLE 6

Changes in serum LDL particle concentration in ITT population following A-002 administration

| | | A-002 | Placebo |
|---|---|---|---|
| Baseline | # of subjects | 158 | 38 |
| | Mean [LDL particle] | 1031.6 nmol/L | 1004.8 nmol/L |
| Week 8 | # of subjects observed | 129 | 33 |
| | Change in mean [LDL particle] vs. baseline | −73.6 nmol/L | +47.7 nmol/L |
| | % change vs. baseline | −7.13% | +4.75% |

TABLE 7

Changes in serum small LDL particle concentration in ITT population following A-002 administration

| | | A-002 | Placebo |
|---|---|---|---|
| Baseline | # of subjects | 158 | 38 |
| | Mean [small LDL particle] | 735.8 nmol/L | 661.7 nmol/L |
| Week 8 | # of subjects observed | 129 | 33 |
| | Change in mean [small LDL particle] vs. baseline | −61.3 nmol/L | +77.0 nmol/L |
| | % change vs. baseline | −8.33% | +11.64% |

TABLE 8

Changes in serum total cholesterol concentration in ITT population following A-002 administration

| | | A-002 | Placebo |
|---|---|---|---|
| Baseline | # of subjects | 158 | 39 |
| | Mean [total cholesterol] | 156.8 mg/dl | 156.9 mg/dl |
| Week 8 | # of subjects observed | 146 | 37 |
| | Change in mean [total cholesterol] vs. baseline | −12.8 mg/dl | −4.7 mg/dl |
| | % change vs. baseline | −8.16% | −2.99% |
| | p-value vs. baseline | <0.0001 | 0.1130 |

TABLE 9

Changes in serum TG concentration in ITT population following A-002 administration

| | | A-002 | Placebo |
|---|---|---|---|
| Baseline | # of subjects | 158 | 39 |
| | Mean [TG] | 151.5 mg/dl | 150.6 mg/dl |
| Week 8 | # of subjects observed | 146 | 37 |
| | Change in mean [TG] vs. baseline | −10.1 mg/dl | −0.7 mg/dl |
| | % change vs. baseline | −6.67% | −0.46% |

TABLE 10

Changes in serum $sPLA_2$ concentration in ITT population following A-002 administration

| | | A-002 | Placebo |
|---|---|---|---|
| Baseline | # of subjects | 159 | 41 |
| | Median [$sPLA_2$] | 2.30 ng/ml | 2.20 ng/ml |
| Week 8 | # of subjects observed | 110 | 29 |
| | Change in median [$sPLA_2$] vs. baseline | −2.00 ng/ml | −0.30 ng/ml |
| | % change vs. baseline | −86.96% | −13.64% |
| | p-value vs. baseline | <0.0001 | 0.0207 |

TABLE 11

Changes in serum CRP concentration in ITT population following A-002 administration

| | | A-002 | Placebo |
|---|---|---|---|
| Baseline | # of subjects | 155 | 38 |
| | Median [CRP] | 1.50 mg/L | 2.00 mg/L |
| Week 8 | # of subjects observed | 143 | 36 |
| | Change in median [CRP] vs. baseline | −0.20 mg/L | +0.10 mg/L |
| | % change vs. baseline | −13.33% | +5.00% |
| | p-value vs. baseline | 0.0205 | 0.4478 |

The median baseline LDL concentration in the 204 subject United States ITT population was 72.0 mg/dl. A-002 administration resulted in a significant decrease in mean LDL levels in a 97 subject subpopulation with baseline LDL levels equal to or higher than the median concentration (Table 12). In addition, administration of A-002 decreased mean serum LDL levels in a 53 subject subpopulation with diabetes (Table 13).

TABLE 12

Changes in serum LDL concentration in subpopulation with baseline serum LDL concentration greater than or equal to 72 mg/dl following A-002 administration

| | | A-002 | Placebo |
|---|---|---|---|
| Baseline | # of subjects | 79 | 18 |
| | Mean [LDL] | 95.4 mg/dl | 98.0 mg/dl |
| Week 8 | # of subjects | 70 | 16 |
| | Change in mean [LDL] vs. baseline | −14.0 mg/dl | −3.5 mg/dl |
| | % change vs. baseline | −14.68% | −3.57% |
| | p-value vs. baseline | <0.0001 | 0.3428 |

TABLE 13

Changes in serum LDL concentration in diabetic subpopulation following A-002 administration

| | | A-002 | Placebo |
|---|---|---|---|
| Baseline | # of subjects | 43 | 8 |
| | Mean [LDL] | 63.7 mg/dl | 75.1 mg/dl |
| Week 8 | # of subjects | 37 | 8 |
| | Change in mean [LDL] vs. baseline | −10.6 mg/dl | −4.3 mg/dl |

TABLE 13-continued

Changes in serum LDL concentration in diabetic
subpopulation following A-002 administration

|  | A-002 | Placebo |
|---|---|---|
| % change vs. baseline | −16.64% | −5.73% |

A decrease in mean small LDL particle levels was observed in the subset of the US population that was receiving statin treatment during the trial (Table 14), indicating that administration of A-002 plus statin results in a greater decrease in small LDL particles than administration of statin alone. Likewise, a decrease in mean serum LDL levels was observed in an 81 subject subpopulation of the statin treatment group exhibiting elevated baseline LDL levels (i.e., baseline LDL levels greater than or equal to 72 mg/dl) (Table 15).

TABLE 14

Changes in serum small LDL particle concentration in statin
subpopulation following A-002 administration

|  |  | A-002 | Placebo |
|---|---|---|---|
| Baseline | # of subjects | 139 | 33 |
|  | Mean [small LDL particle] | 735.3 nmol/L | 664.4 nmol/L |
| Week 8 | # of subjects observed | 114 | 27 |
|  | Change in mean [small LDL particle] vs. baseline | −66.2 nmol/L | +88.1 nmol/L |
|  | % change vs. baseline | −9.00% | +13.26% |

TABLE 15

Changes in serum LDL concentration in statin subpopulation
with baseline serum LDL concentration greater than or equal
to 72 mg/dl following A-002 administration

|  |  | A-002 | Placebo |
|---|---|---|---|
| Baseline | # of subjects | 66 | 15 |
|  | Mean [LDL] | 92.2 mg/dl | 86.3 mg/dl |
| Week 8 | # of subjects | 58 | 13 |
|  | Change in mean [LDL] vs. baseline | −15.0 mg/dl | −3.8 mg/dl |
|  | % change vs. baseline | −16.27% | −4.40% |
|  | p-value vs. baseline | <0.0001 | 0.3792 |

The combined effect of A-002 and statin administration on LDL levels was tested in a population of 332 subjects. This population consisted of the original 204 United States subjects, plus an additional 128 subjects from the Ukraine with stable CAD that received placebo or A-002 based according to the same protocol as the United States subjects. A decrease in mean serum LDL levels was observed in the statin subpopulation at four and eight weeks (Table 16), indicating that administration of A-002 and statin results in a greater decrease in serum LDL levels than administration of statin alone. Similarly, A-002 decreased LDL levels in subjects receiving a variety of non-statin compounds used in the treatment of CVD, including ezetimibe, AEGR-733/ezetimibe, colesevelam hydrochloride (WelChol®), MK-0524A (Cordaptive®), lisinopril/MC-1 antibody (MC-4232), and Angiotensin Receptor Blocker (ARB)/MC-1 (MC-4262).

TABLE 16

Changes in serum LDL concentration in statin
subpopulation following A-002 administration

|  |  | A-002 | Placebo |
|---|---|---|---|
| Baseline | # of subjects | 156 | 36 |
|  | Mean [LDL] | 76.9 mg/dl | 74.5 mg/dl |
| Week 4 | # of subjects | 152 | 35 |
|  | Change in mean [LDL] vs. baseline | −10.8 mg/dl | −2.5 mg/dl |
|  | % change vs. baseline | −14.04% | −3.36% |
| Week 8 | # of subjects | 131 | 31 |
|  | Change in mean [LDL] vs. baseline | −9.6 mg/dl | −1.6 mg/dl |
|  | % change vs. baseline | −12.48% | −2.15% |

Comparison of the above statin subpopulation results with results for subjects that were not receiving statin treatment indicates that administration of A-002 plus statin results in a greater decrease in mean serum small LDL particle and LDL levels than the expected additive effect of A-002 and statin (compare Table 17 to Table 14 and Table 18 to Table 16). In the United States population, mean serum small LDL particle levels were reduced at eight weeks by 9.00% in subjects administered A-002 plus statin (Table 14), versus a decrease of 3.25% in subjects administered A-002 alone (Table 17) and an increase of 13.26% in subjects administered statin alone (Table 14). These results summarized in Table 20. In the combined United States and Ukraine populations, mean serum LDL levels were decreased by 14.04% at week four in subjects administered A-002 plus statin (Table 16), versus a decrease of 6.93% in subjects administered A-002 alone (Table 18) and a decrease of 3.36% in subjects administered statin alone (Table 16). At week eight, mean serum LDL levels were decreased by 12.48% in subjects administered A-002 plus statin (Table 16), versus a decrease of 4.22% in subjects administered A-002 alone (Table 18) and a decrease of 2.15% in subjects administered statin alone (Table 16). These results are also summarized in Table 20. Therefore, administration of A-002 plus statin decreases LDL and small LDL particle levels in a synergistic manner.

This synergism was also observed in subjects from the United States population that had baseline LDL concentrations of 72 mg/dl or greater (compare Table 19 to Table 15).

Mean serum LDL levels were decreased at eight weeks by 16.27% in subjects administered A-002 plus statin (Table 15), versus a decrease of 8.23% in subjects administered A-002 alone (Table 19) and a decrease of 4.40% in subjects administered statin alone (Table 15). These results are summarized in Table 20.

TABLE 17

Changes in serum small LDL particle concentration in non-statin subpopulation following A-002 administration

|  |  | A-002 | Placebo |
|---|---|---|---|
| Baseline | # of subjects | 19 | 5 |
|  | Mean [small LDL particle] | 739.5 nmol/L | 644.4 nmol/L |
| Week 8 | # of subjects observed | 15 | 6 |
|  | Change in mean [small LDL particle] vs. baseline | −24.0 nmol/L | +19.4 nmol/L |
|  | % change vs. baseline | −3.25% | +3.01% |

TABLE 18

Changes in serum LDL levels in non-statin subpopulation following A-002 administration

|  |  | A-002 | Placebo |
|---|---|---|---|
| Baseline | # of subjects | 102 | 21 |
|  | Mean [LDL] | 125.6 mg/dl | 135.6 mg/dl |
| Week 4 | # of subjects | 86 | 22 |
|  | Change in mean [LDL] vs. baseline | −8.7 mg/dl | +0.2 mg/dl |
|  | % change vs. baseline | −6.93% | +0.15% |
| Week 8 | # of subjects | 20 | 5 |
|  | Change in mean [LDL] vs. baseline | −5.3 mg/dl | −1.3 mg/dl |
|  | % change vs. baseline | −4.22% | −0.96% |

TABLE 19

Changes in serum LDL concentration in non-statin subpopulation with baseline serum LDL levels greater than or equal to 72 mg/dl following A-002 administration

|  |  | A-002 | Placebo |
|---|---|---|---|
| Baseline | # of subjects | 13 | 3 |
|  | Mean [LDL] | 111.8 mg/dl | 156.3 mg/dl |
| Week 8 | # of subjects | 12 | 3 |
|  | Change in mean [LDL] vs. baseline | −9.2 mg/dl | −2.3 mg/dl |
|  | % change vs. baseline | −8.23% | −1.47% |
|  | p-value vs. baseline | 0.0574 | 0.8021 |

TABLE 20

Summary of the synergistic effects of combined A-002 and statin administration versus administration of A-002 or statin alone

|  | Observed change following administration of A-002 alone | Observed change following administration of statin alone | Expected change from administration of A-002 plus statin (change for A-002 alone plus change for statin alone) | Observed change following administration of A-002 plus statin |
|---|---|---|---|---|
| Mean serum [small LDL particle] at week 8 | −3.25% (Table 17) | +13.26% (Table 14) | +10.01% (−3.25% plus +13.26%) | −9.00% (Table 14) |
| Mean serum [LDL] at week 4 | −6.93% (Table 18) | −3.36% (Table 16) | −10.29% (−6.93% plus −3.36%) | −14.04% (Table 16) |
| Mean serum [LDL] at week 8 | −4.22% (Table 18) | −2.15 (Table 16) | −6.37% (−4.22% plus −2.15%) | −12.48 (Table 16) |
| Mean serum [LDL] in ≧72 mg/dl subpopulation at week 8 | −8.23% (Table 19) | −4.40% (Table 15) | −12.63% (−8.23% plus −4.40%) | −16.27% (Table 15) |

Serum LDL data for subjects in the statin subpopulation were subdivided based on the specific statin each subject was receiving. Statins with significant representation included atorvastatin, rosuvastatin, simvastatin, lovastatin, pravastatin, and fluvastatin, as well as the statin combination drugs simvastatin/ezetimibe (Vytorin®), atorvastatin/ezetimibe, atorvastatin/amlodipine (Caduet®), lovastatin/extended release niacin (Advicor®), rosuvastatin/TriCor®, rosuvastatin/ABT-335, simvastatin/extended release niacin (Simcor®), simvastatin/MK-0524A (M K-0524B), pravastatin/fenofibrate, atorvastatin/APA-01, and TAK-457/statin. Statin and statin combination dosages varied within each individual statin subgroup. The number of test and placebo subjects in each individual statin subgroup from the larger statin subpopulation was too low to allow for detailed statistical analysis. However, there appeared to be a trend towards the same synergistic decrease in LDL levels that was observed in the statin subpopulation as a whole in several of the statin subgroups, such as for example with certain dosages of atorvastatin, rosuvastatin, and simvastatin. These results indicate that the observed synergy between A-002 and statins is not limited to a particular statin.

The synergistic effect of A-002 and compounds used in the treatment of CVD on LDL levels was not limited to statins. For example, 30 subjects from the ITT population were receiving ezetimibe at a dosage of 10 mg during the course of the A-002 trial. Administration of A-002 resulted in a decrease in mean serum LDL levels in the ezetimibe subpopulation after eight weeks (Table 21), indicating that administration of A-002 plus ezetimibe results in a greater decrease in LDL levels than administration of ezetimibe alone (Table 21). As with the statin subpopulation, administration of A-002 in conjunction with ezetimibe resulted in a synergistic decrease in mean LDL levels that was greater than the expected additive effect of A-002 and ezetimibe (Table 22).

TABLE 21

Changes in serum LDL concentration in ezetimibe subpopulation following A-002 administration

|  |  | A-002 | Placebo |
|---|---|---|---|
| Baseline | # of subjects | 28 | 12 |
|  | Mean [LDL] | 81.0 mg/dl | 79.6 mg/dl |
| Week 8 | # of subjects | 28 | 12 |
|  | Change in mean [LDL] vs. baseline | −15.4 mg/dl | −1.0 mg/dl |
|  | % change vs. baseline | −17.8% | −1.7% |

TABLE 22

Summary of the synergistic effects of combined A-002 and ezetimibe administration versus administration of A-002 or ezetimibe alone

|  | Observed change following administration of A-002 alone | Observed change following administration of ezetimibe alone | Expected change from administration of A-002 plus ezetimibe (change for A-002 alone plus change for ezetimibe) | Observed change following administration of A-002 plus ezetimibe |
|---|---|---|---|---|
| Mean serum [LDL] at week 8 | −4.22% (Table 18) | −1.7% (Table 21) | −5.92% (−4.22% plus −1.7%) | −17.8% (Table 21) |

Serum TG, CRP, and IL-6 levels were measured at eight weeks in 86 subjects from the ITT population diagnosed with metabolic syndrome. Administration of A-002 resulted in a decrease in serum levels of each of these markers (Tables 23-25). Subjects administered placebo exhibited an increase in CRP and IL-6 levels (Tables 24-25).

TABLE 23

Changes in serum TG concentration in metabolic syndrome subpopulation following A-002 administration

|  |  | A-002 | Placebo |
|---|---|---|---|
| Baseline | # of subjects | 70 | 16 |
|  | Median [TG] | 171.5 mg/dl | 168.0 mg/dl |
| Week 8 | # of subjects observed | 63 | 13 |
|  | Change in median [TG] vs. baseline | −24.0 mg/dl | −3.0 mg/dl |
|  | % change vs. baseline | −13.99% | −1.79% |

TABLE 24

Changes in serum CRP concentration in metabolic syndrome subpopulation following A-002 administration

|  |  | A-002 | Placebo |
|---|---|---|---|
| Baseline | # of subjects | 69 | 16 |
|  | Median [CRP] | 2.40 mg/L | 2.60 mg/dl |
| Week 8 | # of subjects observed | 62 | 13 |
|  | Change in median [CRP] vs. baseline | −0.3 mg/L | +0.1 mg/L |
|  | % change vs. baseline | −12.50% | +3.84% |

TABLE 25

Changes in serum IL-6 concentration in metabolic syndrome subpopulation following A-002 administration

|  |  | A-002 | Placebo |
|---|---|---|---|
| Baseline | # of subjects | 68 | 16 |
|  | Mean [IL-6] | 5.60 pg/ml (15.30) | 5.17 pg/ml (2.60) |
| Week 8 | # of subjects observed | 44 | 10 |
|  | Change in mean [IL-6] vs. baseline | −0.24 pg/ml | +0.29 pg/ml |
|  | % change vs. baseline | −4.29% | +5.61% |

Example 5

A-002 Plus Statin Combination Tablet

Fixed dose tablets containing A-002 and one or more statins may be generated using methods known in the art. For example, a fixed dose tablet containing a therapeutically effective amount of A-002 (e.g., 250 or 500 mg) and a therapeutically effective amount of a statin (e.g., 10, 20, 40, or 80 mg), may be generated using a formula such as that set forth in Table 26. One of ordinary skill in the art will recognize that additional components may be added to this generic formulation. For example, a compound such as calcium carbonate may be added to the formulation to enhance dissolution and solubility. Likewise, one of skill in the art will recognize that this formulation is just one example of a generic A-002/statin formulation, and that the identity and weight of the recited components within the formulation may be varied without undue experimentation.

TABLE 26

Generic A-002/statin formulation:

| Component | Typical weight percentage |
|---|---|
| A-002 | Varies depending on desired dosage |
| Statin | Varies depending on desired dosage |
| Anhydrous lactose | 20-50% |
| Lactose monohydrate | 20-50% |
| Hydroxypropyl cellulose | 2-6% |
| Croscarmellose sodium | 0.5-5% |
| Polysorbate 80 | 0.1-3% |
| Microcrystalline cellulose | 5-20% |
| Magnesium stearate | 0.25-3% |

To verify the feasibility of including both A-002 and a statin in a single formulation, fixed dose tablets containing 250 mg A-002 and 40 mg simvastatin (marketed as Zocor®) were generated. Unit and batch formulas for these tablets are set forth in Tables 27 and 28, respectively. All inactive ingredients were purchased from Spectrum Chemicals. Butylated hydroxyanisole was included in the formulation for consistency with the marketed form of simvastatin (Zocor®).

TABLE 27

Unit formula for A-002/simvastatin tablets:

| Component | Function | mg/tablet |
|---|---|---|
| A-002 | Active ingredient | 250 |
| Simvastatin | Active ingredient | 40 |
| Anhydrous lactose | Diluent | 119.18 |
| Lactose fast flo | Diluent | 59.58 |
| Hydroxypropyl cellulose (HPC) | Binder | 13.5 |
| Croscarmellose sodium (divided into two equal portions for inner/extra granular | Disintegrant | 24.3 |
| Polysorbate 80 | Surfactant | 0.54 |
| Butylated hydroxyanisole (BHA) | Antioxidant | 0.01% |
| Microcrystalline cellulose 200 (MCC) | Diluent | 70.20 |
| Magnesium stearate | Lubricant | 2.70 |
| Purified water | Solvent | — |
| Total tablet weight |  | 580 mg |

TABLE 28

Batch formula for A-002/simvastatin tablets:

| Component | Function | g/batch |
|---|---|---|
| A-002 | Active ingredient | 259 |
| Simvastatin | Active ingredient | 41 |
| Anhydrous lactose | Diluent | 123 |
| Lactose fast flo | Diluent | 62 |
| Hydroxypropyl cellulose (HPC) | Binder | 14 |
| Croscarmellose sodium (divided into two equal portions for inner/extra granular | Disintegrant | 6.6/8.4 |
| Polysorbate 80 | Surfactant | 1 |
| Butylated hydroxyanisole (BHA) | Antioxidant | 0.1 |
| Microcrystalline cellulose 200 (MCC) | Diluent | 62 |
| Magnesium stearate | Lubricant | 2.5 |
| Purified water | Solvent | 93 |
| Batch size |  | 673 g |

Figure 8:
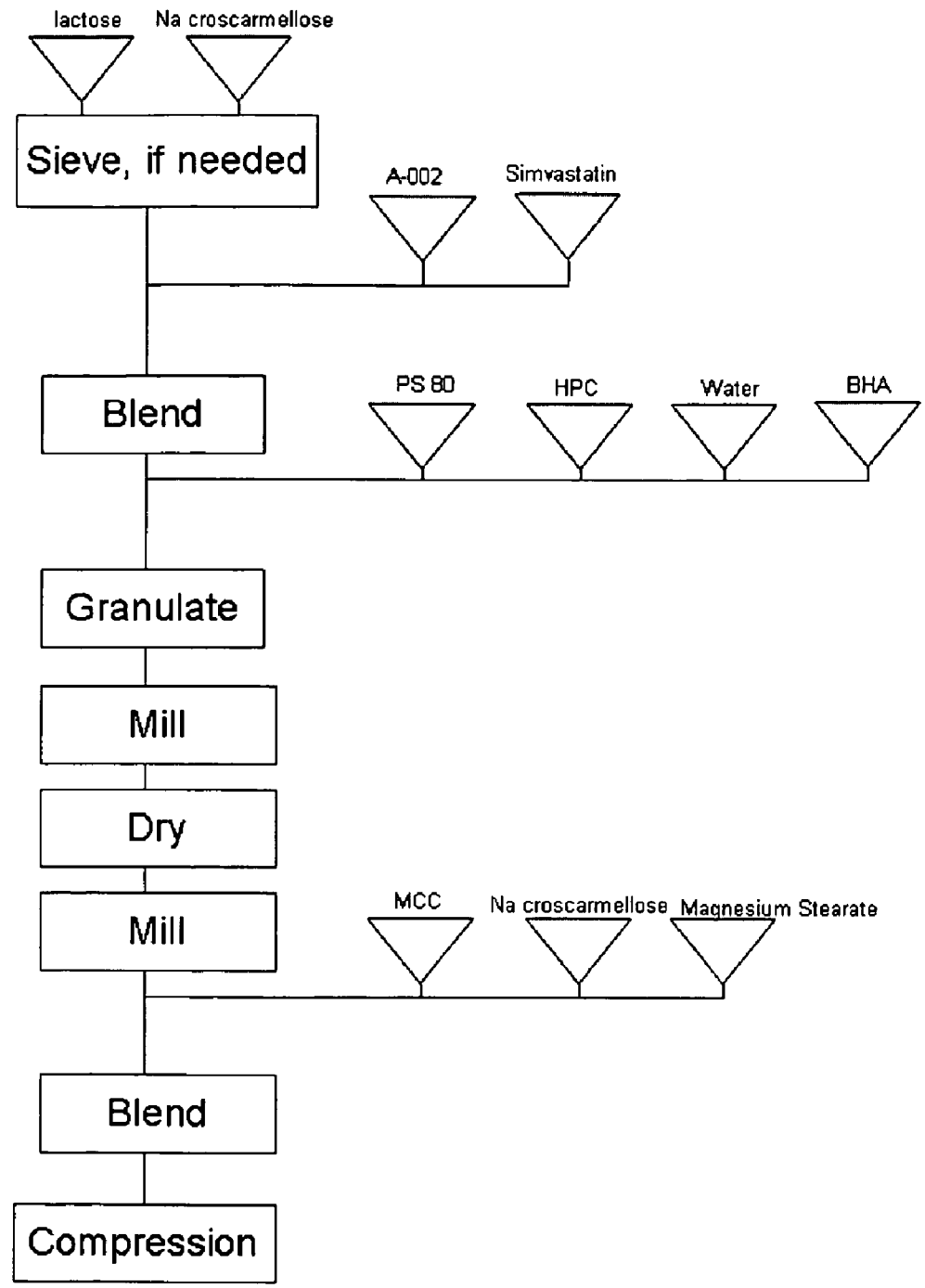
FIG. 8: A-002/simvastatin combination tablet preparation protocol.
Figure 9A:
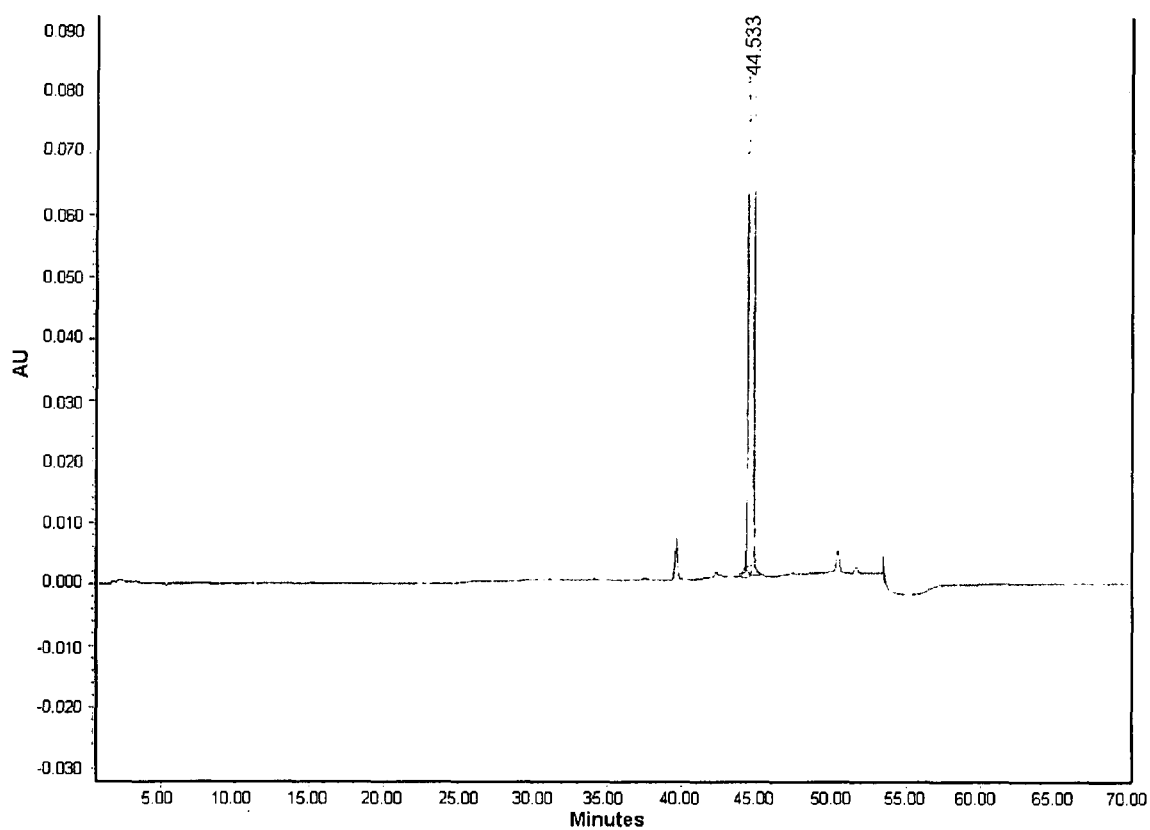
FIG. 9: HPLC profiles. A. Simvastatin. B. A-002. C. A-002/simvastatin combination tablet #19. D. A-002/simvastatin combination tablet #27.
Figure 9B:
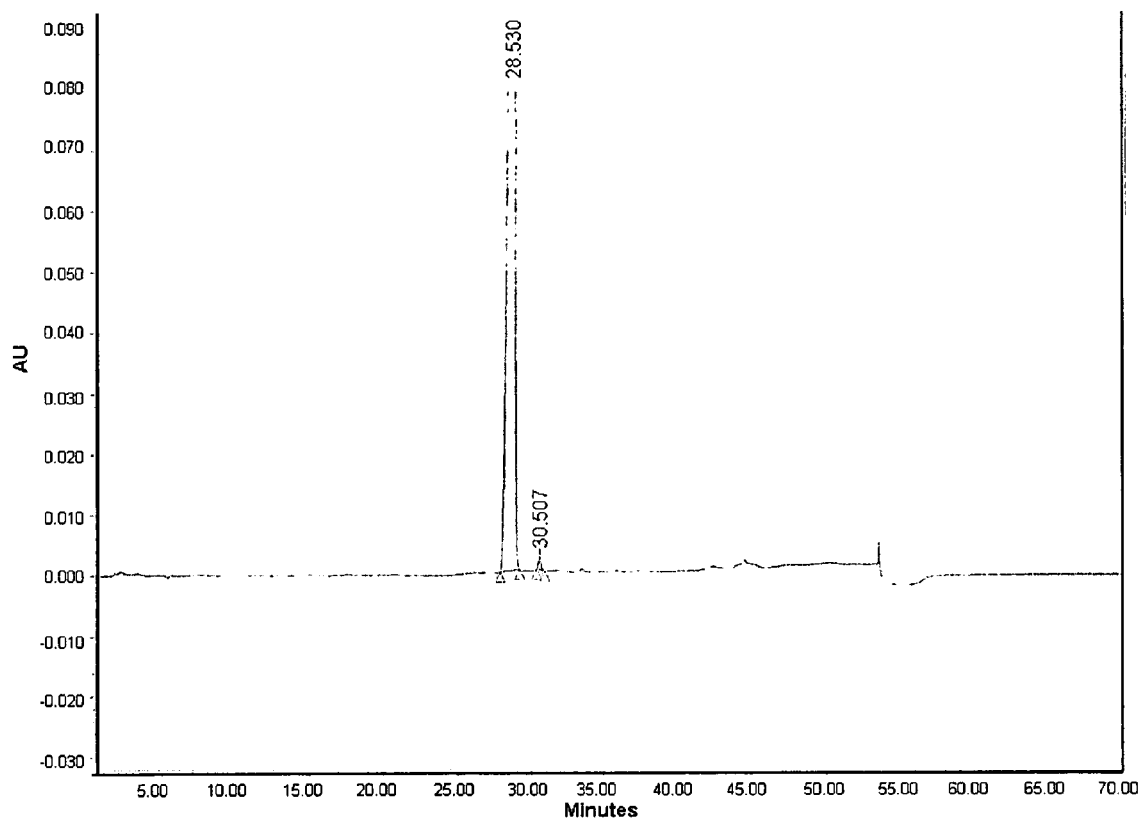
Figure 9C:
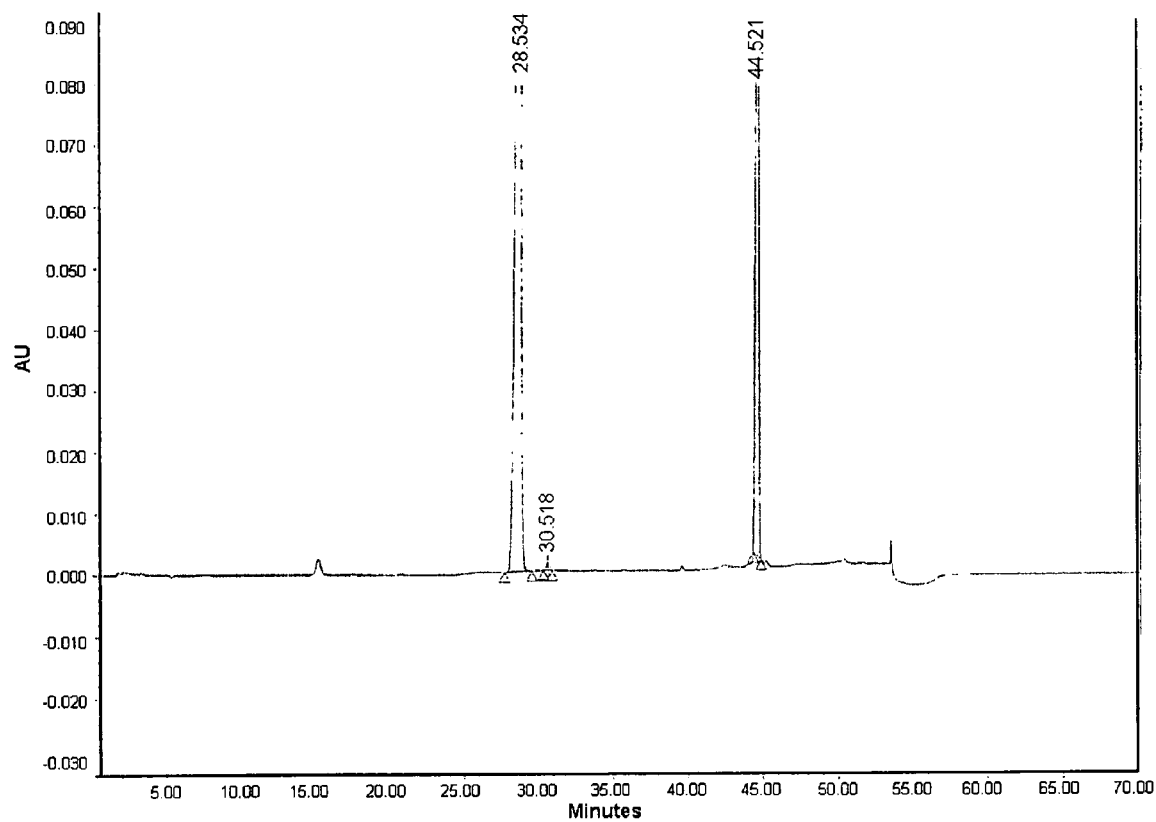
Figure 9D:
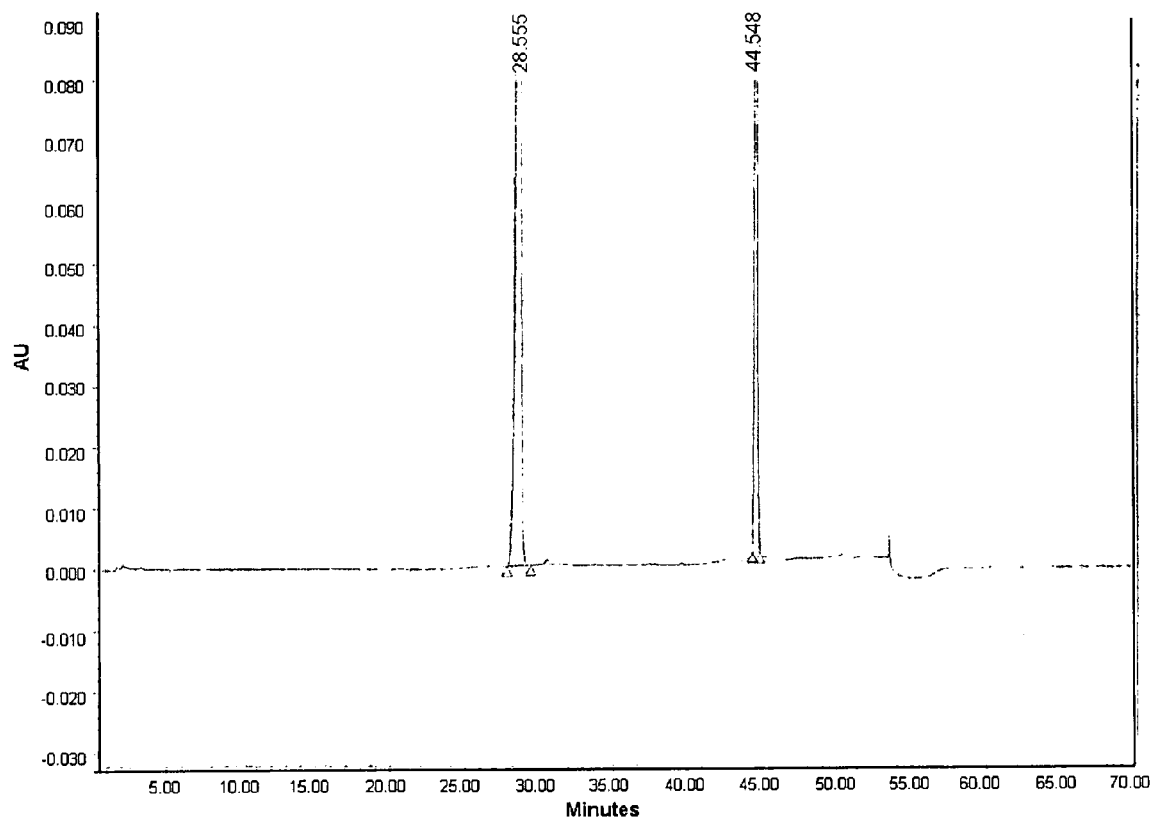

A flow chart detailing one method of preparing the tablet above is set forth in FIG. 8. BHA, polysorbate 80, and purified water were mixed to create granulation fluid, which was stored overnight. Lactose anhydrous, lactose fast flo, and the first portion of croscarmellose sodium were weighed and screened through a coarse mesh, then combined with A-002 and simvastatin (which can also be sieved if necessary) and dry blended for 1-2 minutes using a mixer at slow speed. In certain embodiments of this protocol, microcrystalline cellulose may be included in the dry mix. Hydroxypropyl cellulose was combined with the granulation fluid, resulting in greatly increased viscosity. The resultant solution was added slowly to the mixer containing the A-002/simvastatin mix. During addition, mixing speed was gradually increased. Granulation end-point was reached when fine granules formed without the mass becoming wet or sticky.

The granulation was screened through coarse mesh onto foil lined trays and placed in an oven at 50° C. and ambient humidity for approximately three hours. After drying (and optional milling and/or sieving), granules were placed in a low-density polyethylene (LDPE) bag. Approximately one-fourth of the dried granules were pre-blended with microcrystalline cellulose and magnesium stearate in a small baggy, and then the remainder of the granules were combined with the pre-blend in a mixer. The second portion of croscarmellose sodium was added in, and the entire mixture was mixed for several minutes. Tablets were prepared by weighing approximately 580 mg of the final blend into a tablet press and compressing at 200-2500 psi (Carver press). The resultant tablets were weighed individually, and had an average weight of approximately 0.6 g. Tablets appeared off-white to light tan in color.

Two representative tablets (numbers 19 and 27) were analyzed by reverse phase HPLC. Tablets were placed in a stability chamber at 25° C./60% RH. Representative HPLC results for two of the tablets are set forth in FIG. 9 and summarized in Table 29. Tablets maintained high potency (i.e., high concentrations of A-002 and simvastatin), thereby validating the feasibility of generating A-002/statin combination tablets for the treatment of various conditions.

TABLE 29

HPLC analysis of A-002/simvastatin combination tablets:

| Tablet # | Weight | % A-002 (RT: 28.5 minutes) | % simvastatin (RT: 44.5 minutes) |
|---|---|---|---|
| 19 | 0.64 g | 92% | 89% |
| 27 | 0.60 g | 88% | 86% |

A film coating may be applied to combination A-002/statin tablets using methods well known in the art. In one such method, the coating suspension is prepared by adding a film coat mixture such as Opadry YS-1-18027-A to purified water in a mixing vessel. The mixing speed is reduced to avoid foaming and the suspension is mixed for 60 or more minutes, until uniform. After mixing, the suspension is allowed to stand for 60 or more minutes to deaerate. A coater such as the Accela Coater is set up and the theoretical amount of coating suspension to be sprayed is calculated based on the number and size of tablets being coated. Tablets are loaded onto the coating pan, and the nozzle air pressure (around 80-100 psi), atomizing air pressure (around 25-45 psi), pattern air pressure (around 20-40 psi), delivery rate (around 300-400 g/minute), pan speed (around 4-10 rpm), and dew point setting (around 5-15° C.) are verified. The fan is turned on, and gun-to-bed distance (around 6-10 inches), supply air temperature (around 58° C.), exhaust air temperature (around 45° C.), air volume inlet (around 1500 cfm), and negative pan pressure differential are verified. The tablets are pre-heated, and a sample number of tablets are weighed to determine the average core tablet weight. The coating solution is sprayed onto the tablets while being gently mixed. At various intervals of around 5-15 minutes, the average tablet weight is recalculated. Once target tablet weight is reached, the supply air temperature is reduced to around 45° C. and the pan is jogged at intervals for around five minutes to allow the tablets to dry. The supply air temperature is reduced to around 30° C. and tablets are jogged manually for around ten more minutes. The coated tablets are then discharged from the coating pan.

Example 6

Once a Day Dosing of A-002 or A-002 Plus Statin 135 human subjects over the age of 18 with CVD, specifically stable CAD, were randomized to receive either placebo or one of two dosages (250 mg or 500 mg) of A-002 via once a day oral administration over an eight week time period. 89 of the subjects received A-002, while 46 of the subjects received placebo. Subjects that were receiving statins or other compounds used in the treatment of CVD at the outset of the trial continued to receive those therapeutics throughout the trial. 121 of the 135 subjects were on statins during the trial. There was little variation between dosage groups with respect to age, height, weight, or BMI.

Levels of various lipids and inflammatory markers were measured at the outset of the trial and at weeks two, four, and/or eight weeks after the start of A-002 administration. In addition, plasma A-002 levels were measured at various intervals. Lipids that were measured included LDL, small LDL particle, oxidized LDL, non-HDL cholesterol, total cholesterol, ApoB, and triglycerides. In addition, levels of the inflammatory marker CRP were measured. Lipid and inflammatory marker levels at each timepoint were compared to the baseline measurements to determine the effect of A-002 administration. For data sets with a normal distribution, mean levels of lipids or inflammatory markers were analyzed. For data sets with non-normal distribution, median levels were analyzed. LDL particle size was also assessed.

Subjects in the ITT population receiving A-002 at either dosage exhibited substantial decreases at week eight in mean serum LDL, non-HDL cholesterol, and total cholesterol levels (Tables 30-32, respectively) and in median small LDL particle, oxidized LDL, TG, and ApoB levels (Tables 33-36). Subjects receiving A-002 also exhibited an increase in mean LDL particle size (Table 37). In addition, subjects receiving A-002 did not show the same increase in median CRP levels that was observed in subjects receiving placebo (Table 38).

TABLE 30

Changes in serum LDL concentration in ITT population following A-002 administration:

| | | A-002 | Placebo |
|---|---|---|---|
| Baseline | # of subjects | 89 | 46 |
| | Mean [LDL] | 75.4 mg/dl | 82.0 mg/dl |
| Week 8 | # of subjects observed | 81 | 43 |
| | Change in mean | −7.1 mg/dl | −0.9 mg/dl |

TABLE 30-continued

Changes in serum LDL concentration in ITT population following A-002 administration:

|  | A-002 | Placebo |
|---|---|---|
| [LDL] vs. baseline % change vs. baseline | −8.3% | −0.7% |

TABLE 31

Changes in serum non-HDL cholesterol concentration in ITT population following A-002 administration:

|  |  | A-002 | Placebo |
|---|---|---|---|
| Baseline | # of subjects | 89 | 46 |
|  | Mean [non-HDL cholesterol] | 105.9 mg/dl | 112.5 mg/dl |
| Week 8 | # of subjects observed | 81 | 43 |
|  | Change in mean [non-HDL cholesterol] vs. baseline | −10.5 mg/dl | −2.1 mg/dl |
|  | % change vs. baseline | −9.9% | −0.7% |

TABLE 32

Changes in serum total cholesterol concentration in ITT population following A-002 administration:

|  |  | A-002 | Placebo |
|---|---|---|---|
| Baseline | # of subjects | 89 | 46 |
|  | Mean [total cholesterol] | 154.9 mg/dl | 159.9 mg/dl |
| Week 8 | # of subjects observed | 81 | 43 |
|  | Change in mean [total cholesterol] vs. baseline | −11.5 mg/dl | −3.1 mg/dl |
|  | % change vs. baseline | −7.3% | −1.7% |

TABLE 33

Changes in serum small LDL particle concentration in ITT population following A-002 administration:

|  |  | A-002 | Placebo |
|---|---|---|---|
| Baseline | # of subjects | 89 | 46 |
|  | Median [small LDL particle] | 759.0 nmol/L | 782.0 nmol/L |
| Week 8 | # of subjects observed | 81 | 43 |
|  | Change in median [small | −74.0 nmol/L | +2.0 nmol/L |

TABLE 33-continued

Changes in serum small LDL particle concentration in ITT population following A-002 administration:

|  | A-002 | Placebo |
|---|---|---|
| LDL particle] vs. baseline % change vs. baseline | −9.1% | +0.6% |

TABLE 34

Changes in serum oxidized LDL concentration in ITT population following A-002 administration:

|  |  | A-002 | Placebo |
|---|---|---|---|
| Baseline | # of subjects | 89 | 46 |
|  | Median [oxidized LDL] | 41.5 U/L | 43.3 U/L |
| Week 8 | # of subjects observed | 81 | 43 |
|  | Change in median [oxidized LDL] vs. baseline | −1.4 U/L | +0.3 U/L |
|  | % change vs. baseline | −3.6% | +0.4% |

TABLE 35

Changes in serum TG concentration in ITT population following A-002 administration:

|  |  | A-002 | Placebo |
|---|---|---|---|
| Baseline | # of subjects | 88 | 45 |
|  | Median [TG] | 137.5 mg/dl | 135.0 mg/dl |
| Week 8 | # of subjects observed | 81 | 43 |
|  | Change in median [TG] vs. baseline | −13.0 mg/dl | +3.0 mg/dl |
|  | % change vs. baseline | −9.8% | +2.6% |

TABLE 36

Changes in serum ApoB concentration in ITT population following A-002 administration:

|  |  | A-002 | Placebo |
|---|---|---|---|
| Baseline | # of subjects | 89 | 46 |
|  | Median [ApoB] | 68.6 mg/dl | 62.8 mg/dl |
| Week 8 | # of subjects observed | 81 | 43 |

TABLE 36-continued

Changes in serum ApoB concentration in ITT population following A-002 administration:

|  | A-002 | Placebo |
|---|---|---|
| Change in median [ApoB] vs. baseline | −8.1 mg/dl | +2.5 mg/dl |
| % change vs. baseline | −11.9% | +3.5% |

TABLE 37

Changes in LDL particle size in ITT population following A-002 administration:

|  |  | A-002 | Placebo |
|---|---|---|---|
| Baseline | # of subjects | 89 | 46 |
|  | Mean LDL particle size | 20.50 nm | 20.50 nm |
| Week 8 | # of subjects observed | 81 | 43 |
|  | Change in mean LDL particle size vs. baseline | +0.11 nm | 0.00 nm |
|  | % change vs. baseline | +0.6% | 0.0% |

TABLE 38

Changes in serum CRP concentration in ITT population following A-002 administration:

|  |  | A-002 | Placebo |
|---|---|---|---|
| Baseline | # of subjects | 89 | 46 |
|  | Median [CRP] | 1.10 mg/L | 1.30 mg/L |
| Week 8 | # of subjects observed | 81 | 43 |
|  | Change in median [CRP] vs. baseline | +0.10 ng/ml | +0.25 ng/ml |
|  | % change vs. baseline | +5.4% | +25.4% |

The decrease in mean serum LDL, non-HDL cholesterol, and total cholesterol levels and median small LDL particle, oxidized LDL, TG, and ApoB levels, the increase in mean LDL particle size, and the lower than expected increase in median CRP levels observed in the ITT population were also observed at eight weeks in the 121 subject subpopulation that was receiving statins during the trial (Tables 39-47, respectively), indicating that administration of A-002 plus statin results in a greater therapeutic effect on these markers than administration of statin alone. Likewise, a decrease in LDL, non-HDL cholesterol, total cholesterol, small LDL particle, oxidized LDL, and ApoB levels, an increase in LDL particle size, and a lower than expected increase in CRP levels were observed in 51 subjects within the statin subpopulation that had baseline LDL levels greater than 70 mg/dl (Tables 48-55). The number of subjects in the non-statin subpopulation was too low to allow for a detailed statistical analysis of the combined effect of A-002 and statins versus the effect of either compound alone. However, once additional non-statin controls are obtained, it is expected that a synergistic decrease in LDL levels similar to that observed following twice daily A-002 administration (Example 4) will be observed in subjects receiving A-002 once a day.

TABLE 39

Changes in serum LDL concentration in statin subpopulation following A-002 administration:

|  |  | A-002 | Placebo |
|---|---|---|---|
| Baseline | # of subjects | 81 | 40 |
|  | Mean [LDL] | 70.5 mg/dl | 75.5 mg/dl |
| Week 8 | # of subjects observed | 75 | 37 |
|  | Change in mean [LDL] vs. baseline | −6.7 mg/dl | −2.7 mg/dl |
|  | % change vs. baseline | −8.2% | −1.8% |

TABLE 40

Changes in serum non-HDL cholesterol concentration in statin subpopulation following A-002 administration:

|  |  | A-002 | Placebo |
|---|---|---|---|
| Baseline | # of subjects | 81 | 40 |
|  | Mean [non-HDL cholesterol] | 100.4 mg/dl | 104.8 mg/dl |
| Week 8 | # of subjects observed | 75 | 37 |
|  | Change in mean [non-HDL cholesterol] vs. baseline | −10.1 mg/dl | −3.2 mg/dl |
|  | % change vs. baseline | −9.9% | −1.3% |

TABLE 41

Changes in serum total cholesterol concentration in statin subpopulation following A-002 administration:

|  |  | A-002 | Placebo |
|---|---|---|---|
| Baseline | # of subjects | 81 | 40 |
|  | Mean [total cholesterol] | 149.3 mg/dl | 152.6 mg/dl |
| Week 8 | # of subjects observed | 75 | 37 |
|  | Change in mean [total cholesterol] vs. baseline | −11.2 mg/dl | −4.4 mg/dl |
|  | % change vs. baseline | −7.3% | −2.3% |

TABLE 42

Changes in serum small LDL particle concentration in statin subpopulation following A-002 administration:

| | | A-002 | Placebo |
|---|---|---|---|
| Baseline | # of subjects | 81 | 40 |
| | Median [small LDL particle] | 743.0 nmol/L | 773.5 nmol/L |
| Week 8 | # of subjects observed | 75 | 37 |
| | Change in median [small LDL particle] vs. baseline | −66.0 nmol/L | −6.5 nmol/L |
| | % change vs. baseline | −8.2% | −1.0% |

TABLE 43

Changes in serum oxidized LDL concentration in statin subpopulation following A-002 administration:

| | | A-002 | Placebo |
|---|---|---|---|
| Baseline | # of subjects | 81 | 40 |
| | Median [oxidized LDL] | 41.1 U/L | 42.2 U/L |
| Week 8 | # of subjects observed | 76 | 33 |
| | Change in median [oxidized LDL] vs. baseline | −1.1 U/L | +0.3 U/L |
| | % change vs. baseline | −2.9% | +0.4% |

TABLE 44

Changes in serum TG concentration in statin subpopulation following A-002 administration:

| | | A-002 | Placebo |
|---|---|---|---|
| Baseline | # of subjects | 80 | 39 |
| | Median [TG] | 136.5 mg/dl | 130.0 mg/dl |
| Week 8 | # of subjects observed | 75 | 37 |
| | Change in median [TG] vs. baseline | −13.0 mg/dl | +3.0 mg/dl |
| | % change vs. baseline | −10.9% | +2.6% |

TABLE 45

Changes in serum ApoB concentration in statin subpopulation following A-002 administration:

| | | A-002 | Placebo |
|---|---|---|---|
| Baseline | # of subjects | 81 | 40 |
| | Median [ApoB] | 66.1 mg/dl | 58.2 mg/dl |
| Week 8 | # of subjects observed | 75 | 37 |
| | Change in median [ApoB] vs. baseline | −7.9 mg/dl | +2.5 mg/dl |
| | % change vs. baseline | −11.9% | +3.5% |

TABLE 46

Changes in LDL particle size in statin subpopulation following A-002 administration:

| | | A-002 | Placebo |
|---|---|---|---|
| Baseline | # of subjects | 81 | 40 |
| | Mean LDL particle size | 20.50 nm | 20.48 nm |
| Week 8 | # of subjects observed | 75 | 37 |
| | Change in mean LDL particle size vs. baseline | +0.10 nm | −0.01 nm |
| | % change vs. baseline | +0.5% | 0.0% |

TABLE 47

Changes in serum CRP concentration in statin subpopulation following A-002 administration:

| | | A-002 | Placebo |
|---|---|---|---|
| Baseline | # of subjects | 81 | 40 |
| | Median [CRP] | 1.10 mg/L | 1.30 mg/L |
| Week 8 | # of subjects observed | 75 | 37 |
| | Change in median [CRP] vs. baseline | +0.10 mg/L | +0.30 mg/L |
| | % change vs. baseline | +8.7% | +40.6% |

TABLE 48

Changes in serum LDL concentration in statin subpopulation with baseline serum LDL levels greater than 70 mg/dl following A-002 administration:

| | | A-002 | Placebo |
|---|---|---|---|
| Baseline | # of subjects | 31 | 20 |
| | Mean [LDL] | 91.6 mg/dl | 93.2 mg/dl |
| Week 8 | # of subjects observed | 30 | 18 |
| | Change in mean [LDL] vs. baseline | −13.9 mg/dl | −5.0 mg/dl |
| | % change vs. baseline | −15.0% | −3.5% |

TABLE 49

Changes in serum non-HDL cholesterol concentration in statin subpopulation with baseline serum LDL levels greater than 70 mg/dl following A-002 administration:

| | | A-002 | Placebo |
|---|---|---|---|
| Baseline | # of subjects | 31 | 20 |
| | Mean [non-HDL cholesterol] | 123.3 mg/dl | 126.6 mg/dl |
| Week 8 | # of subjects observed | 30 | 18 |
| | Change in mean [non-HDL cholesterol] vs. baseline | −16.7 mg/dl | −7.2 mg/dl |
| | % change vs. baseline | −13.7% | −4.1% |

TABLE 50

Changes in serum total cholesterol concentration in statin subpopulation with baseline serum LDL levels greater than 70 mg/dl following A-002 administration:

| | | A-002 | Placebo |
|---|---|---|---|
| Baseline | # of subjects | 31 | 20 |
| | Mean [total cholesterol] | 172.5 mg/dl | 176.6 mg/dl |
| Week 8 | # of subjects observed | 30 | 18 |
| | Change in mean [total cholesterol] vs. baseline | −18.0 mg/dl | −8.6 mg/dl |
| | % change vs. baseline | −10.5% | −4.2% |

TABLE 51

Changes in serum small LDL particle concentration in statin subpopulation with baseline serum LDL levels greater than 70 mg/dl following A-002 administration:

| | | A-002 | Placebo |
|---|---|---|---|
| Baseline | # of subjects | 31 | 20 |
| | Median [small LDL particle] | 964.0 nmol/L | 919.5 nmol/L |
| Week 8 | # of subjects observed | 30 | 18 |
| | Change in median [small LDL particle] vs. baseline | −115.0 nmol/L | −70.0 nmol/L |
| | % change vs. baseline | −12.3% | −7.6% |

TABLE 52

Changes in serum oxidized LDL concentration in statin subpopulation with baseline serum LDL levels greater than 70 mg/dl following A-002 administration:

| | | A-002 | Placebo |
|---|---|---|---|
| Baseline | # of subjects | 31 | 20 |
| | Median [oxidized LDL] | 47.9 U/L | 51.6 U/L |
| Week 8 | # of subjects observed | 76 | 33 |
| | Change in median [oxidized LDL] vs. baseline | −2.8 U/L | +1.3 U/L |
| | % change vs. baseline | −5.6% | +2.5% |

TABLE 53

Changes in serum ApoB concentration in statin subpopulation with baseline serum LDL levels greater than 70 mg/dl following A-002 administration:

| | | A-002 | Placebo |
|---|---|---|---|
| Baseline | # of subjects | 31 | 20 |
| | Median [ApoB] | 84.6 mg/dl | 71.9 mg/dl |
| Week 8 | # of subjects observed | 30 | 18 |
| | Change in median [ApoB] vs. baseline | −13.1 mg/dl | +1.1 mg/dl |
| | % change vs. baseline | −18.7% | +2.1% |

TABLE 54

Changes in LDL particle size in statin subpopulation with baseline serum LDL levels greater than 70 mg/dl following A-002 administration:

| | | A-002 | Placebo |
|---|---|---|---|
| Baseline | # of subjects | 31 | 20 |
| | Mean LDL particle size | 20.24 nm | 20.62 nm |
| Week 8 | # of subjects observed | 30 | 18 |
| | Change in mean LDL particle size vs. baseline | +0.19 nm | +0.02 nm |
| | % change vs. baseline | +1.0% | +0.1% |

TABLE 55

Changes in serum CRP concentration in statin subpopulation with baseline serum LDL levels greater than 70 mg/dl following A-002 administration:

| | | A-002 | Placebo |
|---|---|---|---|
| Baseline | # of subjects | 31 | 20 |
| | Median [CRP] | 1.10 mg/L | 1.30 mg/L |
| Week 8 | # of subjects observed | 30 | 18 |
| | Change in median [CRP] vs. baseline | +0.10 mg/L | +0.45 mg/L |
| | % change vs. baseline | +9.1% | +26.0% |

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Boekholdt et al. 2005. Arterioscler Thromb Vasc Biol 25:839-846.
2. Bostrom et al. 2007. Arterioscler Thromb Vasc Biol 27:600-606.
3. Camejo et al. 1998. Atherosclerosis 139:205-222.
4. Chait, A., et al. 2005. J Lipid Res 46:389-403.
5. Daugherty et al. 2000. J Clin Invest 105:1605-1612.
6. Elinder et al. 1997. Arterioscler Thromb Vasc Biol 17:2257-2263.
7. Hakala et al. 2001. Arterioscler Thromb Vasc Biol 21:1053-1058.
8. Hartford et al. 2006. J Cardiol 108:55-62.
9. Ivandic et al. 1999. Arterioscler Thromb Vasc Biol 19:1284-1290.
10. Jialal, I. 1998. Clin Chem 44:1827-1832.
11. Kimura-Matsumoto et al. Atherosclerosis Epub Mar. 10, 2007.
12. Kugiyama et al. 1999. Circulation 100:1280-1284.
13. Liu et al. 2003. Eur Heart J 24:1824-1832.
14. Mallat et al. 2007. Arterioscler Thromb Vasc Biol 27:1177-1183.
15. Mallat et al. 2005. J Am Coll Cardiol 46:1249-1257.
16. Menschikowski et al. 1995. Atherosclerosis 118:173-181.
17. Nijmeijer et al. 2002. Cardiovasc Res 53:138-146.
18. Pruzanski et al. 1998. J Lipid Res 39:2150-2160.
19. Ramoner et al. 2005. Blood 105:3583.
20. Rosengren, B., et al. 2006. Arterioscler Thromb Vasc Biol 26:1579-1585.
21. Sartipy et al. 1999. J Biol Chem 274:25913-25920.
22. Szmitko et al. 2003. Circulation 108:2041.
23. Tietge et al. 2000. J Biol Chem 275:10077-10084.

What is claimed is:

1. A composition comprising ((3-(2-Amino-1,2-dioxoethyl)-2-ethyl-1-(phenylmethyl)-1H-indol-4-yl)oxy)acetic acid or a pharmaceutically acceptable salt, polymorph, co-crystal, solvate, or prodrug derivative thereof and a statin.

2. The composition of claim 1, wherein said prodrug derivative is [[3-(2-Amino-1,2-dioxoethyl)-2-ethyl-1-(phenylmethyl)-1H-indol-4-yl]oxy]acetic acid methyl ester.

3. The composition of claim 1, wherein said statin is selected from the group consisting of atorvastatin, cerivastatin, fluvastatin, lovastatin, mevastatin, pitavastatin, pravastatin, rosuvastatin, simvastatin, and pharmaceutically acceptable salts, solvates, stereoisomers, or prodrug derivatives thereof.

4. The composition of claim 1, further comprising one or more compounds selected from the group consisting of ezetimibe, amlodipine, CP-529414, APA-01, extended release niacin, MK-0524A, fenofibrate, and TAK-457.

5. The composition of claim 1, wherein the combination of ((3-(2-Amino-1,2-dioxoethyl)-2-ethyl-1-(phenylmethyl)-1H-indol-4-yl)oxy)acetic acid or a pharmaceutically acceptable salt, polymorph, co-crystal, solvate, or prodrug derivative thereof and a statin has a greater than additive effect in the treatment of a cardiovascular disease associated with elevated LDL levels and/or atherosclerosis when administered to a subject in need thereof.

6. The composition of claim 1, wherein the combination of ((3-(2-Amino-1,2-dioxoethyl)-2-ethyl-1-(phenylmethyl)-1H-indol-4-yl)oxy)acetic acid or a pharmaceutically acceptable salt, polymorph, co-crystal, solvate, or prodrug derivative thereof and a statin has a synergistic effect in the treatment of a cardiovascular disease associated with elevated LDL levels and/or atherosclerosis when administered to a subject in need thereof.

7. The composition of claim 1, wherein the combination of ((3-(2-Amino-1,2-dioxoethyl)-2-ethyl-1-(phenylmethyl)-1H-indol-4-yl)oxy)acetic acid or a pharmaceutically acceptable salt, polymorph, co-crystal, solvate, or prodrug derivative thereof and a statin has a greater than additive effect in the reduction of LDL levels when administered to a subject in need thereof.

8. The composition of claim 1, wherein the combination of ((3-(2-Amino-1,2-dioxoethyl)-2-ethyl-1-(phenylmethyl)-1H-indol-4-yl)oxy)acetic acid or a pharmaceutically acceptable salt, polymorph, co-crystal, solvate, or prodrug derivative thereof and a statin has a synergistic effect in the reduction of LDL levels when administered to a subject in need thereof.

9. A composition comprising ((3-(2-Amino-1,2-dioxoethyl)-2-ethyl-1-(phenylmethyl)-1H-indol-4-yl)oxy)acetic acid or a pharmaceutically acceptable salt, polymorph, co-crystal, solvate, or prodrug derivative for administration in combination with a statin.

10. The composition of claim 9, wherein said composition is administered simultaneous with a statin.

11. The composition of claim 9, wherein said composition is administered sequentially with a statin.

12. The composition of claim 9, wherein said prodrug derivative is [[3-(2-Amino-1,2-dioxoethyl)-2-ethyl-1-(phenylmethyl)-1H-indol-4-yl]oxy]acetic acid methyl ester.

13. The composition of claim 9, wherein administration of said composition in combination with a statin to a subject in need thereof results in a greater than additive effect in the treatment of a cardiovascular disease associated with elevated LDL levels and/or atherosclerosis.

14. The composition of claim 9, wherein administration of said composition in combination with a statin to a subject in need thereof results in a synergistic effect in the treatment of a cardiovascular disease associated with elevated LDL levels and/or atherosclerosis.

15. The composition of claim 9, wherein administration of said composition in combination with a statin to a subject in need thereof results in a greater than additive effect in the reduction of LDL levels.

16. The composition of claim 9, wherein administration of said composition in combination with a statin to a subject in need thereof results in a synergistic effect in the reduction of LDL levels.

17. A composition comprising ((3-(2-Amino-1,2-dioxoethyl)-2-ethyl-1-(phenylmethyl)-1H-indol-4-yl)oxy)acetic acid or a pharmaceutically acceptable salt, polymorph, co-crystal, solvate, or prodrug derivative for administration in combination with a statin to treat a cardiovascular disease associated with elevated LDL levels and/or atherosclerosis.

18. A composition comprising [[3-(2-Amino-1,2-dioxoethyl)-2-ethyl-1-(phenylmethyl)-1H-indol-4-yl]oxy]acetic acid methyl ester for administration in combination with a statin to treat a cardiovascular disease associated with elevated LDL levels and/or atherosclerosis.

19. A pharmaceutical composition comprising ((3-(2-Amino-1,2-dioxoethyl)-2-ethyl-1-(phenylmethyl)-1H-indol-4-yl)oxy)acetic acid or a pharmaceutically acceptable salt, polymorph, co-crystal, solvate, or prodrug derivative thereof, a statin, and one or more pharmaceutically acceptable carriers.

20. The pharmaceutical composition of claim 19, wherein said prodrug derivative is [[3-(2-Amino-1,2-dioxoethyl)-2-ethyl-1-(phenylmethyl)-1H-indol-4-yl]oxy]acetic acid methyl ester.

21. A pharmaceutical composition for administration in combination with a statin comprising ((3-(2-Amino-1,2-dioxoethyl)-2-ethyl-1-(phenylmethyl)-1H-indol-4-yl)oxy)acetic acid or a pharmaceutically acceptable salt, polymorph, co-crystal, solvate, or prodrug derivative thereof and one or more pharmaceutically acceptable carriers, wherein said composition is administered simultaneous with or sequentially with a statin.

22. The pharmaceutical composition of claim 21, wherein said prodrug derivative is [[3-(2-Amino-1,2-dioxoethyl)-2-ethyl-1-(phenylmethyl)-1H-indol-4-yl]oxy]acetic acid methyl ester.

23. A kit comprising ((3-(2-Amino-1,2-dioxoethyl)-2-ethyl-1-(phenylmethyl)-1H-indol-4-yl)oxy)acetic acid or a pharmaceutically acceptable salt, polymorph, co-crystal, solvate, or prodrug derivative thereof and a statin.

24. The kit of claim 23, wherein said ((3-(2-Amino-1,2-dioxoethyl)-2-ethyl-1-(phenylmethyl)-1H-indol-4-yl)oxy) acetic acid or a pharmaceutically acceptable salt, polymorph, co-crystal, solvate, or prodrug derivative thereof and said statin are divided into separate compartments.

25. The kit of claim 23, wherein said ((3-(2-Amino-1,2-dioxoethyl)-2-ethyl-1-(phenylmethyl)-1H-indol-4-yl)oxy) acetic acid or a pharmaceutically acceptable salt, polymorph, co-crystal, solvate, or prodrug derivative thereof and said statin are divided into separate compartments.

26. The kit of claim 23, wherein said ((3-(2-Amino-1,2-dioxoethyl)-2-ethyl-1-(phenylmethyl)-1H-indol-4-yl)oxy) acetic acid or a pharmaceutically acceptable salt, polymorph, co-crystal, solvate, or prodrug derivative thereof and said statin are held within a single undivided container.

27. The kit of claim 26, wherein said ((3-(2-Amino-1,2-dioxoethyl)-2-ethyl-1-(phenylmethyl)-1H-indol-4-yl)oxy) acetic acid or a pharmaceutically acceptable salt, polymorph, co-crystal, solvate, or prodrug derivative thereof and said statin are part of a single pharmaceutical composition.

28. The kit of claim 23, wherein said kit further comprises instructions for usage.

29. The kit of claim 23 for use in lowering LDL and/or small LDL particle levels in a subject in need thereof.

30. The kit of claim 23 for use in treating a cardiovascular disease associated with elevated LDL levels and/or atherosclerosis.

* * * * *

UNITED STATES PATENT AND TRADEMARK OFFICE
CERTIFICATE OF CORRECTION

| | |
|---|---|
| PATENT NO. | : 8,048,880 B2 |
| APPLICATION NO. | : 12/114710 |
| DATED | : November 1, 2011 |
| INVENTOR(S) | : Joaquim Trias et al. |

It is certified that error appears in the above-identified patent and that said Letters Patent is hereby corrected as shown below:

On the Face page, in Field (75) "INVENTORS", Column 1, Line 7, please delete "Kenneth Gould, Zionsville, IN (US);".

On the Face page, in Field (75) "INVENTORS", Column 1, Line 8, please delete "Marian Mosior, Indianapolis, IN (US);".

On the Face page, in Field (75) "INVENTORS", Column 1, Line 9, please delete "Patrick Eacho, Indianapolis, IN (US)".

Signed and Sealed this
Fifth Day of June, 2012

David J. Kappos
*Director of the United States Patent and Trademark Office*